United States Patent
Segev

(10) Patent No.: US 7,034,131 B2
(45) Date of Patent: Apr. 25, 2006

(54) NUCLEIC ACID DERIVATIVES

(75) Inventor: David Segev, Mazkeret Batya (IL)

(73) Assignee: Bio-Rad Laboratories Inc., Hercules, CA (US)

( * ) Notice: Subject to any disclaimer, the term of this patent is extended or adjusted under 35 U.S.C. 154(b) by 329 days.

(21) Appl. No.: 10/057,928

(22) Filed: Jan. 29, 2002

(65) Prior Publication Data

US 2003/0191074 A1  Oct. 9, 2003

Related U.S. Application Data

(60) Provisional application No. 60/264,308, filed on Jan. 29, 2001.

(51) Int. Cl.
| C07H 21/00 | (2006.01) |
| C07H 21/02 | (2006.01) |
| C07H 21/04 | (2006.01) |
| A01N 61/00 | (2006.01) |
| C12P 13/00 | (2006.01) |

(52) U.S. Cl. .................. 536/23.1; 536/24.3; 536/25.3; 536/25.32; 514/1; 514/44; 435/6; 435/128

(58) Field of Classification Search ............... 536/23.1, 536/24.3, 25.3, 25.32, 18.7; 514/1, 44; 435/6, 435/128
See application file for complete search history.

(56) References Cited

U.S. PATENT DOCUMENTS

| 4,179,337 A | 12/1979 | Davis et al. |
| 5,908,845 A | 6/1999 | Segev |

FOREIGN PATENT DOCUMENTS

| WO | WO86/05518 | 9/1986 |
| WO | WO86/05519 | 9/1986 |
| WO | WO89/12060 | 12/1989 |
| WO | WO92/20702 | 11/1992 |
| WO | WO01/16365 | 7/2000 |

OTHER PUBLICATIONS

Uhlmann et al. Chemical Reviews, vol. 90, No. 4, Jun. 1990, pp. 543-584.*

* cited by examiner

*Primary Examiner*—Jezia Riley

(57) ABSTRACT

A compound which comprises a backbone having a plurality of chiral carbon atoms, the backbone bearing a plurality of ligands each being individually bound to a chiral carbon atom of the plurality of chiral carbon atoms, the ligands including one or more pair(s) of adjacent ligands each containing a moiety selected from the group consisting of a naturally occurring nucleobase and a nucleobase binding group, wherein moieties of the one or more pair(s) are directly linked to one another via a linker chain; building blocks for synthesizing the compound; and rises of the compound, particularly in antisense therapy.

33 Claims, 33 Drawing Sheets

Compound 1

Compound 2

Compound 3

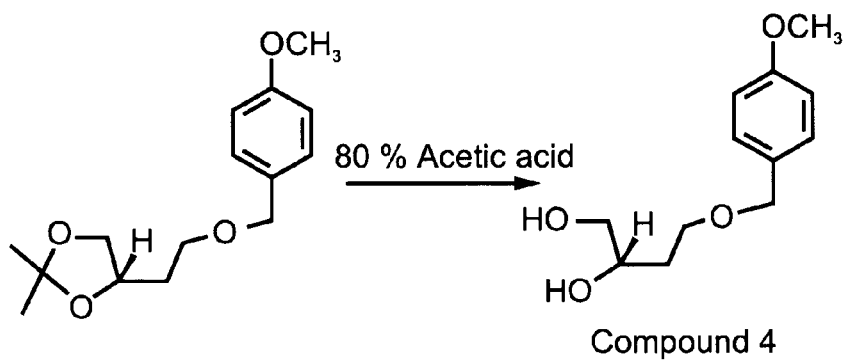
Compound 4
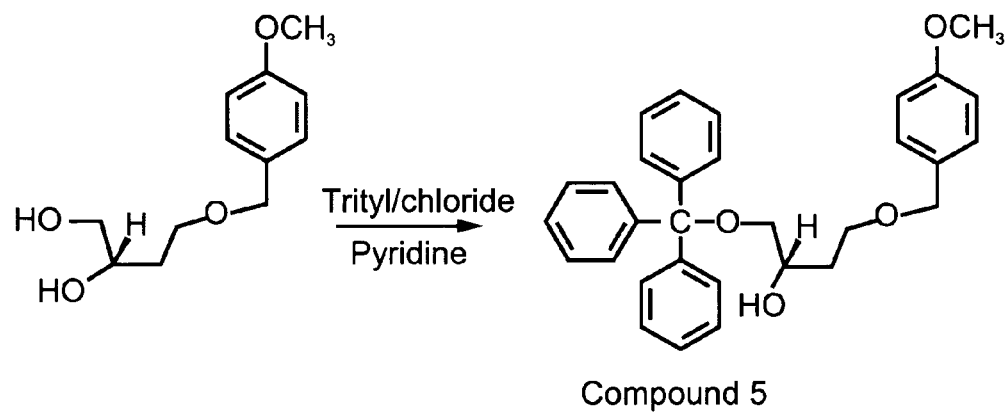
Compound 5
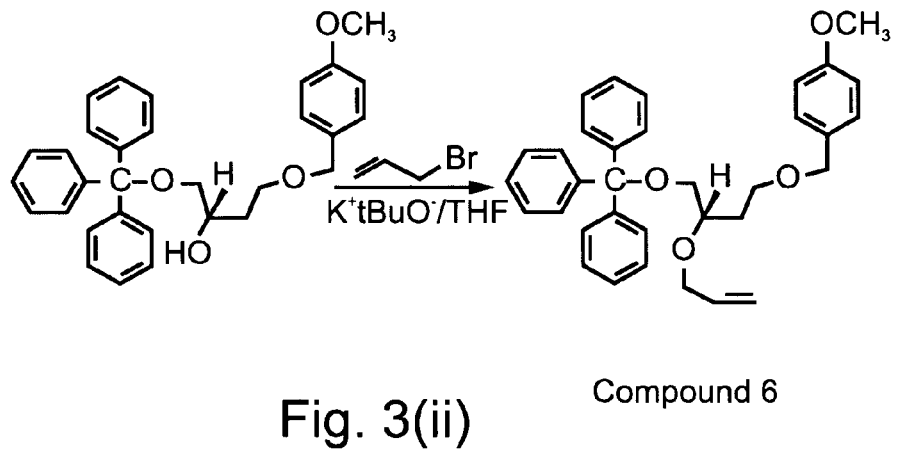
Fig. 3(ii)    Compound 6

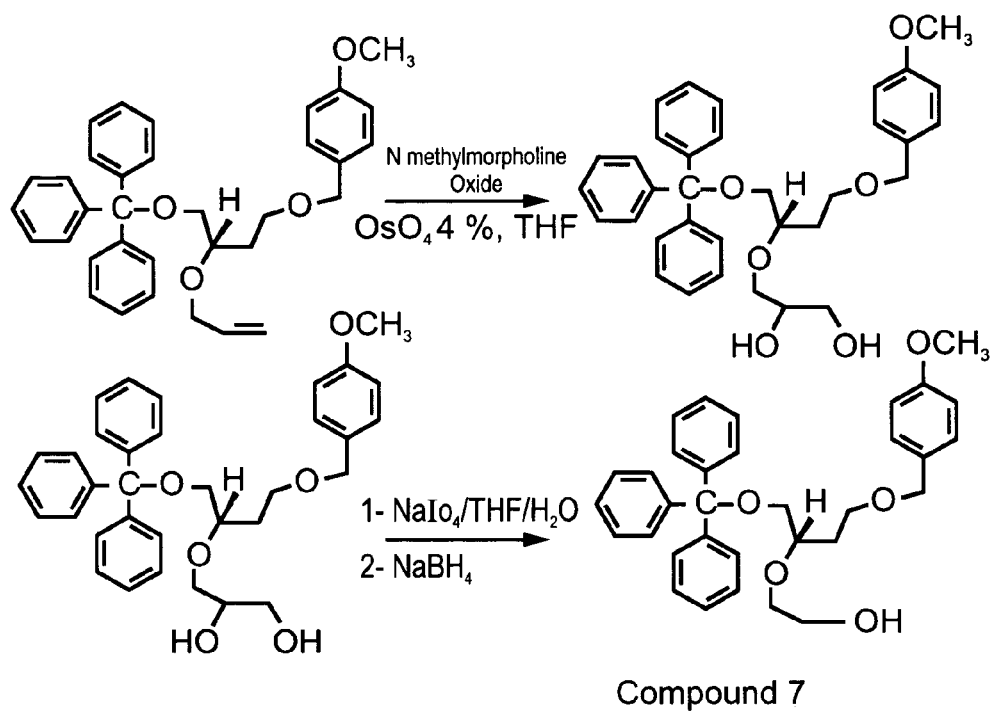
Compound 7
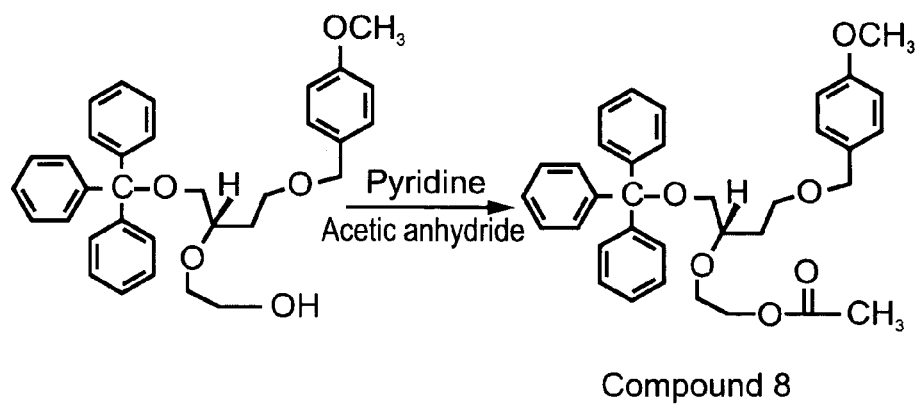
Compound 8
Fig. 3(iii)

Compound 9

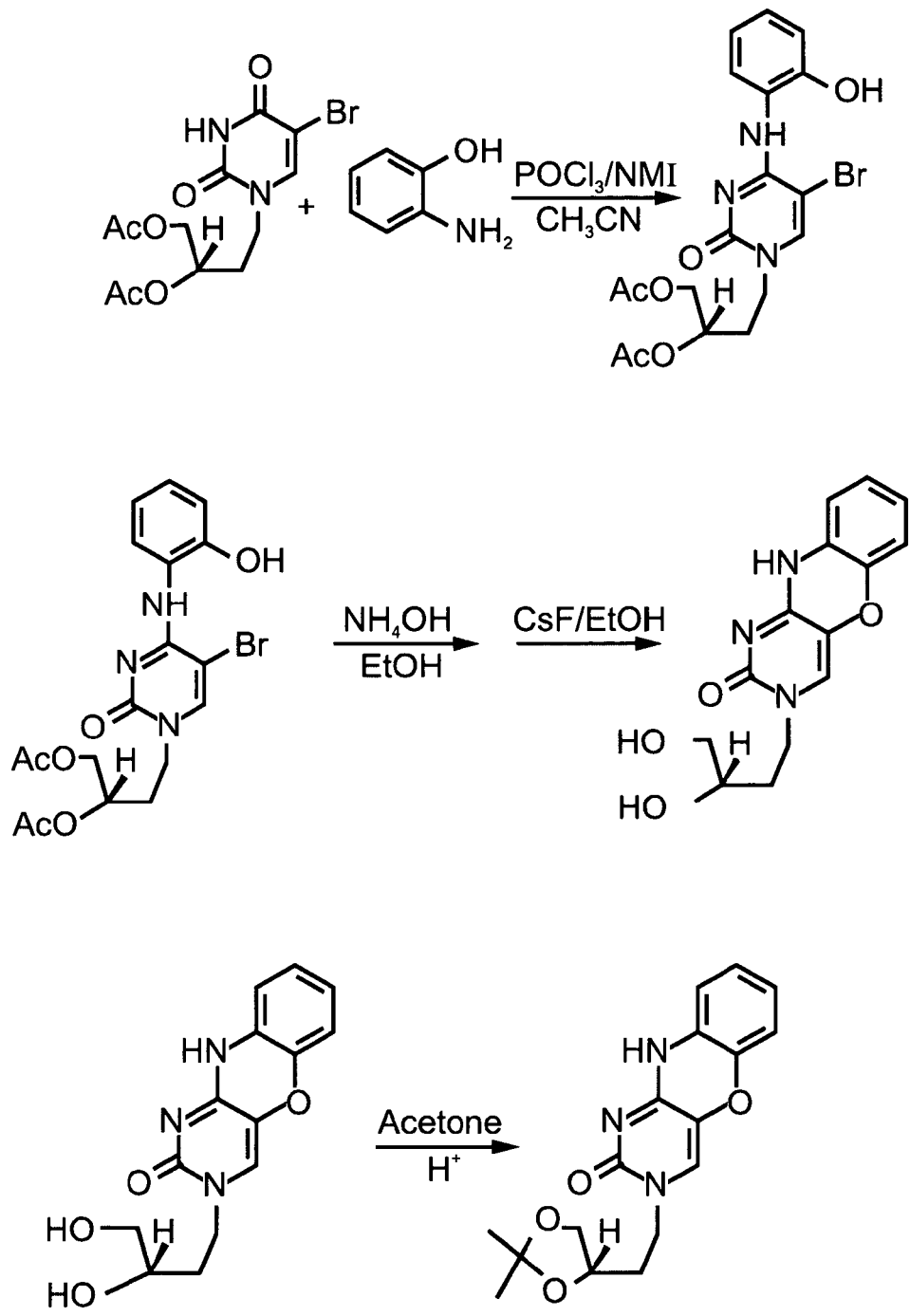
Fig. 4a(ii)

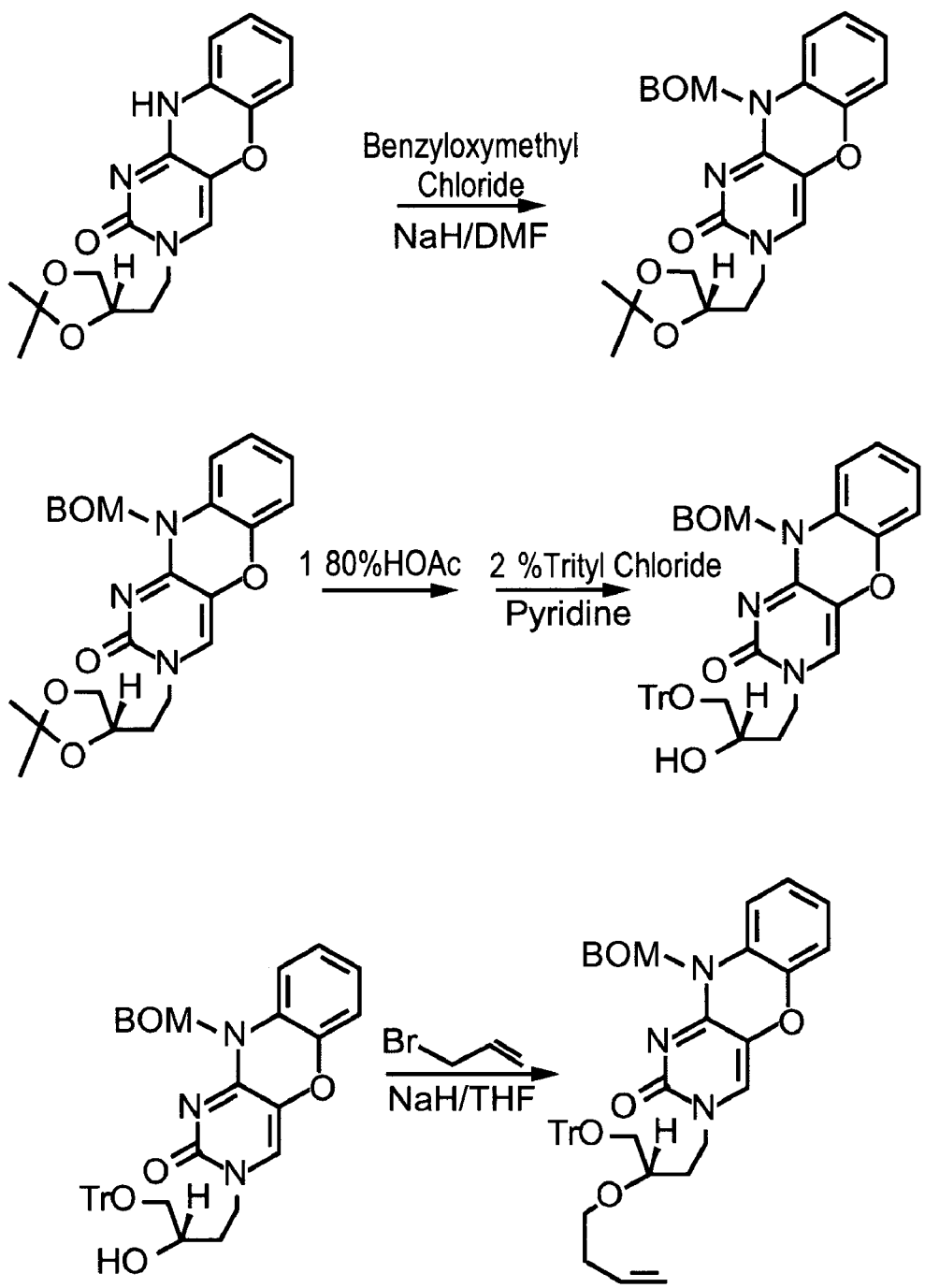
Fig. 4a(iii)

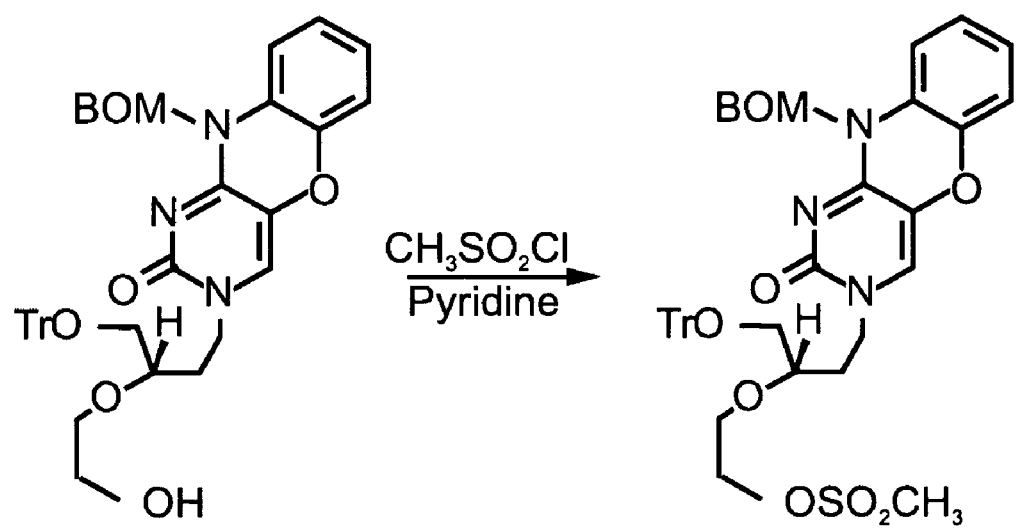
Fig. 4a(iv)

Compound 25

Compound 9  Compound 26

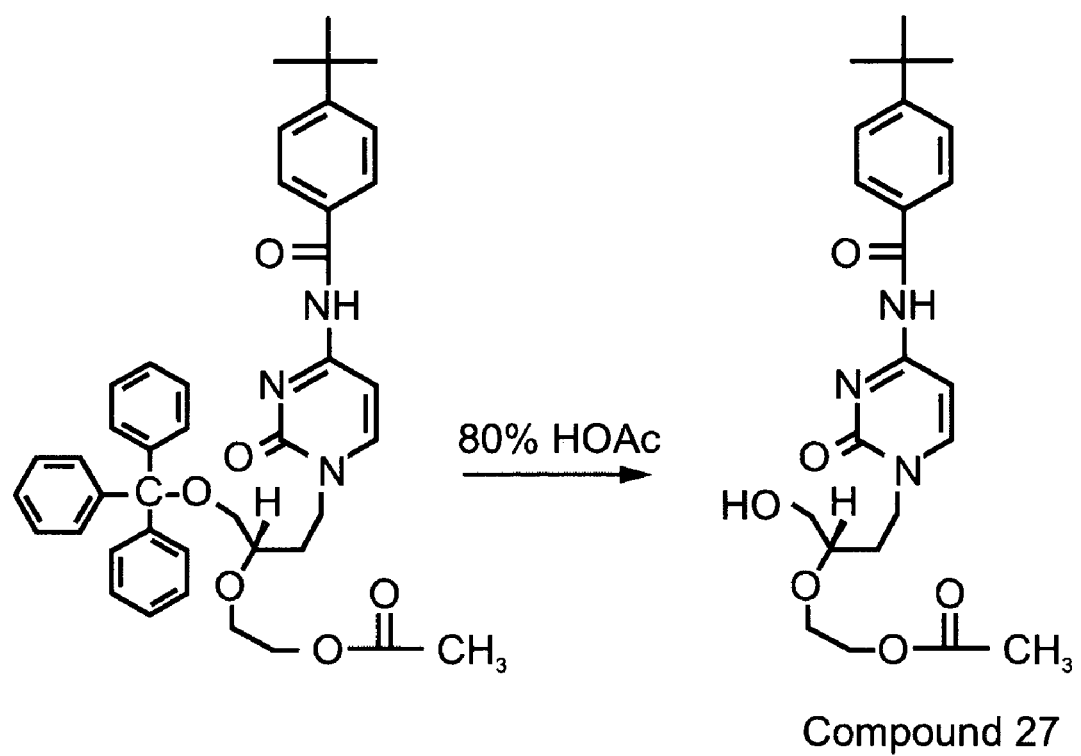
Fig. 4b(ii)

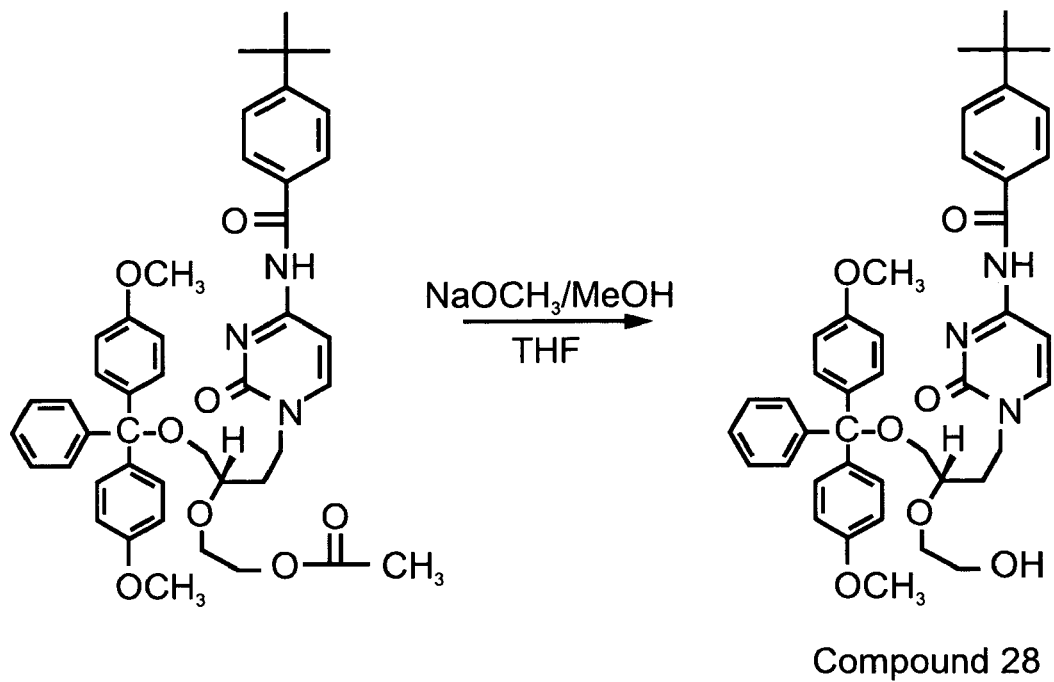
Compound 28
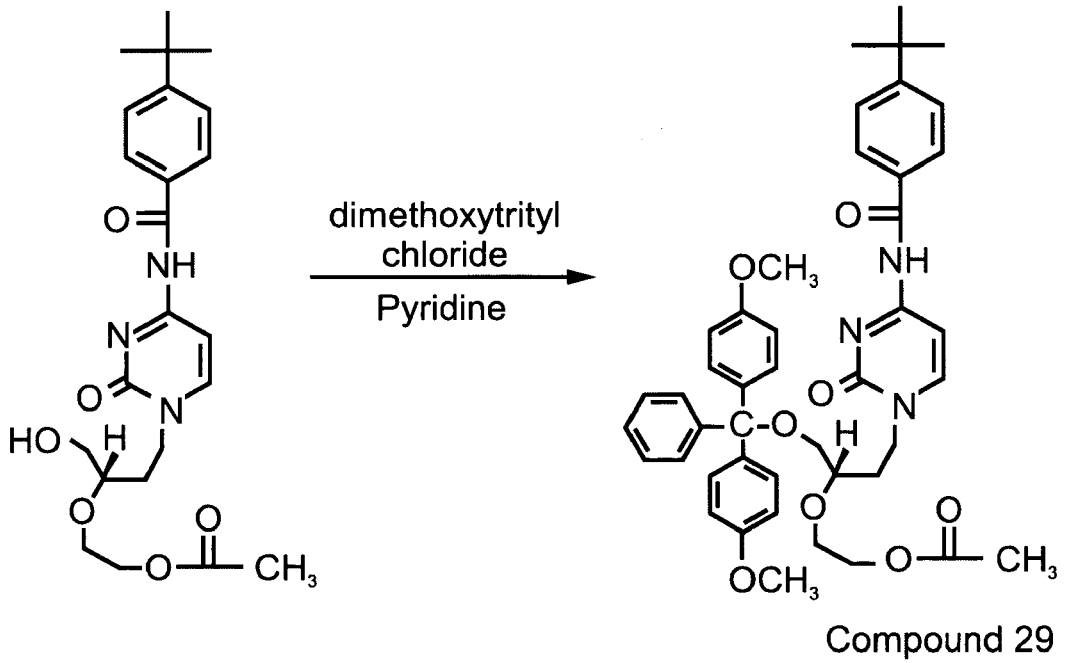
Compound 29
Fig. 4b(iii)

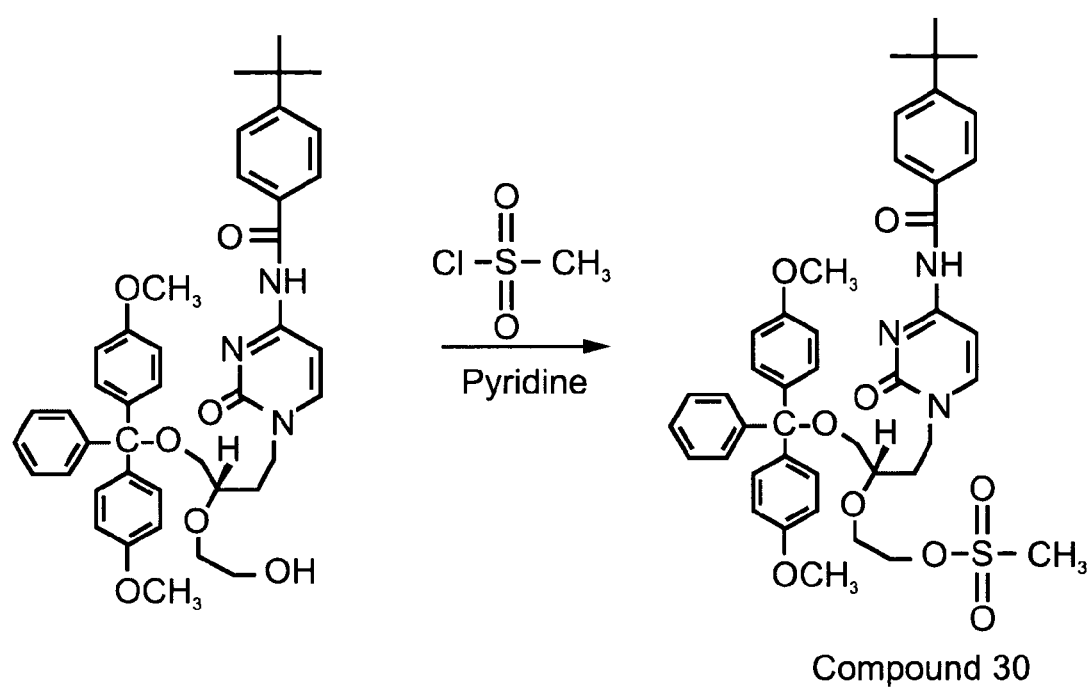
Compound 30
Fig. 4b(iv)

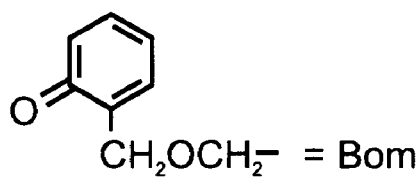
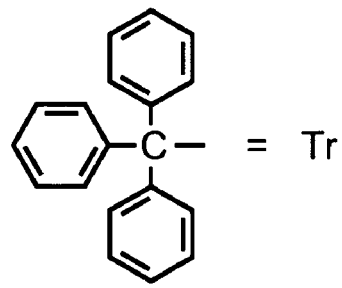
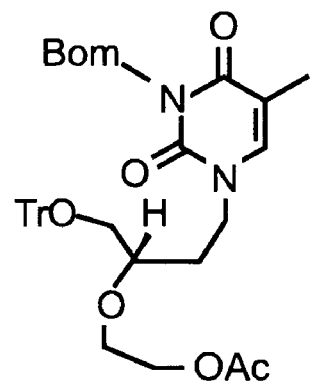
Compound 33
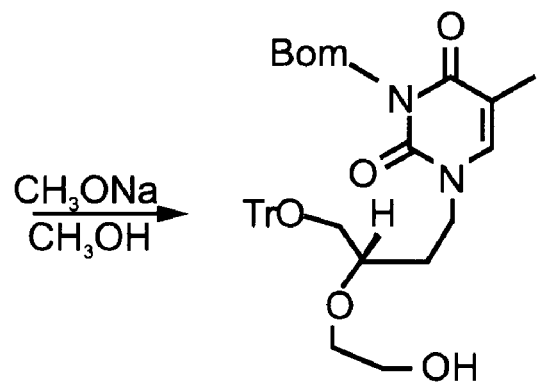
Compound 34
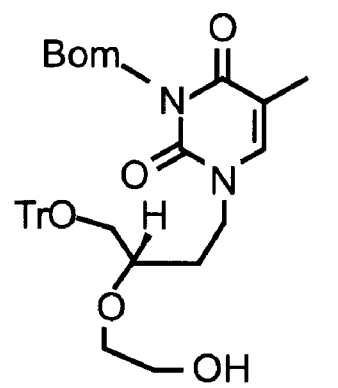
Compound 34
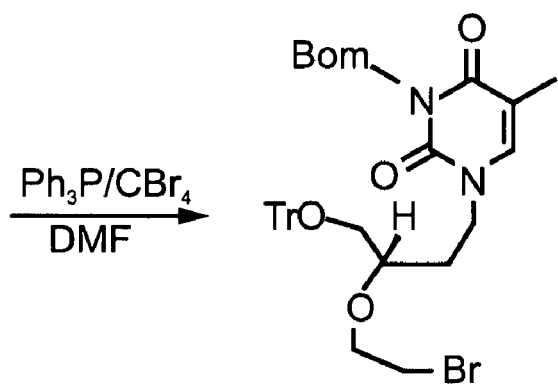
Compound 35
Fig. 5a(ii)

Compound 34 → Compound 34

Compound 36 → Compound 37

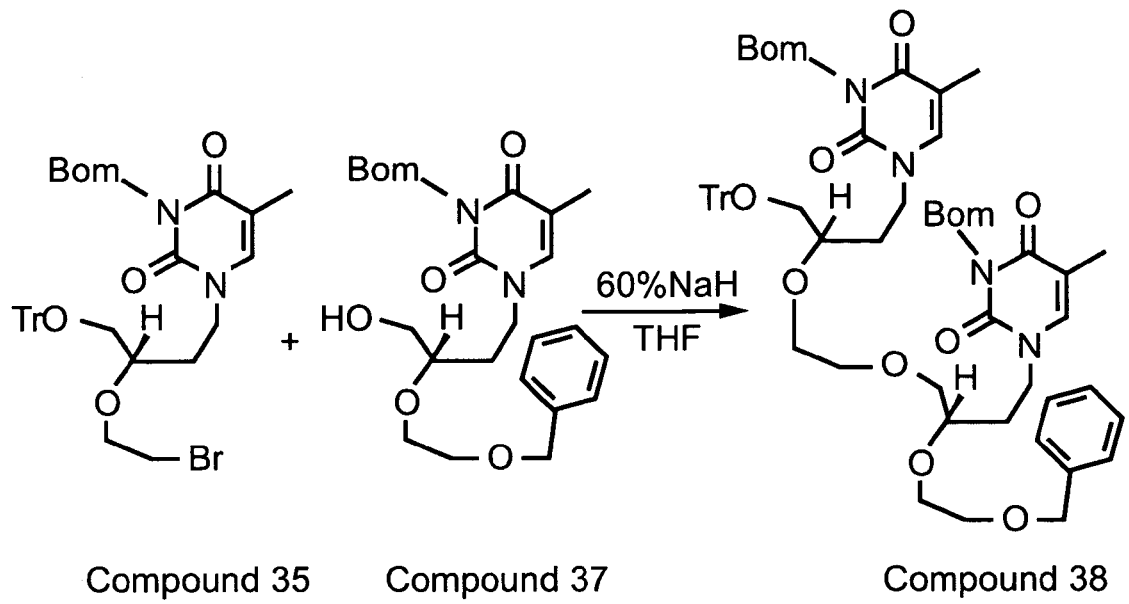
Compound 35    Compound 37    Compound 38
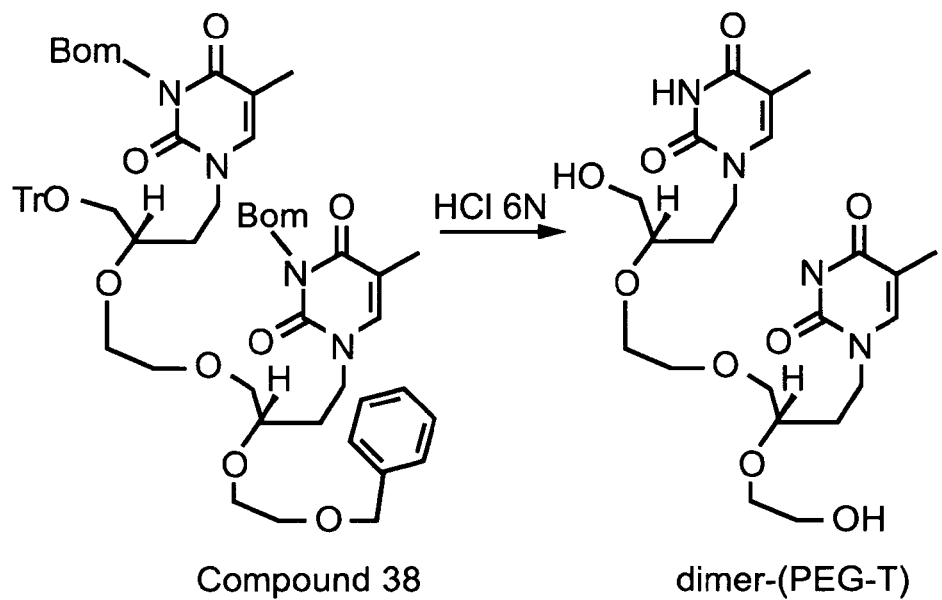
Compound 38    dimer-(PEG-T)
Fig. 6a(ii)

Compound 38 → Compound 46

Compound 46 → Compound 47

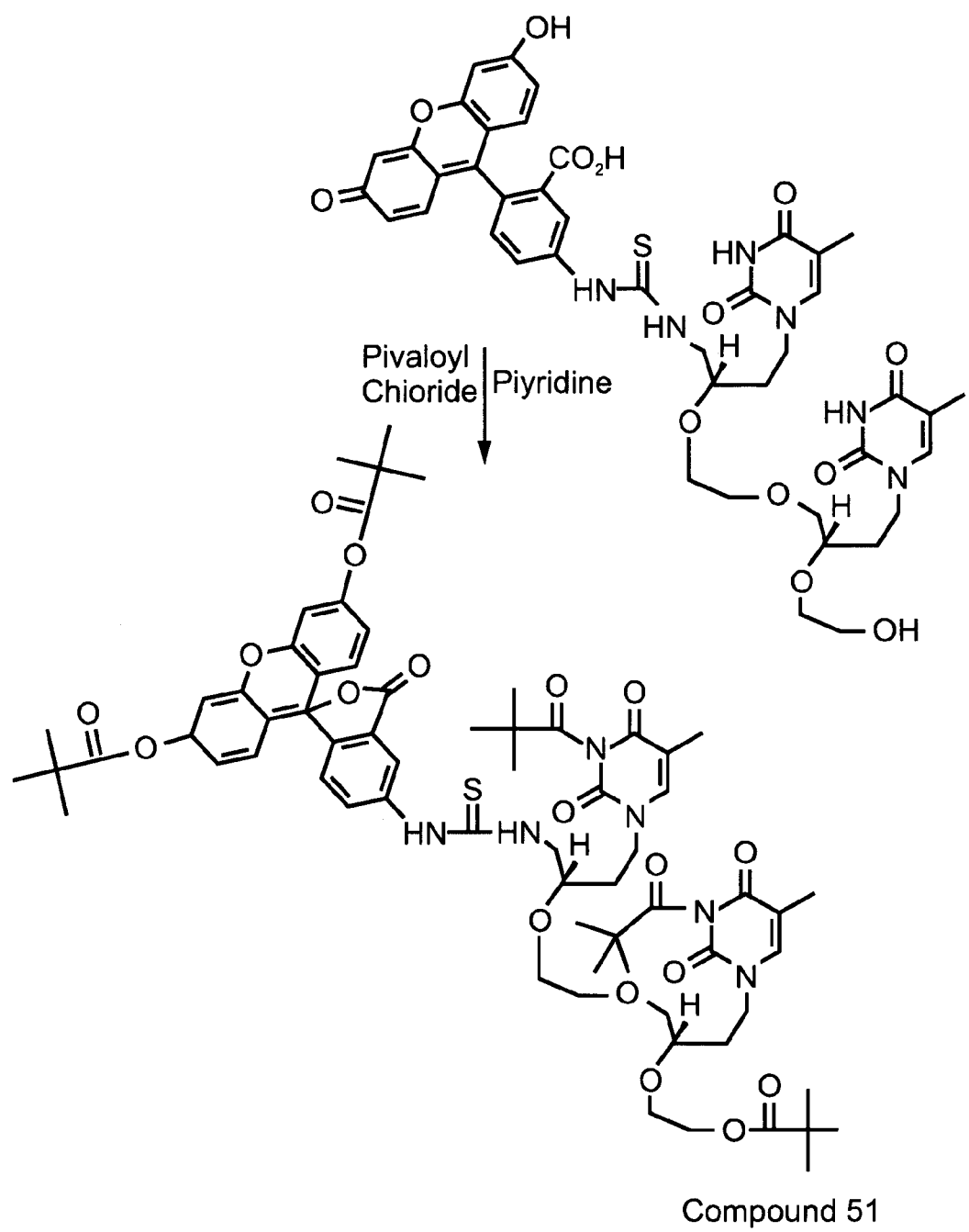
Fig. 8c (ii)

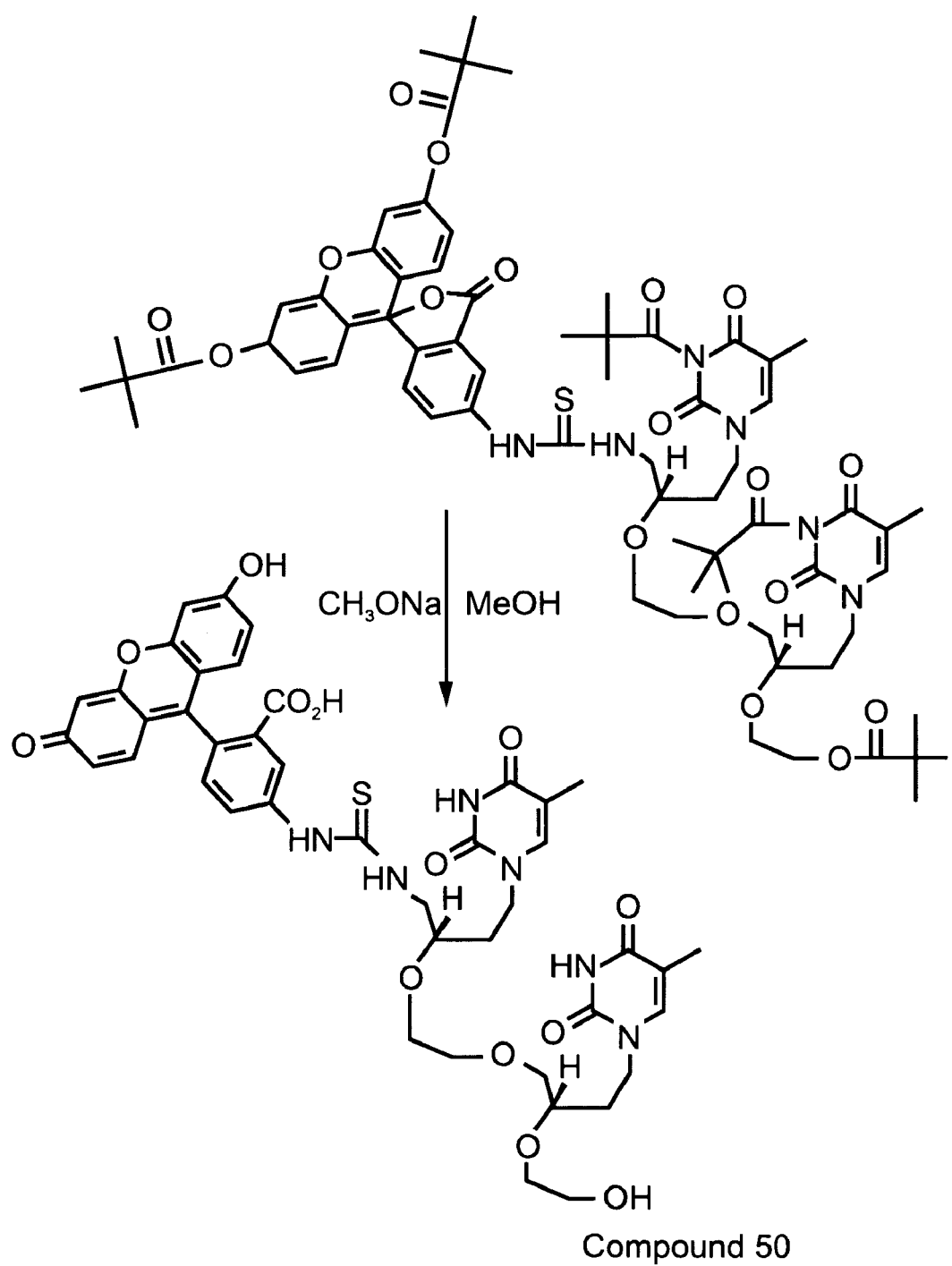
Fig. 8c (iii)

Compound 52 → Compound 53

Compound 52 → Compound 54

Compound 53 → Compound 55

Compound 9 + Compound 55 → Compound 56

Compound 56 → Compound 57

Compound 7 → Compound 58

Compound 58 → Compound 59

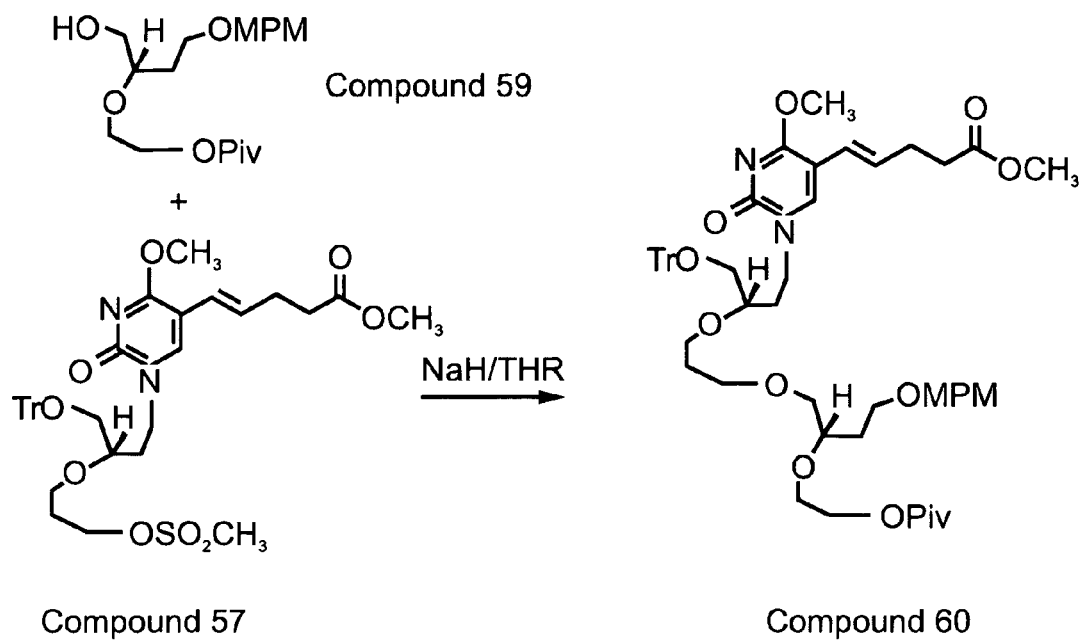
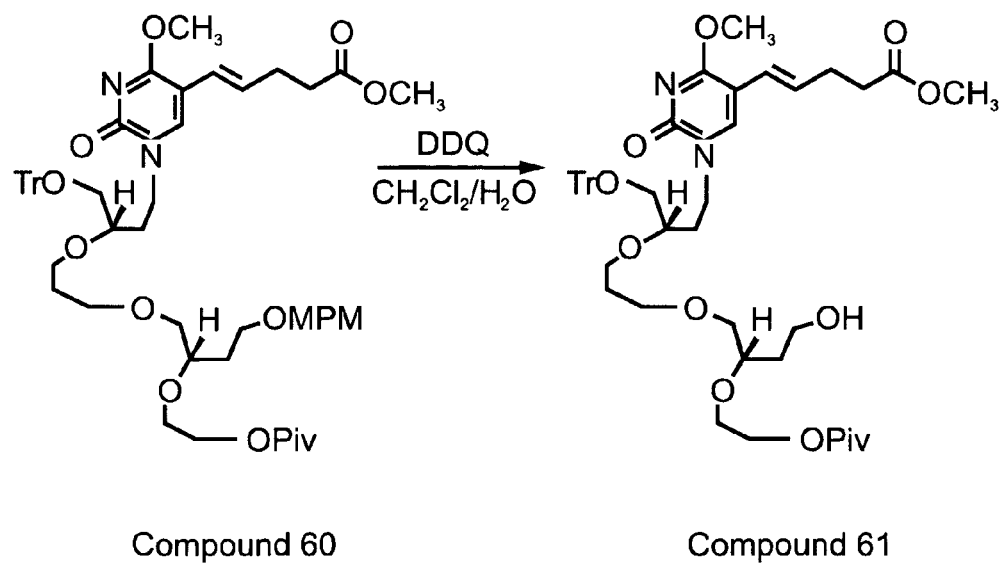
Fig. 10(iii)

Compound 54 + Compound 61

Compound 62

Compound 62

Compound 63

NUCLEIC ACID DERIVATIVES

This application claims the benefit priority from the U.S. Provisional Patent Application No. 60/264,308, filed Jan. 29, 2001.

FIELD AND BACKGROUND OF THE INVENTION

The present invention relates to nucleotide analogs and their derived oligonucleotide analogs, methods of synthesizing both and the use of the oligonucleotide analogs in research, diagnosis and medical applications, e.g., for antisense therapy.

An antisense oligonucleotide (e.g., antisense oligodeoxyribonucleotide) tray bind its target nucleic acid either by Watson-Crick base pairing or Hoogsteen and anti-Hoogsteen base pairing. To this effect see, Thuong and Helene (1993) Sequence specific recognition and modification of double helical DNA by oligonucleotides Angev. Chem. Int. Ed, Engl. 32:666. According to the Watson-Crick base pairing, heterocyclic bases of the antisense oligonucleotide form hydrogen bonds with the heterocyclic bases of target single-stranded nucleic acids (RNA or single-stranded DNA), whereas according to the Hoogsteen base pairing, the heterocyclic bases of the target nucleic acid are double-stranded DNA, wherein a third strand is accommodated in the major groove of the B-form DNA duplex by Hoogsteen and anti-Hoogsteen base pairing to form a triplex structure.

According to both the Watson-Crick and the Hoogsteen base pairing models, antisense oligonucleotides have the potential to regulate gene expression and to disrupt the essential functions of the nucleic acids. Therefore, antisense oligonucleotides have possible uses in modulating a wide range of diseases.

Since the development of effective methods for chemically synthesizing oligonucleotides, these molecules have been extensively used in biochemistry and biological research and have the potential use in medicine, since carefully devised oligonucleotides can be used to control gene expression by regulating levels of transcription, transcripts and/or translation.

Oligodeoxyribonucleotides as long as 100 base pairs (bp) are routinely synthesized by solid phase methods using commercially available, fully automated synthesis machines. The chemical synthesis of oligoribonucleotides, however, is far less routine. Oligoribonucleotides are also much less stable than oligodeoxyribonucleotides, a fact which has contributed to the more prevalent use of oligodeoxyribonucleotides in medical and biological research, directed at, for example, gene therapy or the regulation of transcription or translation levels.

Gene expression involves few distinct and well regulated steps. The first major step of gene expression involves transcription of a messenger RNA (mRNA) which is an RNA sequence complementary to the antisense (i.e., −) DNA strands, or, in other words, identical in sequence to the DNA sense (i.e., +) strand, composing the gene. In eukaryotes, transcription occurs in the cell nucleus.

The second major step of gene expression involves translation of a protein (e.g., enzymes, structural proteins, secreted proteins, gene expression factors, etc.) in which the mRNA interacts with ribosomal RNA complexes (ribosomes) and amino acid activated transfer RNAs (tRNAs) to direct the synthesis of the protein coded for by the mRNA sequence.

Initiation of transcription requires specific recognition of a promoter DNA sequence located upstream to the coding sequence of a gene by an RNA-synthesizing enzyme—RNA polymerase. This recognition is preceded by sequence-specific binding of one or more protein transcription factors to the promoter sequence. Additional proteins which bind at or close to the promoter sequence may upregulate transcription and are known as enhancers. Other proteins which bind to or close to the promoter, but whose binding prohibits action of RNA polymerase, are known as repressors.

There is also evidence that in some cases gene expression is downregulated by endogenous antisense RNA repressors that bind a complementary mRNA transcript and thereby prevent its translation into a functional protein. To this effect see Green et al. (1986) The role of antisense RNA in gene regulation. Ann. Rev. Biochem. 55:569.

Thus, gene expression is typically upregulated by transcription factors and enhancers and downregulated by repressors.

However, in many diseases situation gene expression is impaired. In many cases, such as different types of cancer, for various reasons the expression of a specific endogenous or exogenous (e.g., of a pathogen such as a virus) gene is upregulated. Furthermore, in infectious diseases caused by pathogens such as parasites, bacteria or viruses, the disease progression depends on expression of the pathogen genes, this phenomenon may also be considered as for as the patient is concerned as upregulation of exogenous genes.

Most conventional drugs function by interaction with and modulation of one or more targeted endogenous or exogenous proteins, e.g., enzymes. Such drugs, however, typically are not specific for targeted proteins but interact with other proteins as well. Thus, a relatively large dose of drug must be used to effectively modulate a targeted protein.

Typical daily doses of drugs are from $10^{-5}$–$10^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug could likely be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Given these facts, it would be advantageous if gene expression could be arrested or downmodulated at the transcription level.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription. To this effect see, Thuong and Helene (1993) Sequence specific recognition and modification of double helical DNA by oligonucleotides Angev. Chem. Int. Ed. Engl. 32:666.

At the transcript level, antisense oligonucleotides or analogs that bind target mRNA molecules lead to the enzymatic cleavage of the hybrid by intercellular RNase H. To this effect see Dash et al. (1987) Proc. Natl. Acad. Sci. USA, 84:7896. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. To this effect see Chiang et al. (1991) Antisense oligonucleotides inhibit intercellular adhesion molecule 1 expression by two distinct mechanisms, J. Biol. Chem. 266:18162. As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, as described by Paterson et al. (1977) Proc. Natl. Acad. Sci. USA, 74:4370, a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool. To this effect see Cohen (1992) Oligonucleotide therapeutics. Trends in Biotechnology, 10:87.

For example, several antisense oligonucleotides have been shown to arrest hematopoietic cell proliferation (Szezylik et al. (1991) Selective inhibition of leukemia cell proliferation by BCR-ABL antisense oligodeoxynucleotides. Science 253:562), growth (Calabretta et al. (1991) Normal and leukemic hematopoietic cell manifest differential sensitivity to inhibitory effects of c-myc antisense oligodeoxynucleotides; an in vitro study relevant to bone marrow purging. Proc. Natl. Acad. Sci. USA 88:2351), entry into the S phase of the cell cycle (Heikhila et al. (1987) A c-myc antisense oligodeoxynucleotide inhibits entry into S phase but not progress from G(0) to G(1). Nature, 328:445), reduced survival (Reed et al. (1990) Antisense mediated inhibition of BCL2 prooncogene expression and leukemic cell growth and survival: comparison of phosphodiester and phosphorothioate oligodeoxynucleotides. Cancer Res. 50;6565) and prevent receptor mediated responses (Burch and Mahan (1991) Oligodeoxynucleotides antisense to the interleukin I receptor m RNA block the effects of interleukin I in cultured murine and human fibroblasts and in mice. J. Clin. Invest. 88:1190). For use of antisense oligonucleotides as antiviral agents the reader is referred to Agrawal (1992) Antisense oligonucleotides as antiviral agents. TIBTECH 10:152.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters, see, Uhlmann et al. (1990) Chem. Rev. 90:544.

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success. To this effect see Brand (2001) Topical and transdermal delivery of antisense oligonucleotides. Curr Opin Mol Ther (3):244–8.

Oligonucleotides can be modified either in the base, the sugar or the phosphate moiety. These modifications include the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, α-anomeric bridges and borane derivatives. For further details the reader is referred to Cook (1991) Medicinal chemistry of antisense oligonucleotides—future opportunities. Anti-Cancer Drug Design 6:585.

Extensive efforts have also been performed in the field of predicting the binding affinities of antisense oligonucleotides to their target sequence. To this effect see Walton et al. (1999) Prediction of antisense oligonucleotide binding affinity to a structured RNA target. Biotechnol Bioeng 65(1):1–9; Jayaraman et al. (2001) Rational selection and quantitative evaluation of antisense oligonucleotides. Biochim Biophys Acta 1520(2):105–14; and Matveeva et al. (1998) Prediction of antisense oligonucleotide efficacy by in vitro methods. *Nature Biotechnology* 16, 1374–1375.

International patent application WO 86/05518 broadly claims a polymeric composition effective to bind to a single-stranded polynucleotide containing a target sequence of bases. The composition is said to comprise non-homopolymeric, substantially stereoregular polymer molecules of the form;

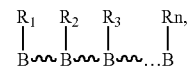

where R1–Rn are recognition moieties selected from purine, purine-like, pyrimidine, and pyrimidine like heterocycles effective to bind by Watson/Crick pairing to corresponding, in-sequence bases in the target sequence; n is such that the total number of Watson/Crick hydrogen bonds formed between a polymer molecule and target sequence is at least about 15; B~B are backbone moieties joined predominantly by chemically stable, substantially uncharged, predominantly chiral linkages; the backbone moiety length ranges from 5 to 7 atoms if the backbone moieties have a cyclic structure, and ranges from 4 to 6 atoms if the backbone moieties have an acyclic structure; and the backbone moieties support the recognition moieties at position which allow Watson-Crick base pairing between the recognition moieties and the corresponding, in-sequence bases of the target sequence.

According to WO 86/05518, the recognition moieties are various natural nucleobases and nucleobase-analogs and the backbone moieties are either cyclic backbone moieties comprising furan or morpholine rings or acyclic backbone moieties of the following forms:

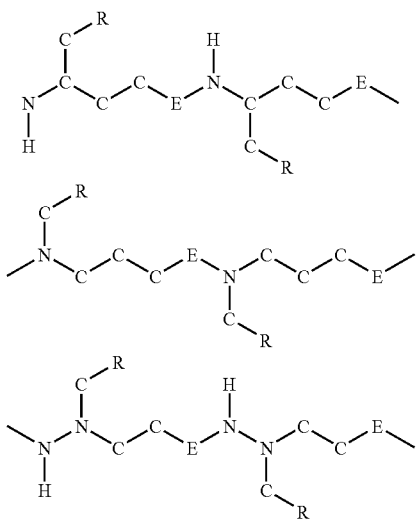

where E is —CO— or —$SO_2$—. The specification of the application provides general descriptions for the synthesis of subunits, for backbone coupling reactions, and for polymer assembly strategies. Although WO 86/05518 indicates that the claimed polymer compositions can bind target sequences and, as a result, have possible diagnostic and therapeutic applications, the application contains no data relating to the binding capabilities of a claimed polymer.

International patent application WO 86/05519 describes diagnostic reagents and systems that comprise polymers described in WO 86/05518, attached to a solid support.

International patent application WO 89/12060 describes various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—$SO_2$—). However, this application provides no experimental data supporting the specific binding of an oligonucleotide analog to a target oligonucleotide.

Nielsen et al. (1991) Science 254:1497, and International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. To this effect of PNA heterohybrids see Biotechnology research news (1993) Can DNA mimics improve on the real thing? Science 262:1647.

PNA oligomers can be synthesized from the four protected monomers thymine, cytosine, adenine and guanine by Merrifield solid-phase peptide synthesis. In order to increase solubility in water and to prevent aggregation, a lysine amide group is placed at the C-terminal.

However, there are some major drawbacks associated with the PNA approach. One drawback is that, at least in test-tube cultures, PNA molecules do not penetrate through cell membranes, not even to the limited extent natural short DNA and RNA segments do. The second drawback is side effects which are encountered with toxicity. Because PNAs bind so strongly to target sequences they lack the specificity of their natural counterparts and end up binding not just to target sequences but also to other strands of DNA, RNA or even proteins, incapacitating the cell in unforeseen ways.

U.S. Pat. No. 5,908,845 to Segev describes nucleic acid mimetics consisting of a polyether backbone, bearing a plurality of ligands, such as nucleobases or analogs thereof, which are able to hybridize to complementary DNA or RNA sequences. According to U.S. Pat. No. 5,908,845, the oligonucleotide mimetics are of the following optional forms:

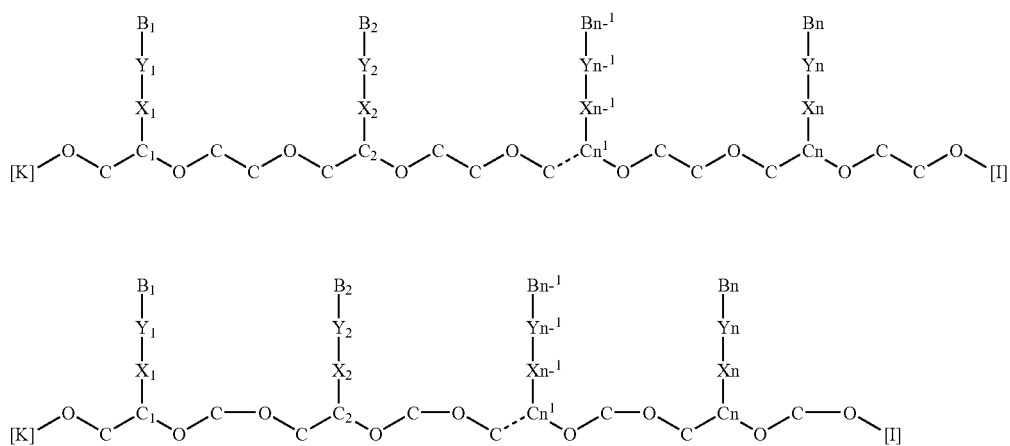

where n is an integer greater than one, each of B1–Bn is independently a chemical functionality group, such as, but not limited to, a naturally occurring nucleobase, a nucleobase binding group or a DNA interchelator, each of Y1–Yn is a first linker group, each of X1–Xn is a second linker group, C1–Cn are chiral carbon atoms and [K] and [I] are a first and second exoconjugates.

According to the teachings of U.S. Pat. No. 5,908,845, poly(ethylene glycol) (PEG) is a preferred polyether backbone for polyether nucleic acids. Poly(ethylene glycol) (PEG) is one of the best biocompatible polymers known, which possesses an array of useful properties, such as a wide range of solubility properties in both organic and aqueous media (Mutter et al. (1979) The Peptides Academic Press, 285), lack of toxicity and immunogenicity (Dreborg et al. (1990), Crit. Rev, Ther. Drug Carrier Syst. 6:315), nonbiocontact. For further information concerning the biocompatability of PEG, the reader is referred to Zalipski (1995) Functionalized poly(ethylene glycol) for preparation of biologically relevant conjugates, Bioconjugate Chem. 6:150.

U.S. patent application Ser. No. 09/411,862 and WO 01/16365, both by Segev, also describe nucleic acid mimetics. The nucleic acids mimetics described therein are analogs of the nucleic acid mimetics described in U.S. Pat. No. 5,908,845 and are consisting of a poly(ether-thioether), a poly(ether-sulfone) or a poly(ether-sulfoxide) backbone, each bearing a plurality of ligands, such as nucleobases or analogs thereof, which are capable of hybridizing with complementary DNA or RNA sequences.

According to U.S. patent application Ser. No. 09/411,862 and WO 01/16365, the oligonucleotide mimetics are of the following optional forms:

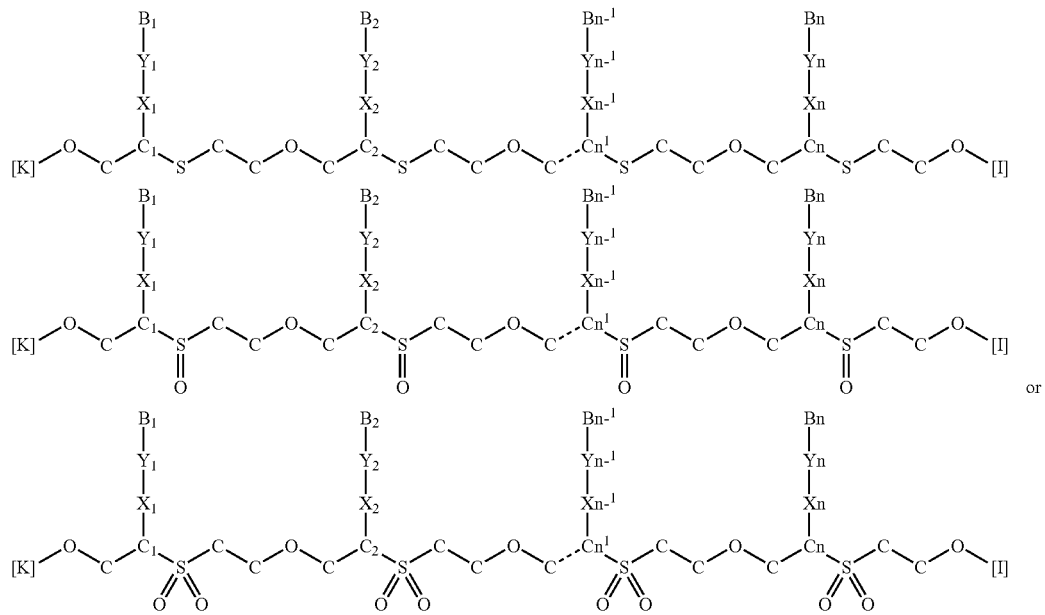

degradability, and ease of excretion from living organisms (Yamaoka et al. (1994) J. Pharm. Sci. 83:601).

During the last two decades PEG was used extensively as a covalent modifier of a variety of substrates, producing conjugates which combine some of the properties of both the starting substrate and the polymer. See, Harris, J. M. (1992), Poly(ethylene Glycol) Chemistry, Plenum Press, New York. The overwhelming majority of work in this area was prompted by a desire to alter one or more properties of a substrate of interest to make it suitable for a particular biological application. As the arsenal of PEG conjugates and their applications have increased it has become apparent that many undesirable effects triggered in vivo by various biological recognition mechanisms can be minimized by covalent modifications with PEG.

For example, using PEG conjugates, immunogenicity and antigenicity of proteins can be decreased. To this effect see U.S. Pat. No. 4,179,337 to Davis et al. Thrombogenicity as well as cell and protein adherence can be reduced in the case of PEG-grafted surfaces. To this effect see Merrill (1992) Poly(ethylene Glycol) Chemistry, page 199, Plenum Press, New York. These beneficial properties conveyed by PEG are of enormous importance for any system requiring blood wherein the variables' limitations are similar to the limitations cited in U.S. Pat. No. 5,908,845, as described hereinabove.

However, the oligonucleotide mimetics described in U.S. Pat. No. 5,908,845 and in U.S. patent application Ser. No. 09/411,862 and WO 01/16365 are all based on an acyclic polyether or polyether derivative backbone. The specification of these reference includes molecular models demonstrating the hybridization of a polyether nucleic acid compound having eleven atoms between adjacent B functionality groups, according to U.S. Pat. No. 5,908,845, with natural tetra-adenine-ssDNA. However, it was later rationalized that an actual hybridization between these polyether nucleic acid derivatives and a single-stranded DNA is expected to be less favorable than what was anticipated, since these acyclic polyethers include eleven free rotating bonds, while in a natural oligodeoxyribonucleotide there are only six bonds that are freely rotatable. The other five bonds in a natural oligodeoxyribonucleotide are located in a cyclic structure and hence have no free rotations. This incompatibility between the number of free rotational bonds is a major drawback since it may reduce the ability to form stable interactions between the functionality groups in a polyether nucleic acid and natural nucleic acids.

There is thus a widely recognized need for, and it would be highly advantageous to have, oligonucleotide analogs devoid of the above drawbacks and which are further characterized by (i) ease of synthetic procedure and proven synthetic efficiency; and (ii) a rigidity that is compatible with the structure of natural nucleic acids, and which are further characterized by properties common to the above described polyether nucleic acids, such as (i) sufficient specificity in binding to target sequences; (ii) solubility in water, (iii) stability against intra- and extracellular nucleases; (v) capability of penetrating through cell membranes; and (v) when used to treat an organism, low toxicity, properties that collectively render an oligonucleotide analog highly suitable as an antisense therapeutic drug.

SUMMARY OF THE INVENTION

According to the present invention, there are provided nucleotide analogs and oligonucleotide analogs containing same, methods of preparing same and uses of the oligonucleotide analogs in research, diagnosis and medical applications, such as antisense therapy. The oligonucleotide analogs of the present invention include cyclic moieties which enable the formation of stable hybrids with natural nucleic acids and can therefore be efficiently used in a wide variety of applications and, in particular in antisense therapy.

According to one aspect of the present invention, there is provided a compound comprising a backbone having a plurality of chiral carbon atoms, the backbone bearing a plurality of ligands each being individually bound to a chiral carbon atom of the plurality of chiral carbon atoms, the ligands including one or more pair(s) of adjacent ligands each containing a moiety selected from the group consisting of a naturally occurring nucleobase and a nucleobase binding group, wherein moieties of the one or more pair(s) are directly linked to one another via a linker chain.

According to further features in preferred embodiments of the invention described below, the backbone comprises a polyether and/or a polyether derivative.

According to still further features in the described preferred embodiments the polyether comprises poly(ethylene glycol).

According to still further features in the described preferred embodiments the polyether derivative is selected from the group consisting of poly(ether-thioether), poly(ether-sulfone) and poly(ether-sulfoxide).

According to still further features in the described preferred embodiments the backbone is selected from the group consisting of a thiophosphonate DNA backbone, a phosphoramidate backbone, a morpholino phosphoramidate backbone and a methyl phosphonate backbone.

According to still further features in the described preferred embodiments the chiral carbon atoms are separated from one another in the backbone by from four to six intervening atoms.

According to still further features in the described preferred embodiments the linker chain comprises between four and fourteen atoms.

According to still further features in the described preferred embodiments the linker chain has a formula:

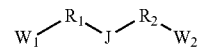

wherein R1 and R2 are each independently selected from the group consisting of a methylene group, a substituted or unsubstituted saturated alkylene chain and a substituted or unsubstituted unsaturated alkylene chain, W1 and W2 are each independently selected from the group consisting of a single bond, a double bond and a triple bond and J is selected from the group consisting of alkyl, aryl, amide, amine, ether, ester, carbonyl, thiocarbonyl, phosphate, carbamate, thioether, disulfide, sulfone and sulfoxide.

According to another aspect of the present invention, there is provided a process of preparing the compound described hereinabove, the process comprising obtaining monomers, preferably monomers having an ether moiety, each of the monomers including one or more chiral carbon atom having a functionality group linked thereto, the functionality group being selected from the group consisting of a protected or unprotected naturally occurring nucleobase and a protected or unprotected nucleobase binding group. The process further comprises obtaining dimers, preferably dimers having two ether moieties as defined hereinabove, each of the dimers including at least two chiral carbon atoms, each of the chiral carbon atoms having a functionality group as described hereinabove, linked thereto, the dimers further including a linker chain connecting the functionality groups and condensing the monomers and the dimers therebetween and one with another, so as to obtain a polymer of condensed monomers and dimers.

According to yet another aspect of the present invention, there is provided another process of preparing the compound described hereinabove, the process comprising obtaining the monomers find dimers described hereinabove, attaching a first monomer of tile monomers or a first dimer of the dimers to a solid support and sequentially condensing the monomers and the dimers in a predetermined sequence to the first monomer or the first dimer, so as to obtain a polymer of condensed monomers and dimers.

According to further features in preferred embodiments of the invention described below, one or more of the nucleobases is a protected nucleobase and the process further comprising deprotecting the one or more protected nucleobase(s).

According to still another aspect of the present invention, there is provided a process of sequence specific hybridization, the process comprising contacting a double stranded polynucleotide with the compound described hereinabove, such that the compound binds in a sequence specific manner to one strand of the polynucleotide, thereby displacing the other strand.

According to an additional aspect of the present invention there is provided a process of sequence specific hybridization, the process comprising contacting a single-stranded polynucleotide with the compound described hereinabove, such that the compound binds in a sequence specific manner to the polynucleotide.

According to yet an additional aspect of the present invention there is provided a process of modulating the expression of a gene in an organism, the process comprising administering to the organism the compound described hereinabove, such that the compound binds in a sequence specific manner DNA or RNA deriving from the gene.

According to further features in preferred embodiments of the invention described below, the modulation includes inhibiting transcription of the gene.

According to still further features in the described preferred embodiments the modulation includes inhibiting replication of the gene.

According to still further features in the described preferred embodiments the modulation includes inhibiting translation of the RNA of the gene.

According to still an additional aspect of the present invention there is provided a process of treating a condition associated with undesired protein production in an organism, the process comprising contacting the organism with an effective amount of the compound described hereinabove, the compound specifically binds with DNA or RNA deriving from a gene controlling the protein production.

According to a further aspect of the present invention there is provided a process of inducing degradation of DNA or RNA in cells of an organism, the process comprising administering to the organism the compound described hereinabove, the compound specifically binds to the DNA or RNA.

According to yet a further aspect of the present invention there is provided a process of killing cells or viruses, the process comprising contacting the cells or viruses with the compound described hereinabove, the compound specifically binds to a portion of the genome or to RNA derived therefrom of the cells or viruses.

According to still a further aspect of the present invention, there is provided a compound having a formula:

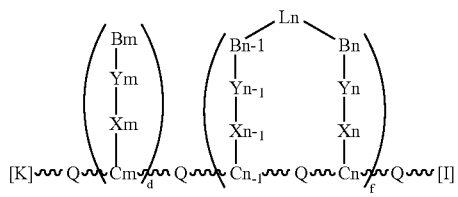

or

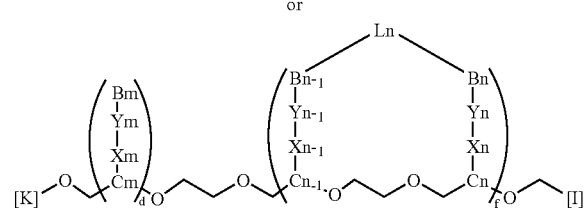

wherein m and n are each independently an integer, m≠n, m≠n-1, d is an integer which equals to or greater than 0, f is an integer greater than 0, L is a linker chain as described hereinabove, each of Bm, Bn-1 and Bn is a chemical functionality group independently selected from the group consisting of a naturally occurring nucleobase and a nucleobase binding group, each of Ym, Yn-1 and Yn is a first linker group, each of Xm, Xn-1 and Xn is a second linker group, Cm, Cn-1 and Cn are chiral carbon atoms, Q is a backbone as described hereinabove, bearing the Cm, Cn-1 and Cn chiral carbon atoms, and [K] and [I] are optional first and second exoconjugates.

According to further feature in preferred embodiments of the invention described below, the compound has the formula;

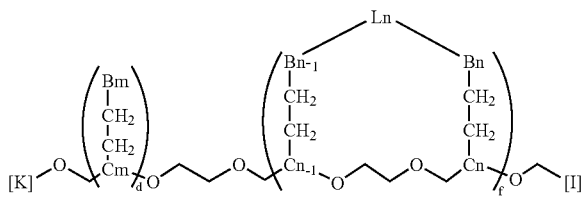

According to still further feature in the described preferred embodiments, the compound has the formula:

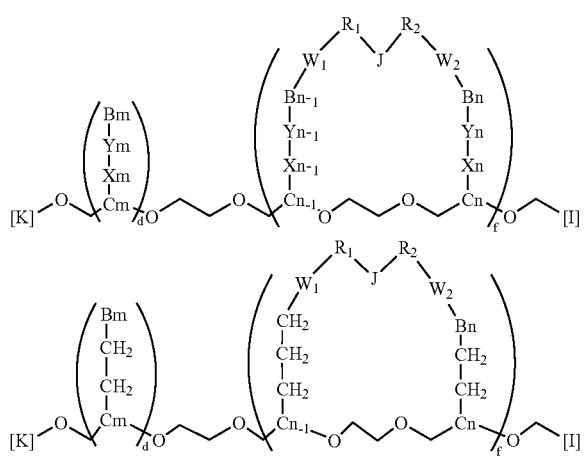

wherein R1, R2, W1, W2, and J are as defined hereinabove.

According to still further features in the described preferred embodiments, m percents of the chiral carbons are in an S configuration, wherein m is selected from the group consisting of 90–95%, 96–98%, about 99% and greater than 99%.

According to still further features in the described preferred embodiments, the compounds described hereinabove further comprising one or more reporter group(s) linked to the backbone.

According to another aspect of the present invention, there are provided pharmaceutical compositions comprising, as an active ingredient, the compounds described hereinabove and a pharmaceutically acceptable carrier.

According to yet another aspect of the present invention there is provided a compound having the formula:

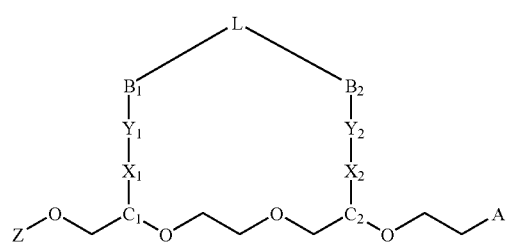

wherein L is a linker chain as described hereinabove, each of B1 and B2 is a chemical functionality group selected from the group consisting of a protected or unprotected naturally occurring nucleobase and a protected or unprotected nucleobase binding group, each of Y1 and Y2 is a first linker group, each of X1 and X2 is a second linker group, C1 and C2 are chiral carbon atoms, Z is a first protecting group and A is a leaving group.

According to further features in preferred embodiments in the invention described below, should one or more of the nucleobase include an amino group, the amino group is protected by a second protecting group P.

According to still further features in the described preferred embodiments the compound has a formula:

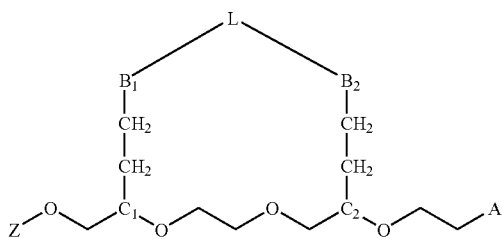

According to still further features in the described preferred embodiments the compound has a formula:

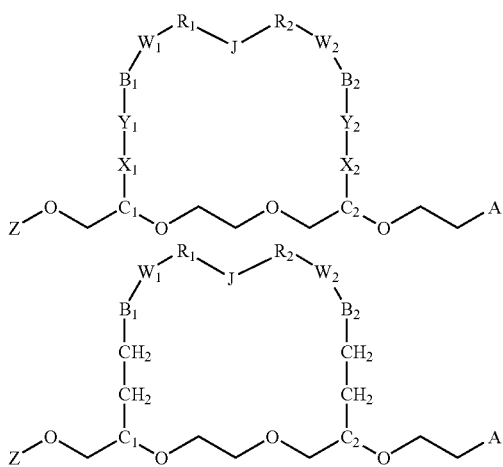

wherein R1, R2, W1, W2 and J are as defined hereinabove.

According to still further features in the described preferred embodiments the compound has a formula:

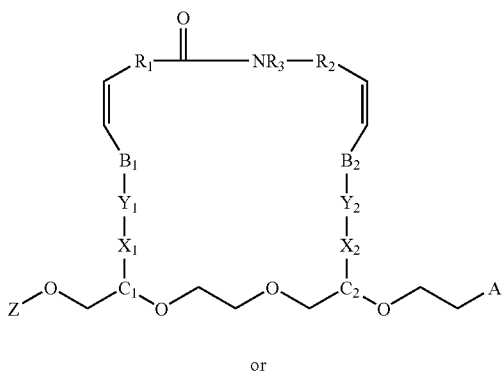

or

-continued

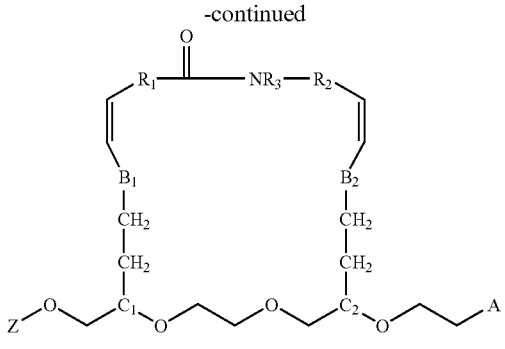

wherein R1 and R2, are as defined hereinabove and R3 is selected from the group consisting of hydrogen, methyl and alkyl.

According to still another aspect of the present invention, there is provided a process of preparing the dimeric compound described hereinabove, the process comprising obtaining a first ethylene glycol moiety including a first chiral carbon atom, the first chiral carbon atom having a first functionality group linked thereto, the first functionality group being selected from the group consisting of a naturally occurring nucleobase and a nucleobase binding group and bearing a first linker arm terminating with a first chemically reactive group, the first chiral carbon atom further having a protecting group Z attached thereto, condensing to the first ethylene glycol moiety a second ethylene glycol moiety including a second chiral carbon atom, thereby obtaining a diethylene glycol moiety including the first chiral carbon atom having the first functionality group and the protecting group linked thereto and a second chiral carbon atom, reacting the diethylene glycol moiety with a second functionality group, the second functionality group being selected from the group consisting of a naturally occurring nucleobase and a nucleobase binding group and bearing a second linker arm terminating with a second chemically reactive group, thereby obtaining a diethylene glycol moiety including the first chiral carbon atom having the first functionality group linked thereto and the second chiral carbon atom having the second functionality group linked thereto, condensing the first linker arm and the second linker arm, thereby obtaining a diethylene glycol moiety including the first and the second chiral carbon atoms having the first and the second functionality groups linked thereto, the first and the second functionality groups being covalently attached therebetween via a linker chain, and converting the resulting diethylene glycol moiety, so as to obtain the diethylene glycol moiety having a leaving group A attached to the second chiral carbon atom.

According to, an additional aspect of the present invention, there is provided a compound having the formula:

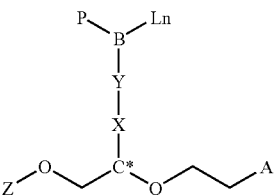

wherein B is a chemical functionality group selected from the group consisting of a naturally occurring nucleobase and a nucleobase binding group, Y is a first linker group, X is a second linker group, C* is a chiral carbon atom, Z is a first protecting group, P is a second protecting group, A is a leaving group, and La is a linker arm.

According to further features in preferred embodiments of the invention described below, the L linker arm has a formula:

Wa-Ra-Ja wherein Ra is selected from the group consisting of a methylene group, a substituted or unsubstituted saturated alkylene chain and a substituted or unsubstituted unsaturated alkylene chain, Wa is selected from the group consisting of a single bond, a double bond and a triple bond and Ja is a chemically reactive group capable of participating in a condensation reaction.

According to still further features in the described preferred embodiments the Ja chemically reactive group is selected from the group consisting of an electrophilic group and a nucleophilic group.

According to still further features in the described preferred embodiments Ra is a C2–C4 alkylene chain, Wa is a double bond and Ja is selected from the group consisting of carboxylic acid, ester, acyl halide, amino, hydroxyl, alkoxyl, aryloxyl, thioester, thiol, thioalkyl and amide.

According to yet an additional aspect of the present invention there is provided a compound having the formula:

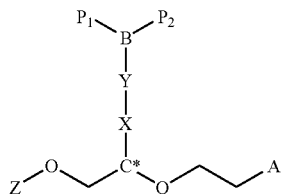

wherein B is a chemical functionality group selected from the group consisting of a naturally occurring nucleobase and a nucleobase binding group, Y is a first linker group, X is a second linker group, C* is a chiral carbon atom, Z is a first protecting group, each of P1 and P2 is a second protecting group and A is a leaving group.

According to still further features in the described preferred embodiments the Z protecting group is selected from the group consisting of a dimethoxytrityl group, a trityl group, a monomethoxytrityl group, a silyl group and a group that is removable under acidic or basic conditions.

According to still further features in the described preferred embodiments the A leaving group is selected from the group consisting of a halide group, a sulfonate group, an ammonium derivative and a radical moiety that could be replaced by SN1 or SN2 mechanisms.

According to still further features in the described preferred embodiments each of the P, P1 and P2 second protecting group is selected from the group consisting of a methylbenzylether group, a methoxybenzylether group, a benzamido group, an isobutyramido group, a t-butoxycarbonyl group, a benzyloxymethyl, a fluorenylmethyloxycarbonyl group, a methylpyrrolidone and an acid labile group which is not cleaved by reagents that cleave the Z protecting group.

According to still further features in the described preferred embodiments each of the X-Y, X1-Y1, X2-Y2, Ym-Xm, Yn-1-Xn-1 and Yn-Xn linker groups is a single bond.

According to still further features in the described preferred embodiments each of the Y, Y1, Y2, Ym, Yn-1 and Yn first linker groups is independently selected from the group consisting of an alkyl group, a phosphate group, a (C2–C4) alkylene chain, a (C2–C4) substituted alkylene chain and a single bond.

According to still further features in the described preferred embodiments each of the Y, Y1, Y2, Ym, Yn-1 and Yn first linker groups is independently selected from the group consisting of a methylene group and a C-alkanoyl group.

According to still further features in the described preferred embodiments each of the X, X1, X2, Xm, Xn-1 and Xn second linker groups is independently selected from the group consisting of a methylene group, an alkyl group, an amino group, an amido group, a sulfur atom, an oxygen atom, a selenium atom, a C-alkanoyl group, a phosphate derivative group, a carbonyl group and a single bond.

According to still further features in the described preferred embodiments the compounds described hereinabove further comprise one or more reporter molecule(s) linked thereto.

The present invention successfully addresses the shortcomings of the presently known configurations by providing a polynucleotide analog characterized by (i) ease of synthetic procedure and proven synthetic efficiency and (ii) a rigidity that is compatible with the structure of natural nucleic acids, and which is further characterized by properties common to the above described polyether nucleic acids, such as (i) sufficient specificity is binding its target sequence; (ii) solubility in water, (iii) stability against intra- and extracellular nucleases; (iv) capability of penetrating through the cell membrane; and (v) when used to treat an organism, low toxicity, properties collectively rendering the polynucleotide analog of the present invention highly suitable as an antisense therapeutic drug.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
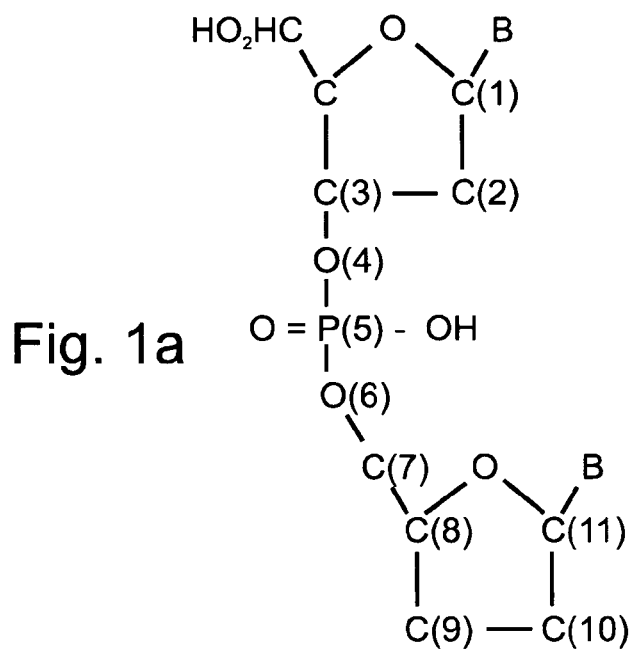
FIGS. 1a–b depict the eleven atoms separating nucleobases on (a) native DNA (FIG. 1a) and (b) an oligonucleotide compound having a polyether backbone according to a preferred embodiment of the present invention (FIG. 1b)

The present invention is of oligomeric compounds which can be used as oligonucleotide analogs that bind to complementary DNA and RNA sequences. Specifically, the oligomeric compounds of the present invention include naturally occurring nucleobases (i.e., native nucleobase, e.g., A, C, G, T, U) or other nucleobase binding groups (i.e., a moiety which is not a native nucleobase, yet as native nucleobases may form hydrogen bonds with nucleobases in a way similar to native nucleobases, e.g., inosine, thiouracil, bromothymine, azaguanines, azaadenines, 5-methylcytosine etc., also referred herein as nucleobase analog) covalently bound to a backbone, which can be used as oligonucleotide analogs in research, diagnosis and in a variety of medical applications such as, but not limited to, antisense therapy. The oligonucleotide analogs of the present invention include cyclic moieties that enhance the formation of stable hybrids thereof with natural nucleic acids by providing the oligonucleotide analog with a rigidity that is compatible with the structure of natural nucleic acids upon pairing. The oligonucleotide analogs of the present invention are easily and efficiently synthesized and are further characterized by the other criteria for selecting antisense oligonucleotide analogs listed in the Background section hereinabove, including, but not limited to, (i) ease of synthetic procedure and proven synthetic efficiency and (ii) a rigidity that is compatible with the structure of natural nucleic acids, and which is further characterized by properties common to the above described polyether nucleic acids, such as (i) sufficient specificity in binding its target sequence; (ii) solubility in water: (iii) stability against intra- and extracellular nucleases; (iv) capability of penetrating through the cell membrane; and (v) when used to treat an organism, low toxicity, properties collectively rendering the polynucleotide analog of the present invention highly suitable as an antisense therapeutic drug.

The synthesis, structure and mode of operation of the nucleotide analogs and the oligonucleotide antisense analogs according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention provides a new class of backbone DNA compounds, that complementary bind to single-stranded (ss) and/or double-stranded (ds) DNA and/or RNA molecules. These compounds are herein referred to as oligonucleotide analogs or as nucleic acid derivative compounds. The compounds of the present invention generally include a backbone and chemical functionality groups, at least some of which are adjacent groups that are capable of forming suitable hydrogen bonds in a complementary manner with ssDNA and RNA and are directly linked to one another via a linker chain. The compounds of the present invention may further include non-linked adjacent chemical functionality groups having the same properties as described hereinabove. Representative chemical functionality groups include either the five naturally occurring DNA and RNA nucleobases, i.e., thymine, adenine, cytosine, uracil or guanine, or modified bases, such as, but not limited to, inosine, thiouracil, bromothymine, azaguanines, azaadenines, 5-methylcytosine, modifications of cytosine such as—2,4-diazaphenoxazine-3-one, and modification of uracil at C-5 position like with thiazole group, both modifications are for increasing the melting temperature (Tm) of the hybrid with DNA or RNA targets, which are typically attached to the backbone via a suitable linker moiety made of one or more linker groups.

According to a preferred embodiment of the present invention, the linker chain which directly connects two adjacent functionality groups includes between four and fourteen atoms, more preferably between eight and twelve atoms.

The linker chain preferably includes a hydrocarbon chain, which can be interrupted by an additional linking group such as, but not limited to an amide, an amine, an ether, an ester, a carbonyl, a thiocarbonyl, a phosphate, a carbamate, a thioether, a disulfide, a sulfone, cl sulfoxide and any other suitable organic and/or inorganic group.

As used herein, the term "amide" includes a "—NR'—C(=O)—" group, where R' is hydrogen or an alkyl group.

As used herein, the term "alkyl" includes a saturated aliphatic hydrocarbon including straight chain and branched chain groups.

As used herein, the term "amine" includes a "—NR'R"—" group, where R' and R' are each hydrogen or an alkyl group as defined hereinabove.

The term "ether" includes a "—C—O—" group.

The term "carbonyl" includes a "—C=O—" group.

The term "thiocarbonyl" includes a "—C=S—" group.

The term "phosphate" includes a "—O—P(=O)(OR')—O—" group, where R' is a s defined hereinabove.

The term "carbamate" includes a "—R'N—C(=O)—O—" group, where R' is as defined hereinabove.

The term "thioether" includes a "—C—S—" group.

The term "sulfide" includes a "—S—S—" group.

The term "sulfone" includes a "—SO$_2$—" group.

The term "sulfoxide" includes a "—S=O—" group.

The linker chain is typically connected to the nucleobases or nucleobase analogs via a single bond, a double bond or a triple bond.

Thus, a preferred linker chain according to the present invention has the general formula I:

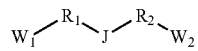

wherein R1 and R2 are each a hydrocarbon chain such as, but not limited to, a methylene group, a substituted or unsubstituted saturated alkylene chain and a substituted or unsubstituted unsaturated alkylene chain; W1 and W2 art each independently a single bond, a double bond or a triple bond; and J is a linking group such as, but not limited to, an alkyl, an aryl, an amide, an amine, an ether, an ester, a carbonyl, a thiocarbonyl, a phosphate, a carbamate, a thioether, a disulfide, a sulfone and a sulfoxide.

As used herein, the phrase "methylene group" includes a "—CH$_2$—" group.

The phrase "saturated alkylene chain" includes a chain of methylene groups, as this term is defined hereinabove. Preferably, an alkylene chain according to the present invention includes from two to eight methylene chains. More preferably, the alkylene chain includes from two to four methylene groups and is also referred to herein as a C2–C4 alkylene chain.

The phrase "unsaturated alkylene chain" includes an alkylene chain as described hereinabove, which further includes one or more unsaturated hydrocarbon groups such as, but not limited to, a vinyl group, —C=C—, or an acetylene group, —C≡C—.

As used herein, the term "aryl" includes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl.

By directly connecting two adjacent functionality groups that are covalently attached to the backbone, the linker chain forms a cyclic dimeric moiety that is compatible with the structure of native DNA, as is described hereinabove and is therefore advantageous over the presently known antisense oligonucleotide analogs, which often lack such compatibility.

In one embodiment of the invention, the nucleic acid derivative compound has the general formula II:

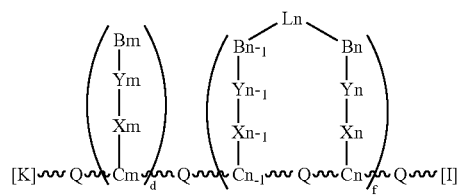

wherein, m and n are each independently an integer, m≠n, m≠n-1, d is an integer which equals to or greater than 0, f is an integer greater than 0, L is a linker chain as described hereinabove, each of Bm, Bn-1 and Bn is a chemical functionality group independently selected from the group consisting of a naturally occurring nucleobase and a nucleobase binding group, each of Ym, Yn-1 and Yn is a first linker group, each of Xm, Xn-1 and Xn is a second linker group, Cm, Cn-1 and Cn are chiral carbon atoms, Q is a backbone as described hereinabove, bearing the Cm, Cn-1 and Cn chiral carbon atoms, and [K] and [I] are optional first and second exoconjugates.

Thus, according to the teachings of the present invention, the nucleic acid derivative includes a plurality of m and n ligands. Preferably, the sum of n and m, which describes the number of chiral atoms within the backbone to which these ligands are attached, ranges between 4 and 50, more preferably it ranges between 8 to 30 and most preferably it ranges between 12 and 22. Further preferably, the nucleic acid derivative of the present invention includes "f" pairs of functionality groups that are connected therebetween by a linker chain and thus form a cyclic dimeric moiety, and optionally, "d" functionality groups that are covalently attached solely to the backbone. Still further preferably, d is an integer which equals to or greater than 1, more preferably d ranges between 2 and 50 and, most preferably, d ranges between 10 and 30 and f ranges between 2 and 50, more preferably between 2 and 20 and, most preferably, between 2 and 4.

According to a preferred embodiment of the invention, the chemical functionality groups B (see, formula II) are naturally occurring or analog nucleobases attached to the backbone in a predetermined and selected order, forming a sequence. Preferably the nucleobases are attached to Y via the position found in nature, i.e., position 9 for purities (e.g., adenine and guanine), and position 1 for pyrimidines (e.g., uracyl and cytosine).

In addition, for various purposes, some of the chemical functionality groups B may be hydroxyl, amine, amides thiol, carboxylic derivative, (C1–C3) alkanoyl, aryl, heterocycle, a chelating agent (e.g., EDTA, EGTA), a diol group such as a vicinal diol group, a triol group or any other chemical functionality group that enhances the Pi stacking of the bases by the oligonucleotide analog, as is described, for example, by Puri et al Tetrahedron, (1997) 53:10409.

As used herein, the term "hydroxyl" refers to a "—OH" group.

The term "thiol" refers to a "—SH" group.

The term "carboxylic derivative" includes a "—C(=O)—R'''" group, where R''' is, for example, halogen atom (e.g., F, Cl , Br, I), alkoxyl or hydroxyl.

The term "(C1–C3) alkanoyl" includes a primary, secondary and tertiary carbon atom.

The term "heterocycle" includes a monocyclic or fused ring group having in the ring(s) one or more atoms such as nitrogen, oxygen and sulfur. The rings may also have one or more double bonds. However, the rings do not have a completely conjugated pi-electron system.

The terms "diol" and "triol" include compounds having two and three hydroxyl group, respectively. The hydroxyl groups can be vicinal or geminal.

In order to improve the binding of the oligonucleotide compound of the present invention both to double-stranded and single-stranded DNA, some B functionality groups may be a DNA intercalator such as, but not limited to, an anthraquinone group and the like.

Furthermore, one or more of the functionality groups B may include a reporter molecule such as, for example, a fluorophor, a radioactive label, a chemiluminescent agent, an enzyme, a substrate, a receptor, a ligand, a hapten, an antibody and the like, such that the compound may serve as a labeled or detectable probe in hybridization assays. The reporter group can be further attached to any other component of the compound, such as the exoconjugates [K] and [I], the linker groups X and Y and the linker chain L.

Yet furthermore, any one or more of the B chemical functionality groups can be a ligand capable of interacting and covalently alter a complementary DNA or RNA strand. Suitable ligand, include natural or analog nucleobase modified with an alkylating electrophile, such as but not limited to 3-(iodoacetamido)propyl, in position 5 of deoxyuridine. In the later case, the modified compound, may upon base pairing with a complementary target nucleic acid strand, to covalently cross link with the 7-position of a guanine residue present in the complementary DNA or RNA strands. Subsequently depurination of the cross-linked guanine and strand scission of the complementary strand may naturally occur under in vivo conditions. To this effect the reader is referred to Meyer et al. (1989) Efficient specific cross-linking and cleavage of DNA by stable synthetic complementary oligodeoxynucleotides. J. Am. Chem. Soc. 111: 8517.

Each of Y first linker groups call be a C-alkanoyl group, such as a primary carbon atom, a secondary carbon atom and a tertiary carbon atom. Preferably, each of the Y linker groups is a methylene group (i.e., a secondary carbon atom).

As used herein, the term "C-alkanoyl group" includes a carbon atom substituted by one or, more alkyl groups.

Furthermore, each of the Y linker groups can be a substituted or unsubstituted (C2–C4) alkylene chain, as this term is defined hereinabove. When substituted, the substituent group can be an aryl group, an alkyl group and any other hydrocarbon group. In some cases Y can be just a single bond.

Each of the X second linker groups can be a methylene group, amine, amide, a sulfur atom, an oxygen atom, a selenium atom, a C-alkanoyl group, a phosphate derivative group (e.g. methyl phosphate and phosphoamidate), or a carbonyl group. In some cases X can be just a single bond $C_m$, $C_{n-1}$ and $C_n$ are chiral carbon atoms. The chirality of these atoms may be selected either of S or R configurations. Presently, the S configuration is preferred. As is further detailed hereinbelow, the compound according to the invention is built in a stepwise manner, wherein each monomer or other building block is sequentially added to a growing polymer. Therefore, provided that the building blocks can be prepared with a desired chirality (i.e., R or S configurations) a compound of predetermined ye: mixed S and R configurations C chiral carbons can be prepared.

Further according to the invention, [K] and [I] are a first and second exoconjugates such as, but not limited to, polyethylene glycol (PEG) moieties each having one or more repeat units or a hydrogen atom. Exoconjugate [K] and [I] may be water soluble or water insoluble polymers. Such conjugates can be used to modulate the ability of the compound to cross cell membranes. Furthermore, any one or both [K] and [I] can further include a reporter molecule, as is detailed hereinbelow. Nevertheless, any one or both [K] and [I] may be a hydrogen atom.

The backbone (Q) to which the chemical functionality groups are attached typically includes a plurality of chiral carbon atoms (Cm-Cn), as described hereinabove. According to a preferred embodiment of the present invention, the chiral carbon atoms are separated from one another by from four to six, preferably five, carbon atoms. An appropriate selection of the backbone Q and the linker groups X and Y can provide for the eleven atoms separation between adjacent nucleobases required for mimicking native DNA, as is further detailed hereinbelow.

Figure 1B:
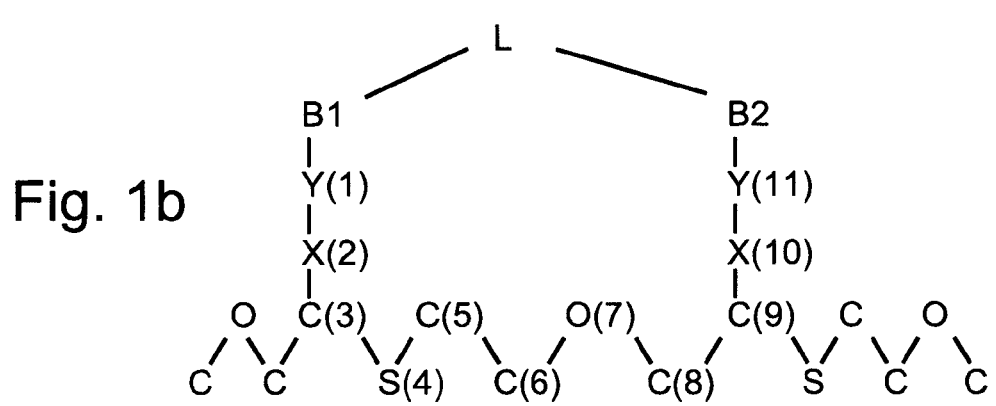

With reference now to FIGS. 1a–b, in accordance with the teachings of the present invention, it is shown therein that the X and Y groups serve as linker groups to ensure the presence of preferably eleven atoms spacing between adjacent chemical functionality groups B, as is the case in natural nucleic acids. FIGS. 1a–b present two adjacent nucleobases B on a native DNA strand (FIG. 1a) and on a nucleic acid derivative strand according to the preferred embodiment of the invention (FIG. 1b).

A preferred backbone according to the present invention includes a polyether and/or a polyether derivative. The use of polyether and polyether derivatives such as, but not limited to, poly(ether-thioether), poly(ether-sulfone) and poly(ether-sulfoxide) as backbones in nucleic acid analogs is described in U.S. Pat. No. 5,908,845, U.S. patent application Ser. No. 09/1411,862 and WO 01/16365, which are incorporated herein by reference.

However, other known backbones, which are typically used in nucleic acid analog compounds, can be used in the context of the present invention. Representative examples of such compounds include, without limitation, a thiophosphonate DNA backbone (see, Agrawal et al. (1998) Curr. Opin. Chem. Biol Antisense therapeutics. 2, 519–528), a phosphoramidate backbone (see, Faria et al. (2001) Nature biotechnology. Phosphoramidate oligonucleotides as potent antisense molecules in cell and in vivo. 19, 40–44), a morpholino phosphoramidate backbone (see, Summerton et al. (1992) Biotechnology international. Century. London, 73–77) and a methyl phosphonate backbone (see, Miller et al. (1991) Bio Technology. Oligonucleotides methylphosphonates as antisense reagents. 9, 358–361).

According to a preferred embodiment of the present invention, the backbone includes poly(ethylene glycol) (PEG). As is described in U.S. Pat. No. 5,908,845, PEG is characterized by a variety of advantageous biocompatible properties such as a wide range of solubilities in both organic and aqueous media, lack of toxicity and immunogenicity, nonbiodegradability and ease of excretion from living organisms.

Thus, a preferred nucleic acid derivative compound according to the present invention has the general formula (III):

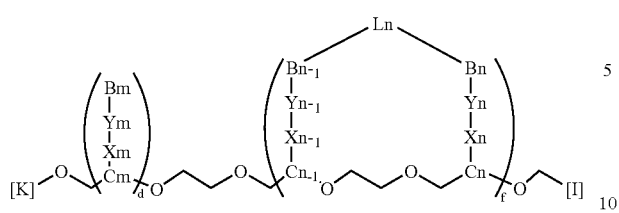

wherein m, n, d, f, L, B, Y, X, C, K and I are as defined hereinabove.

A further preferred nucleic acid derivative according to the present invention has the general formula IV:

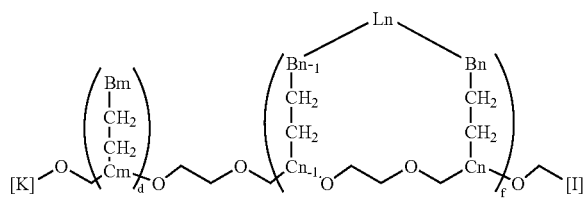

wherein m, n, d, f, L, B, C, K and I are as defined hereinabove.

Presently, the most preferred embodiment is the compound having the above general formula IV, wherein L is a linker chain having the formula:

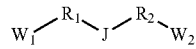

where R1, R2, W1 and W2 are as defined hereinabove and J is an amide group; B is a natural nucleobase, i.e., thymine (T), adenine (A), cytosine (C), guanine (G) and uracil (U); the sum of m and n ranges between 12 and 22 and further wherein d is an integer ranging between 12 and 20 and f is an integer ranging between 2 and 4.

Figure 2:
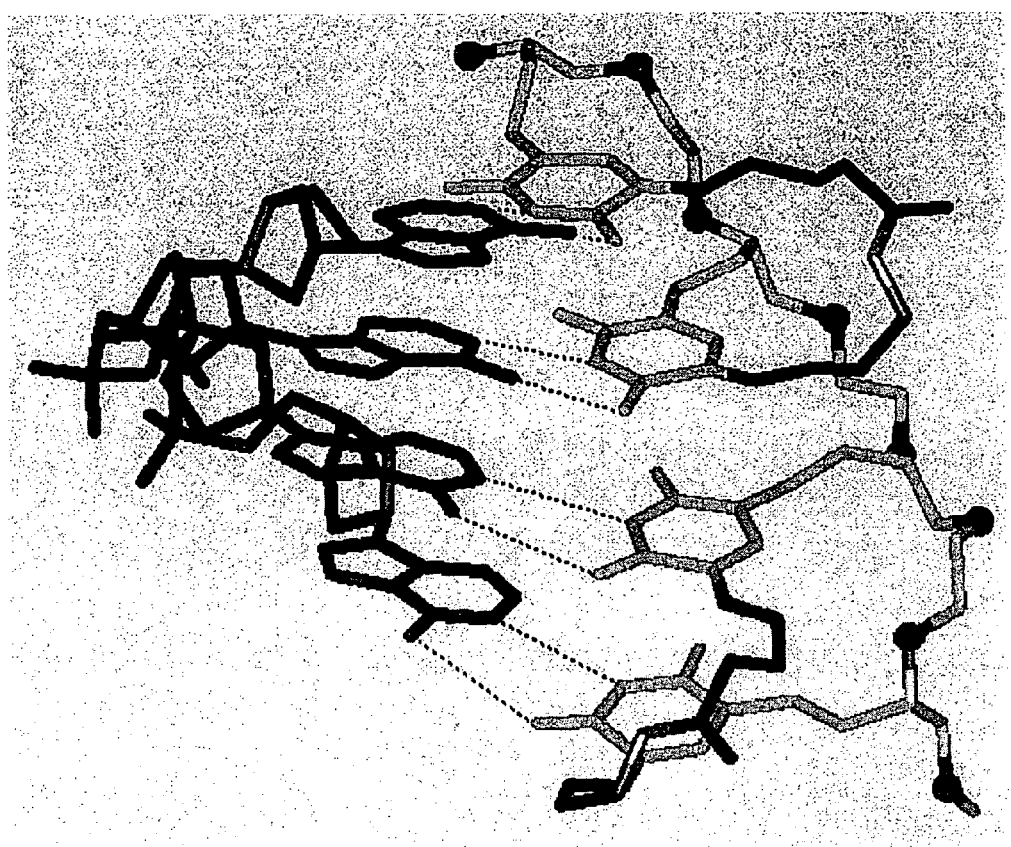
FIG. 2 is a molecular model presenting hybridization of a tetra-thymine-polyether nucleic acid having eleven atoms between adjacent B functionality groups according to the present invention with natural tetra-adenine-ssDNA.

With reference now to FIG. 2, molecular modeling that represents the hybridization of a tetra-thymidine-nucleic acid derivative compound according to formula IV above with natural adenine tetra nucleotide predicts a perfect hybridization match of the hydrogen bonds of the hybrid with minimum energy, wherein O is presented in red; the PEG backbone with attached bases are in blue, the carbon atoms chain in the linker chain are in back, the N atom of the amide group in the linker chain is in blue and O of the amide group is in red and the hydrogen bonds formed are emphasized by dashed lines, connecting the relevant atoms.

The nucleic acid derivatives of the present invention may be synthesized using standard DNA synthesis procedures, either in solution or on a solid support.

The building blocks used are specially designed chiral dimers and monomers.

A preferred dimeric building block according to the invention has the general formula V:

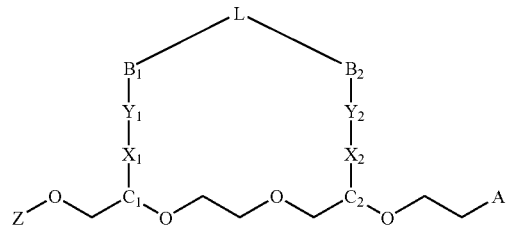

wherein L, B, Y and X are as defined above, Z is a suitable protecting group and A is a suitable leaving group.

Z is a protecting group for protecting the terminal hydroxyl group of the dimer. Z can be any suitable protecting group known in the art such as, but not limited to, a dimethoxytrityl group, a trityl group, a monomethoxytrityl group or a silyl group. Preferably Z is a trityl group or a dimethoxytrityl group.

A is a leaving group such as a halide group, a sulfonate group, an ammonium derivative, or any radical moiety that could be replaced by SN1 or SN2 mechanisms (for SN1 or SN2 mechanisms see Roberts and Caserio (1965) Basic principles of organic chemistry. U. A. Benjamin Inc. New-York, N.Y., page 292).

Should a specific building block include B which is a natural or analog nucleobase, the amino groups thereof may be protected with any conventional protecting group P, such as but not limited to a benzamido group, a methylbenzylether group, a methoxybenzylether group, an isobutyramido group, a t-butoxycarbonyl (Boc) group, a benzyloxy methyl (BOM), a dimethyl pyrrolidone or an acid labile group which is not cleaved by reagents, such as alkoxyl base, that cleave the Z protecting group.

The dimeric compound represented by formula V, also referred to herein as a cyclic dimeric compound, serves as a unique building block in the synthesis of the oligonucleotide analog of the present invention, represented by formula III hereinabove.

A preferred dimeric compound according to the present invention has the general formula VI:

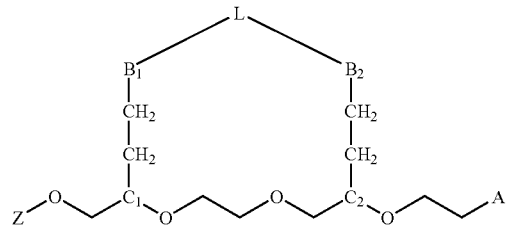

wherein B1 and B2 (formula V) are natural nucleobases, i.e., thymine (T), adenine (A), cytosine (C), guanine (G) and uracil (U); and L has the general formula:

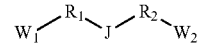

as described hereinabove.

The dimeric compound of formula VI includes natural nucleobases, which have an amine group, and therefore each of the nucleobases of the compound is preferably protected by a protecting group P. Thus, a preferred compound according to the present invention has a general formula VII:

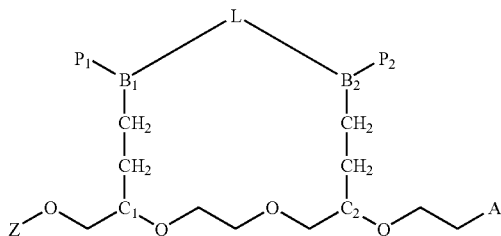

wherein L, B, C, Z and A are as defined hereinabove and each of P1 and P2 is a second protecting group P as described hereinabove.

In a preferred embodiment of the present invention, the dimeric compound represented by formula VI, has a L linker chain having the formula presented hereinabove, wherein W1 and W2 are each a double bond, R1 and R2 are each an alkylene chain and J is an amide linking group.

Thus, another preferred dimeric compound according to the present invention has the general formula VIII:

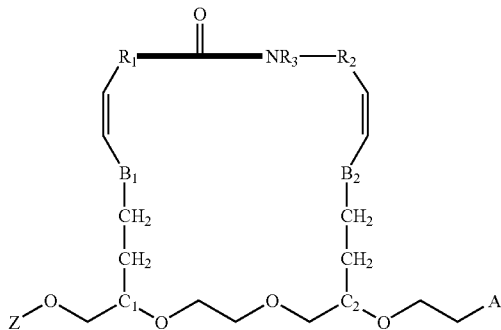

wherein B, C, A, Z, R1 and R2 are as defined hereinabove and R3 is a hydrogen, methyl or alkyl.

The compound of formula VIII preferably further include protecting groups P1 and P2 attached to B1 and B2, as is described hereinabove for formula VII.

Thus, the cyclic dimeric compounds according to the present invention include, for example, cyclic dimeric compounds having two identical nucleobases or nucleobase analogs linked therebetween via the linker chain L, e.g., C-L-C; T-L-T; G-L-G; A-L-A and U-L-U. Alternatively, the cyclic dimeric compounds according to the present invention include a combination of two different nucleobases or nucleobase analogs linked therebetween by the linker chain L, e.g., C-L-T; U-L-C; A-L-G and any other combination of non-identical nucleobases.

A representative example of a cyclic dimeric compound having two cytosine bases (C-L-C) according to the present invention is presented in formula IX:

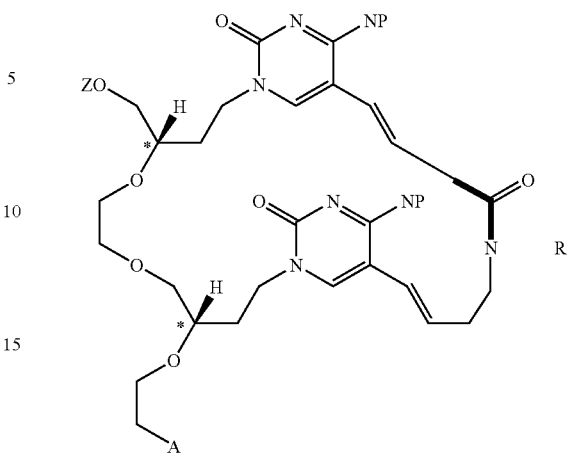

Further according to the present invention, there is provided a process of preparing the dimeric building blocks of the present invention.

The process is effected by obtaining an ethylene glycol moiety, also referred to herein as a first ethylene glycol moiety, represented by the general formula X:

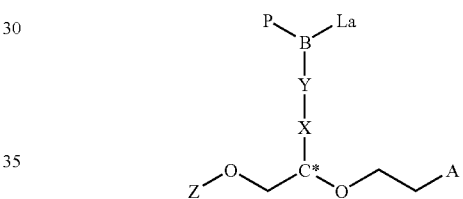

wherein, X, Y, P and B are as defined hereinabove and La is a linker arm terminating with a chemically reactive group.

As used herein, the phrase "chemically reactive group" includes chemical functionality groups that are capable of participating in a condensation reaction. Typical examples of such chemically reactive groups include, without limitation, electrophilic groups such as carboxylic acid and its derivatives, e.g., ester, thioester, amide and acylhalide, and nucleophilic groups such as amino, hydroxyl, alkoxyl, aryloxy, thiol (also referred to herein as sulfhydril) and thioalkyl.

The first ethylene glycol moiety is condensed with another ethylene glycol moiety having a chiral carbon atom, so as to obtain a diethylene glycol moiety having a single nucleobase or nucleobase analog attached thereto. The diethylene glycol moiety is reacted with a nucleobase or a nucleobase analog having a second linker arm terminating with a second chemically reactive group. The process is designed such that the first and second chemically reactive groups are, interchangeably, an electrophilic and nucleophilic groups, which are easily condensed when reacted therebetween. Thus, the obtained diethylene glycol moiety is thereafter reacted such that the first and second linker arms are condensed, so as to form the linker chain I connecting the two nucleobases or nucleobase analogs of the diethylene glycol moiety.

Figure 10I:
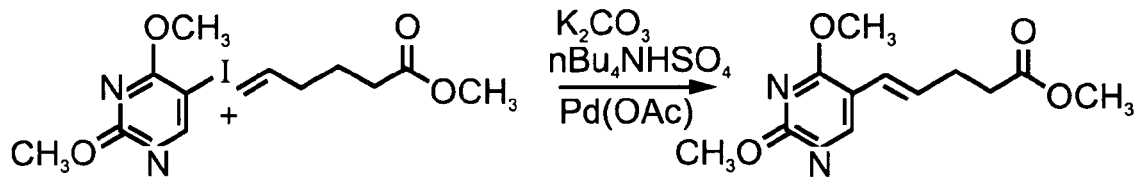
FIGS. 10(i)–(v) illustrate the synthesis of a cyclic dimeric building block (cyclic dimer-PEG-T) of the present invention.
Figure 10I:
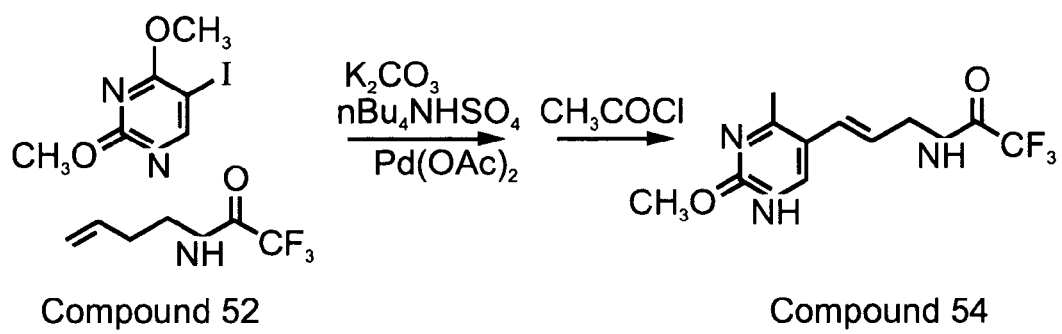
Figure 10I:
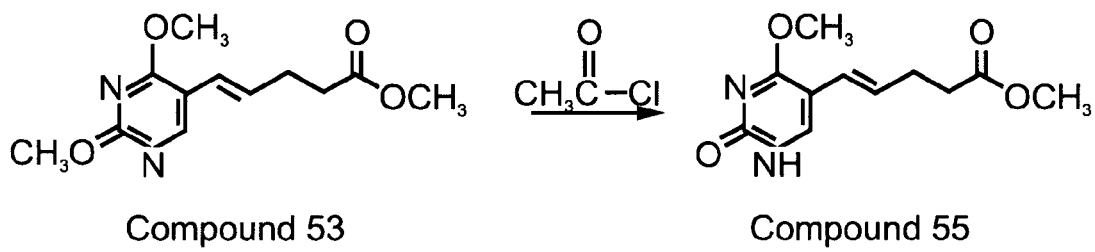
Figure 10I:
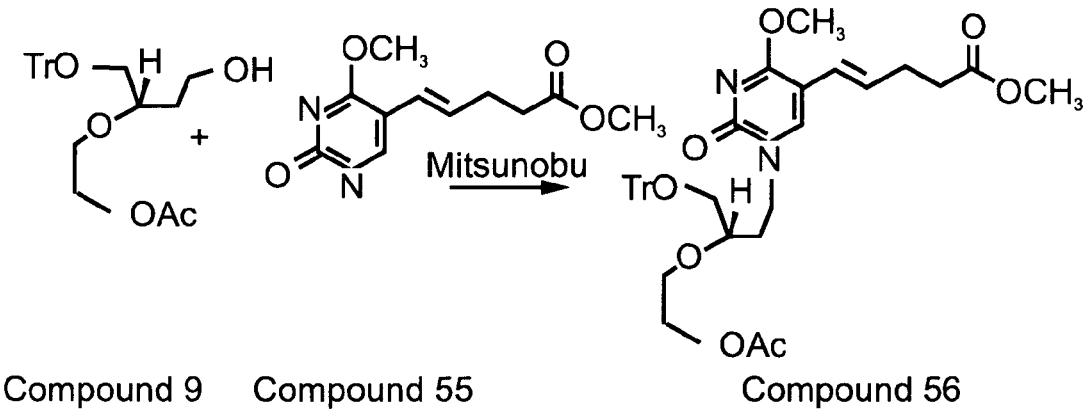
Figure 10:
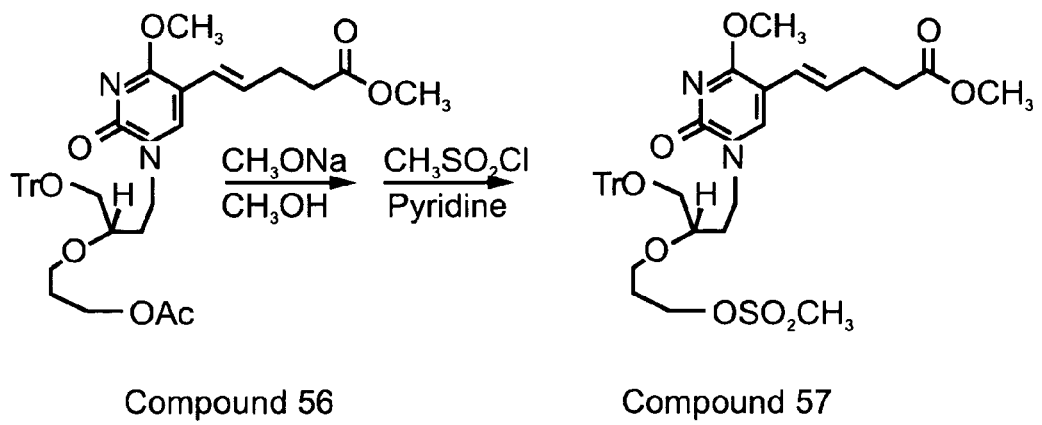
Figure 10:
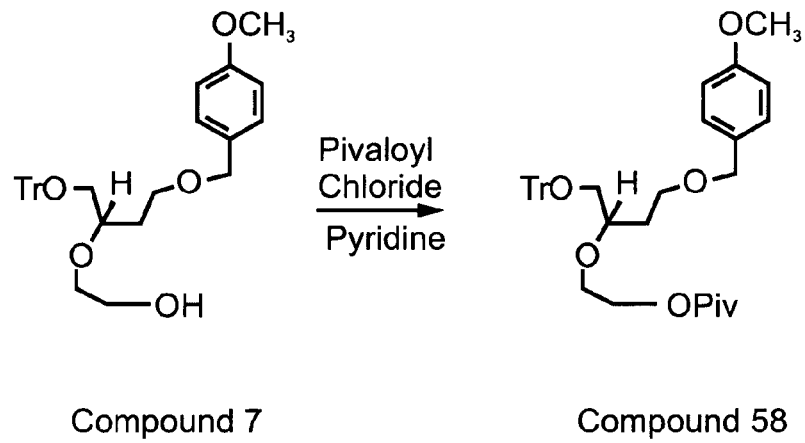
Figure 10:
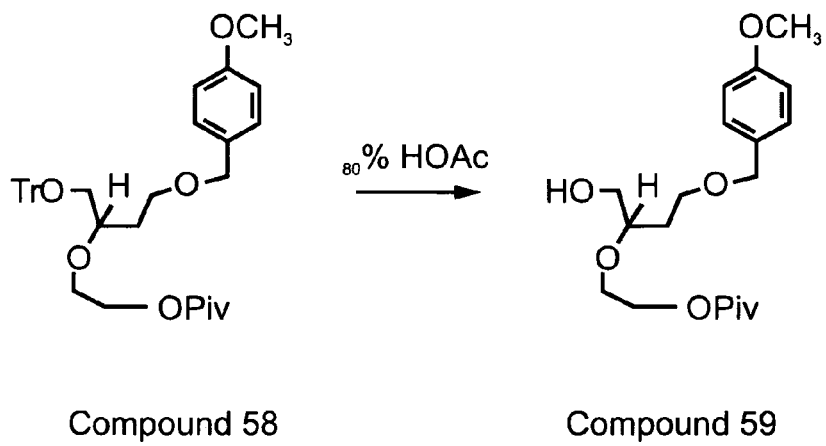
Figure 10:
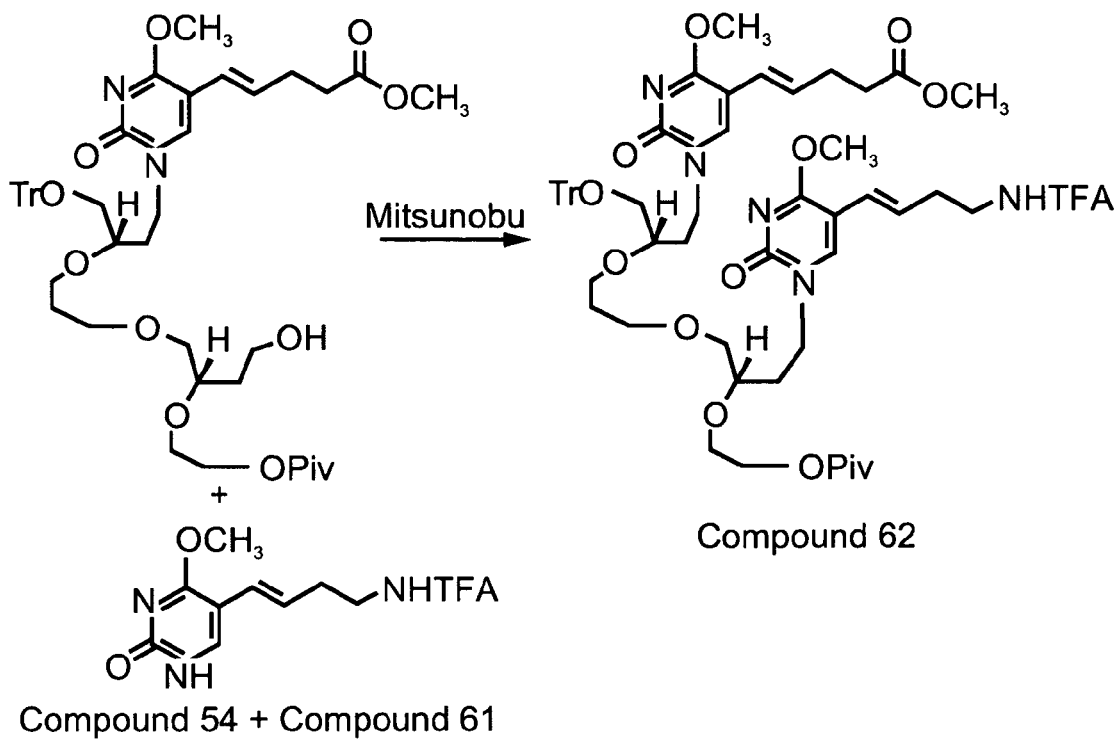
Figure 10:
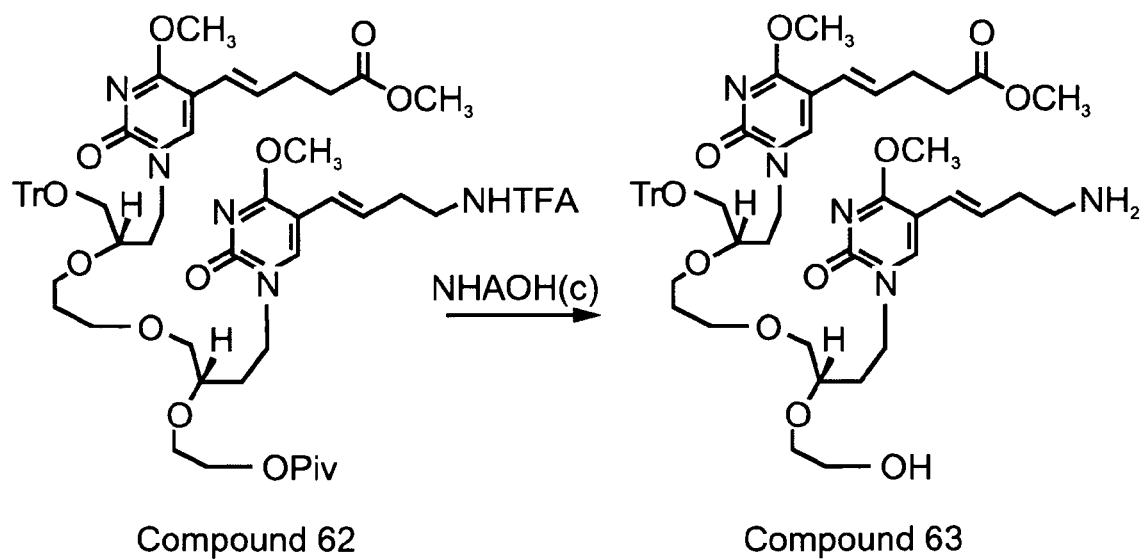
Figure 10V:
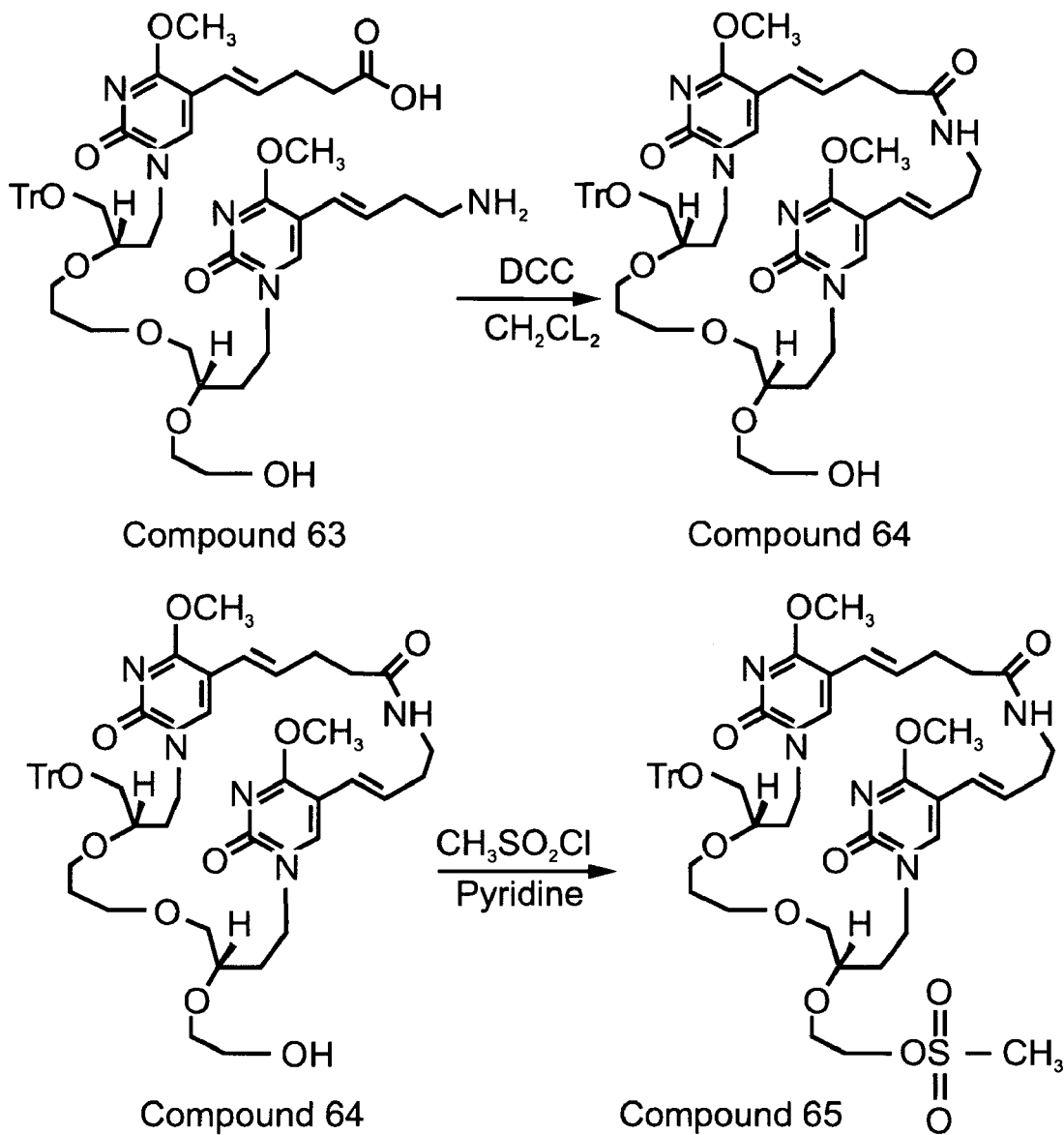

Then, the obtained cyclic moiety is converted, by SN1 or SN2 mechanism, to a diethylene glycol moiety having a leaving group A attached thereto, as is described for formula VI hereinabove. A representative example of the process described hereinabove is schematically illustrated in FIGS. 10(i)–(v).

A preferred monomeric acyclic building block according to the invention has the general formula XI:

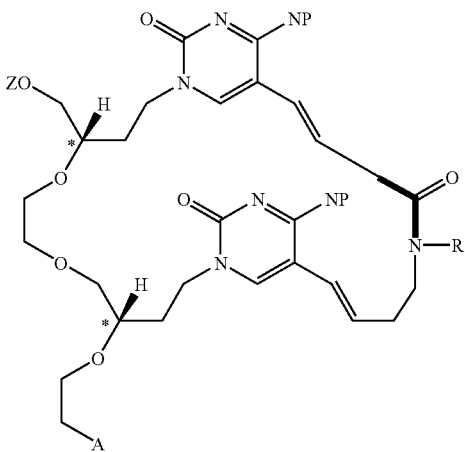

wherein X, Y, B, P, K and I are as defined hereinabove and C* is a chiral carbon atom. The process of preparing the acyclic monomeric compound is described in U.S. Pat. No. 5,908,845. Additional synthetic routes for obtaining this monomeric compound are further described in the Examples section that follows.

Another preferred monomeric acyclic building block has the general formula XII:

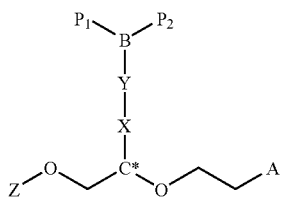

wherein B, Y, X, C*, Z, A and P1 and P2 are as defined hereinabove.

A single nucleobase B in this compound is protected by two identical or non-identical protecting groups P1 and P2. Such a monomer is highly advantageous in the synthesis of oligonucleotides according to the present invention.

According to preferred embodiments of the present invention, each of the monomeric or dimeric compounds of the invention can be labeled by a reporter molecule, as described hereinabove, linked thereto. The incorporation of a labeled building block into the oligonucleotide analog of the present invention is highly advantageous since the resulting labeled oligonucleotide analog can serve as a labeled or detectable probe in hybridization assays.

The monomeric and dimeric building blocks described hereinabove are used in processes of preparing the oligonucleotide analogs of the present invention. These processes are performed either in solution or over a solid support in solid phase synthesis.

In one process, the chiral monomer and dimer building blocks described hereinabove are condensed therebetween or one with the other, using known procedures, in a pre-determined sequence, so as to obtain an oligonucleotide analog of a predermined sequence.

In another process, a first monomeric compound or a first dimeric compound is attached to a solid support and the monomers and dimers are thereafter condensed with the monomer in a pre-determined sequence, so as to obtain the oligonucleotide analog attached to a solid support. De-attaching the oligonucleotide analog from the solid support is performed using procedures well known in the art.

The solid support according to the present invention includes resins that are typically used in solid-phase syntheses of synthetic oligonucleotides or oligonucleotide analogs. Representative examples of preferred solid supports include, without limitation, a controlled pore glass CPG, a Wang resin and a Merrifield's peptide resin.

As described hereinabove, according to preferred embodiments of the present invention, the oligonucleotide analog includes a PEG backbone to which natural or analog nucleobases are covalently attached, which is also referred to herein as oligo-PEG-B (B=C, T, G, A and U). The processes for preparing these oligo-PEG-B nucleotide analogs therefore involve the condensation of the dimeric and monomeric building blocks represented by formulas VI and XI, respectively. However, it should be evident for one ordinarily skilled in the art that the use of other equivalent building blocks and, in particular, the use of the thiolated building blocks described in U.S. patent application Ser. No. 09/411,862 and WO 01/16365, is also applicable within the context of the present invention.

The present invention is further directed at use of oligonucleotide analogs in solid-phase biochemistry (see, Solid-Phase Biochemistry—Analytical and Synthetic Aspects (1983) W. H. Scouten, ed., John Wiley & Sons, New York), notably solid-phase biosystems, especially bioassays or solid-phase techniques which concerns diagnostic detection/quantitation or affinity purification of complementary nucleic acids (see, Affinity Chromatography—A Practical Approach (1986) P. D. G. Dean, W. S. Johnson and F. A. Middle, eds., IRL Press Ltd., Oxford; Nucleic Acid Hybridization—A Practical Approach (1987) B. D. Harnes and S. J. Higgins, IRL Press Ltd., Oxford).

Present day methods for performing such bioassays or purification techniques almost exclusively utilize "normal" or slightly modified oligonucleotides either physically absorbed or bound through a substantially permanent covalent anchoring linkage to solid supports such as cellulose, glass beads, including those with controlled porosity (mizutani, et al., (1986) J Chromatogr. 356:202), "Sepharose", "Sephadex", polyacrylamide, agarose, hydroxyalkyl methacrylate gels, porous particulate alumina, porous ceramics, diobonded silica, or contiguous materials such as filter discs of nylon or nitrocellulose. One example employs the chemical synthesis of oligo-dT on cellulose beads for the affinity isolation of poly A tail containing mRNA (Gilham in Methods in Enzymology (1971) L. Grossmann and K. Moldave, eds., vol. 21, part D, page 191, Academic Press, New York and London).

All the above-mentioned methods are applicable within the context of the present invention. However, when possible, covalent linkage is preferred over the physical adsorption of the molecules in question, since the latter approach has the disadvantage that some of the immobilized molecules can be washed out (desorbed) during the hybridization or affinity process.

There is, thus, little control of the extent to which a species adsorbed or the surface of the support material is lost during the various treatments to which the support is subjected in the course of the bioassay/purification procedure. The severity of this problem will, of course, depend to a large extent on the rate at which equilibrium between adsorbed and "free" species is established. In certain cases it may be virtually impossible to perform a quantitative assay with acceptable accuracy and/or reproducibility. Loss of absorbed species during treatment of the support with body fluids, aqueous reagents or washing media will, in general, be expected to be most pronounced for species of relatively low molecular weight.

Thus, the oligonucleotide analogs of the present invention benefit from the above-described solid-phase techniques with respect to the much higher (and still sequence-specific) binding affinity for complementary nucleic acids and from the additional unique sequence-specific recognition of (and strong binding to) nucleic acids present in double-stranded structures. They can therefore replace common oligonucleotides in hybridization assays such as but not limited to blot hybridizations ("Southern" and "Northern"), dot blot hybridizations, reverse blot hybridizations, in situ hybridizations, liquid phase hybridizations, clones (bacteria/phages, etc.) screening and in other assays involving hybridizations such as but not limited to PCR, sequencing, primer extension and the like.

They also can be loaded onto solid supports in large amounts, thus further increasing the sensitivity/capacity of the solid-phase technique. Further, certain types of studies concerning the use of the oligonucleotide analogs of the present invention in solid-phase biochemistry can be approached, facilitated, or greatly accelerated by use of the recently-reported "light-directed, spatially addressable, parallel chemical synthesis" technology (Fodor, et al. (1991) Science, 251:767), a technique that combines solid-phase chemistry and photolithography to produce thousands of highly diverse, but identifiable, permanently immobilized compounds (such as proteins) in a substantially simultaneous way.

The present invention is further directed at therapeutic and/or prophylactic uses for the nucleic acid derivative compounds. Likely therapeutic and prophylactic targets according to the invention include but are not limited to human papilloma virus (HPV), herpes simplex virus (HSV), candidia albicans, influenza virus, human immunodeficiency virus (HIV), intracellular adhesion molecules (ICAM), cytomegalovirus (CMV), phospholipase A2 (PLA2), 5-lipoxygenase (5-LO), protein kinase C (PKC), and RAS oncogene.

Potential applications of such targeting include but are lot limited to treatments for labial, ocular and cervical cancer; genital warts; Kaposi's sarcoma; common warts; skin and systemic fungal infections; AIDS; pneumonia; flu; mononucleosis; retinitis and pneumonitis in immunosuppressed patients; ocular, skin and systemic inflammation; cancer; cardiovascular disease; psoriasis; asthma; cardiac infarction; cardiovascular collapse; kidney disease; gastrointestinal disease; osteoarthritis; rheumatoid arthritis; septic shock; acute pancreatitis; and Crohn's disease.

For therapeutic or prophylactic treatment, the nucleic acid derivatives of the present invention can be formulated in a pharmaceutical composition.

Thus, the pharmaceutical compositions according to the present invention include the oligonucleotide analog, as an active ingredient, and a pharmaceutically acceptable carrier.

As used herein a "pharmaceutical composition" refers to a preparation of one or more of the oligonucleotide analogs described herein, with other chemical components such as pharmaceutically suitable carriers and excipients, The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water. Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The nucleic acid derivative compounds described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient, may be in powder form for constitution with a suitable vehicle, e.g., sterile, pyrogen-free water, before use.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose.

Determination of a therapeutically effective amount is well within the capability of those skilled in the art, especially in light of the detailed disclosure provided herein.

For any oligonucleotide compound used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test compound, which achieves a half-maximal inhibition of the ChE or COX activity). Such information can be used to more accurately determine useful doses in humans.

Toxicity and therapeutic efficacy of the compounds described herein can be determined by standard pharmaceutical procedures in experimental animals, e.g., by determining the IC50 and the LD50 (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch 1 p.1).

Depending on the severity and responsiveness of the condition to be treated, dosing can be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising an oligonucleotide analog of the invention formulated in a compatible pharmaceutical carrier may also be prepared, placed in an appropriate container, and labeled for treatment of an indicated condition.

Therapeutic treatments using the oligonucleotide analogs of the present invention or pharmaceutical compositions thereof can be practiced on a variety of organisms ranging from unicellular prokaryotic and eukaryotic organisms to multicellular eukaryotic organisms. Any organism that utilizes transcription (including DNA-RNA transcription and reverse transcription), RNA transcripts or RNA-protein translation as a fundamental part of its hereditary, metabolic or cellular control is susceptible to therapeutic and/or prophylactic treatment in accordance with the present invention. Seemingly diverse organisms such as yeast, bacteria, algae, protozoa, all plants and all higher animal forms, including warm-blooded animals, can be treated.

Further, each cell of multicellular, eukaryotes can be treated since they include both DNA-RNA transcription fund RNA-protein translation as integral parts of their cellular activity.

Furthermore, many of the organelles (e.g., mitochondria, chloroplasts and chromoplasts) of eukaryotic cells also include transcription and translation mechanisms. Thus, single cells, cellular populations or organelles can also be included within the definition of organisms that can be treated with therapeutic or diagnostic phosphorothioate oligonucleotides. As used herein, therapeutics is meant to include the eradication of a disease state, by killing an organism or by control of erratic or harmful cellular growth or expression.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE 1

Preparation of a Starting Material for the Monomer Described by Formula XI

Figure 3I:
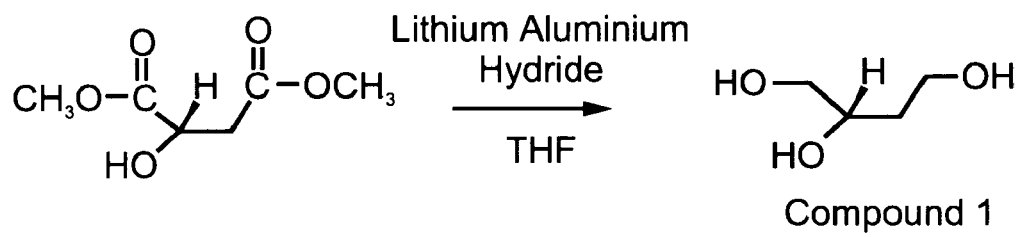
FIGS. 3(i)–(iv) illustrate the synthesis of Compound 9 (a starting material) of the present invention.
Figure 3I:
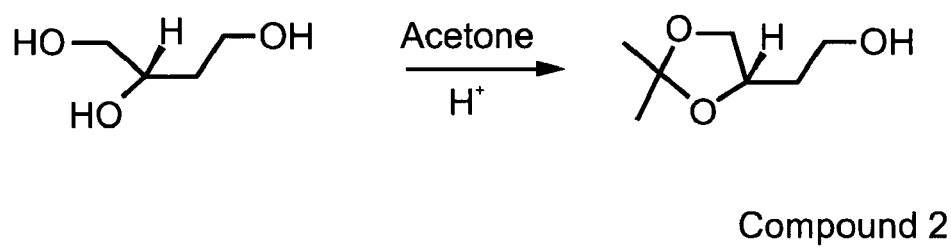
Figure 3I:
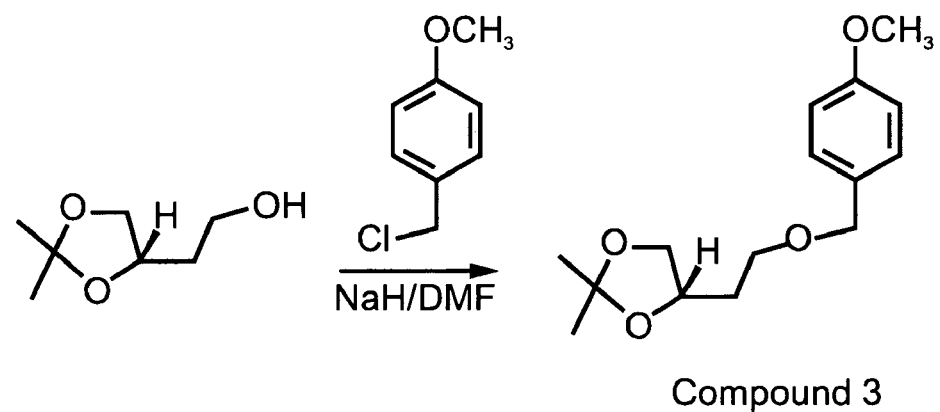

The preparation of a representative example of a starting material for the monomer described by formula XI is described hereinafter. The processes are schematically illustrated in FIGS. 3(i)–(iv).

Chirality selection: The starting material for synthesizing the compound descried hereinabove is preferably (S)-(−)-Dimethyl malate (Aldrich). This compound has a chiral center which possesses the appropriate S configuration.

Preparation of (S)-1,2,4-Butanetriol (Compound 1): (S)-(−)-Dimethyl malate (25.2 grams) dissolved in 30 ml of dry tetrahydrofuran, was added dropwise to a suspension of 21 grams of lithium aluminum hydride in 1 liter of dry tetrahydrofuran. The mixture was refluxed overnight. Addition of ethyl acetate (930 ml), followed by addition of water (160 ml) and an additional solution of 10% sulfuric acid (50 ml) gave a white precipitate which was filtered and washed with 4×130 ml portions of dry ethanol. The combined solution was evaporated to near dryness under reduced pressure. The residual oil was purified by short column chromatography over 50 grams of silica gel, using a mixture of chloroform and ethanol as eluent (560 ml) of a mixture of 3:1 (v:v) chloroform:ethanol and 670 ml of a mixture of 2:1 (v:v) chloroform:ethanol. After the removal of the solvent, 12 grams (60% yield) of Compound 1 were obtained as pale yellow oil, which was identified as a pure product by $^1$H-NMR.

$^1$H-NMR (pyridine): δ=2.14 (2H, m), 3.97 (2H: dd, J=5 Hz), 4.17 (2H, dt, J1=5 Hz, J2 =6 Hz), 5.38 (1H, m), 6.00 (3H, —OH) ppm.

Preparation of (S)-1,2-O-isopropylidene-1,2,4-butanetriol (Compound 2): (S)-1,2,4-Butanetriol (Compound 1) (106 grams, 1 mole) was dissolved in a mixture of 10% 1,2-dimethoxypropane in 800 ml acetone and a solution of 10% methanol in dioxane which contained a catalytic amount (2.5 grams) of p-toluenesulfonic acid and 40 grams of anhydrous sodium sulfate. The resulting solution was stirred at room temperature for eight hours. Sodium bicarbonate was then suspended in the solution and the mixture was thereafter filtered. The solvent was removed under reduced pressure and the residue was purified by silica gel chromatography, using a mixture of 2:1 (v:v) ethyl acetate:hexane as eluent. 136 grams (95% yield) of Compound 2 were obtained as an oil.

TLC (2:1 ethyl acetate:hexane): Rf=0.50.

$^1$H-NMR (in CDCl$_3$): δ=1.36 (3H, q, J=0.75 Hz), 1.39 (3H, q, J=0.75 Hz), 1.81 (2H, dt, J1=5.5 Hz, J2=6 Hz), 3.10 (1H, br), 3.58 (1H, dd, J1=7 Hz, J2=7.5 Hz),3.75 (2H, t, J=6 Hz), 4.07 (1H, dd, J1=6 Hz, J2=7 Hz), 4.26 (1H, diffuse heptet, J=6.5 Hz) ppm.

Preparation of (S)-1,2-O-isopropylidene-O-(4-methoxybenzyl)-1,2,4-butanetriol (Compound 3): To a solution of (S)-1,2-O-isopropylidene-1,2,4-butanetriol (Compound 2) (5 grams, 34 mmoles) in dry DMF, sodium hydride (60% dispersion in oil) (2 grams, 86 mmoles) was added gradually, under argon atmosphere. The mixture was stirred for one hour at room temperature and thereafter 4-methoxybenzyl chloride (Aldrich), (7.98 grams, 51 mmoles) was added and the mixture was heated at 50° C. for 2 hours. The solvent was then evaporated to dryness and the residue was extracted with ethyl acetate and washed with water and brine. The organic layer was dried over sodium sulfate and the solvent was evaporated. The resulting yellowish oily residue was purified by silica gel chromatography, using a mixture of 1:2 (v v) ethyl acetate:hexane as eluent. 8.65 grams (95% yield) of Compound 3 were obtained as an oil.

TLC (1:2 ethyl acetate:hexane): Rf=0.65.

$^1$H-NMR (in CDCl$_3$): δ=1.39 (3H, s), 1.44 (3H, s), 1.90 (2H, m), 3.61 (2H, m), 3.83 (3H, s), 4.09 (2H, m), 4.24 (1H, m ), 4.47 (2H, s), 6.9–7.3 (4H, Ar—H) ppm.

Preparation of (S)-4-O-(4-methoxybenzl)-1,2,4-butanetriol (Compound 4): Compound 3 (26.6 grams, 100 mmoles) was dissolved in 80% acetic acid (200 ml) and the solution was stirred overnight at room temperature and thereafter was heated for two hours at 50° C. The solvent was evaporated to dryness and the residue was dissolved in chloroform and purified by silica gel chromatography using ethyl acetate as eluent. 21.3 grams (94% yield) of Compound 4 were obtained as an oil.

TLC (ethyl acetate): Rf=0.26.

$^1$H-NMR (in CDCl$_3$): δ=1.79 (2H, m), 3.49 (2H, m), 3.64 (2H, m), 3.65 (2H, m), 3.82 (3H, s), 3.88 (1H, m,), 6.89–7.29 (4H, Ar—H) ppm.

Preparation of (S)-1-O-trityl-4-O-(4-methoxybenzyl)-1,2,4 -butanetriol (Compound 5): To a solution of Compound 4 (22.6 grams, 100 mmoles) in 200 ml dry pyridine, trityl chloride (30.7 grams, 110 mmoles) was added dropwise, under argon atmosphere and the mixture was stirred overnight at room temperature. The solvent was thereafter evaporated to dryness and the residue was extracted with ethyl acetate and washed with water and brine. The organic layer was dried over sodium sulfate and the solvent was thereafter removed under reduced pressure. The resulting yellowish oily residue was purified by silica gel chromatography, using 1:2 (v:v) ethyl acetate:hexane as eluent. 41.2 grams (88% yield) of Compound 5 were obtained as an oil.

TLC (1:2 ethyl acetate:hexane): Rf=0.46.

$^1$H-NMR (in CDCl$_3$): δ=1.80 (2H, m), 2.92 (1H, m), 3.17 (2H, d, J=0.7 Hz), 3.61 (2H, m), 3.82 (3H, s), 4.03 (1H, m), 4.42 (2H, s), 6.87–7.49 (19H, Ar—H) ppm.

Preparation of (S)-1-O-trityl-2-O-allyl-4-O-(4-methoxybenzyl)-1,2,4-butanetriol (Compound 6): To a solution of Compound 5 (10 grams, 21.4 mmoles) in dry THF (250 ml), a solution of 1M of potassium t-butoxide (Aldrich) (27.8 ml, 27.8 mmoles) in THF was added, under argon atmosphere.

The mixture was stirred at room temperature for 5 minutes and, thereafter, allyl bromide (Aldrich) (7.4 ml, 85.5 mmoles) was added. The mixture was stirred for 18 hours at 55° C. The solvent was thereafter evaporated to dryness and the residue was extracted with ethyl acetate (250 ml) and washed with water and brine. The organic layer was dried over sodium sulfate and the solvent was removed under reduced pressure. The resulting yellowish oily residue was purified by silica gel chromatography, using 1:2 (v:v) ethyl acetate:hexane as eluent, 10.75 grams (99% yield) of Compound 6 were obtained as an oil.

TLC (1:2 ethyl acetate:hexane): Rf=0.69.

$^1$H-NMR (in CDCl$_3$): δ=1.90 (2H, m), 3.21 (2H, d, J=0.7 Hz), 3.53 (2H, m), 3.62 (2H, m), 3.73 (1H, m), 3.83 (3H, s), 4.06 (2H, m), 4.21 (2H, m), 4.43 (2H, s), 5.22 (1H, d, J=0.7 Hz), 5.34 (1H, d, J=0.75 Hz), 5.95 (1H, m), 6.9–7.55 (19H, Ar—H) ppm.

Figure 3:
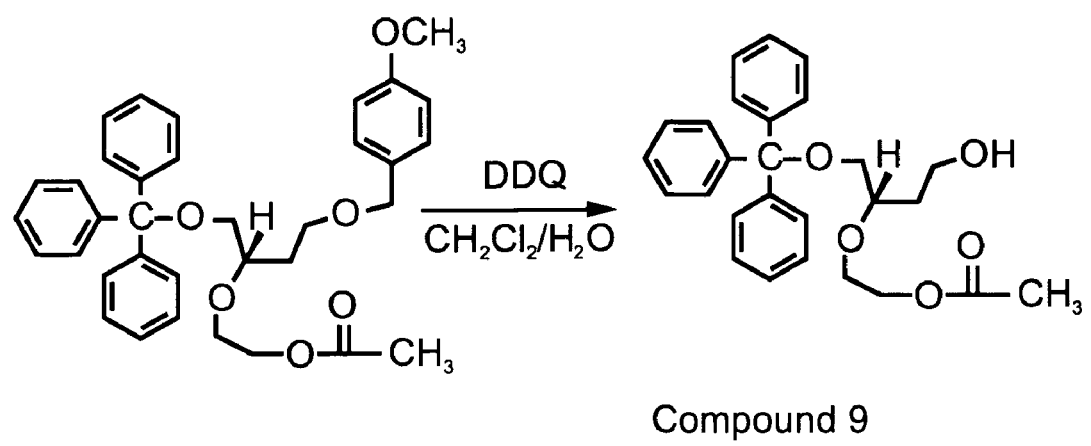

Preparation of (S)-1-O-trityl-2-O-ethanol-4-O-(4-methoxybenzyl)-1,2,4-butanetriol (Compound 7): To a solution of Compound 6 (5.08 grams, 10 mmoles) in THF (150 ml), N-methylmorpholine-N-oxide (Aldrich) (2.59 grams, 22.2 mmoles), followed by 4% aqueous solution of osmium tetraoxide (Aldrich) (0.4 ml, 1.57 mmoles) were added and the reaction mixture was stirred at room temperature for six hours. The solvent was thereafter evaporated to dryness and the residue was extracted with ethyl acetate (250 ml) and washed with water and brine. The organic layer was dried over sodium sulfate and the solvent was removed under reduced pressure. 5.42 (100% yield) of the corresponding diol (see, FIG. 3) were obtained as crude yellowish oil (TLC (ethyl acetate): Rf=0.30).

The obtained diol was subjected to cleavage and reduction reactions as follows: To a solution of the diol (5.42 grams, 10 mmoles) in 150 ml THF and 15 ml of water, NaIO$_4$ (2.34 grams, 10.96 mmoles) was added and the reaction was monitored by TLC, using ethyl acetate as eluent. After stirring the reaction mixture for three hours at room temperature, NaBH$_4$ (0.5 grams, 13 mmoles) was added gradually and the reaction mixture was stirred at room temperature for 30 minutes. The solvent was thereafter evaporated to dryness and the residue was extracted with ethyl acetate (250 ml) and washed with water and brine. The organic layer was dried over sodium sulfate and the solvent was removed under reduced pressure. The resulting yellowish oily residue was purified by silica gel chromatography, using 1:1 (v:v) ethyl acetate:hexane as eluent, 3.58 grams (70% yield) of Compound 7 were obtained as an oil.

TLC (1:1 ethyl acetate:hexane): Rf=0.34.

$^1$H-NMR (in CDCl$_3$): δ=1.88 (2H, m), 2.78 (1H, m), 3.24 (2H, d, J=0.6 Hz), 3.53 (1H, m), 3.66 (2H, m), 3.74–3.82 (2H, m), 3.86 (3H, s), 4.47 (2H, s), 6.92–7.54 (19H, Ar—H) ppm.

Preparation of (S)-1-O-trityl-2-O-(acetoxy-ethanol)-4-O-(4-methoxybenzyl)-1,2,4-butanetriol (Compound 8): A solution of Compound 7 (5, 2 grams, 10 mmoles), dry pyridine (50 ml) and acetic anhydride (50 ml) was stirred at room temperature for two hours. The solvents were thereafter removed under reduced pressure and the residue was extracted with ethyl acetate (250 ml) and washed with water and brine. The organic layer was dried over sodium sulfate and the solvent was evaporated. The resulting oily residue was purified by silica gel chromatography, using 1:1 (v:v) ethyl acetate:hexane as eluent. 5.5 grams (100% yield) of Compound 8 were obtained as an oil.

TLC (1:1 ethyl acetate:hexane): Rf=0.50.

$^1$H-NMR (in CDCl$_3$): δ=1.58 (2H, m), 1.82 (3H, s), 2.95 (2H, m), 3.24–3.49 (4H, m), 3.60 (3H, s), 4.00 (2H, m), 4.18 (2H, s), 6.65–7.28 (19H, Ar—H) ppm.

Preparation of (S)-1-O-trityl-2-O-(acetoxy-ethanol)-1,2, 4- butanetriol (Compound 9): To a cooled (5° C.) solution of Compound 8 (5.54 grams, 10 mmoles) in dichloromethane (200 ml) and water (10 ml), 2,3-dichloro-5,6dicyano-1, 4benzoquinone (DDQ) (Aldrich) (2.9 grams, 12.7 mmoles) was added. The cooled reaction mixture was stirred for 30 minutes and was thereafter extracted with 2×50 ml of 5% sodium bicarbonate and 2×200 ml of brine. The organic layer was dried over anhydrous sodium sulfate and the solvent was removed under reduced pressure. The resulting oily residue was purified by silica gel chromatography, using a mixture of 1:1 (v:v) ethyl acetate:hexane as eluent. 3.90 grams (90% yield) of Compound 9 were obtained as an oil.

TLC (1:1 ethyl acetate:hexane): Rf=0.41.

$^1$H-NMR (in CDCl$_3$): δ=1.79 (2H, m), 2.05 (3H, s), 3.17 (1H, m), 3.25 (1H, m), 3.69 (1H, m), 3.91 (1H, m), 4.18 (2H, m), 4.25 (2H, m), 7.25–7.47 (Ar—H) ppm.

EXAMPLE 2

Preparation of Cytosine-PEG Monomer (PEG-C)

The preparation of a cytosine-PEG monomer (PEG-C), according to the present invention, is effected by two alternative synthetic routes.

Figure 4A:
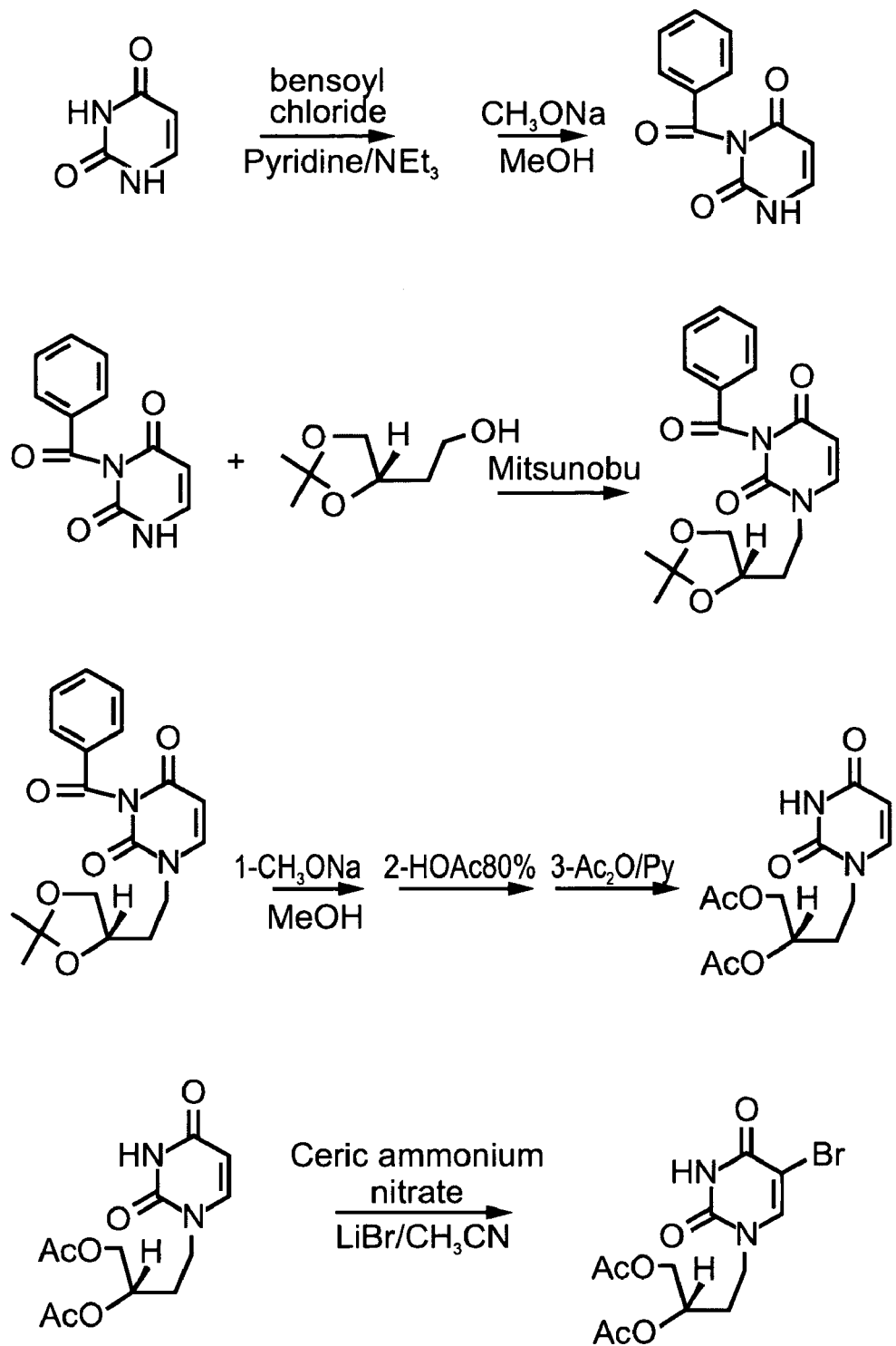
FIGS. 4a(i)–(iv) and 4b(i)–(iv) illustrate synthetic route A (FIG. 4a) and synthetic route B (FIG. 4b) of the preparation of a monomeric building block (PEG-C) of the present invention.

In one alternative, synthetic route A, the synthesis of PEG-C is based on the modification of uracil base to 2,4-diazaphenoxazine ring, which is aimed at enhancing the Pi-stacking of the PEG-oligomer, as is described by Dimitry et 37.9 mmoles) were added, under argon atmosphere. The slurry mixture was al., Nucleosides & Nucleotides (1997), vol 16, 1837 FIGS. 4a(i)–(iv) schematically illustrate synthetic route A of PEG-C.

Figure 4B:
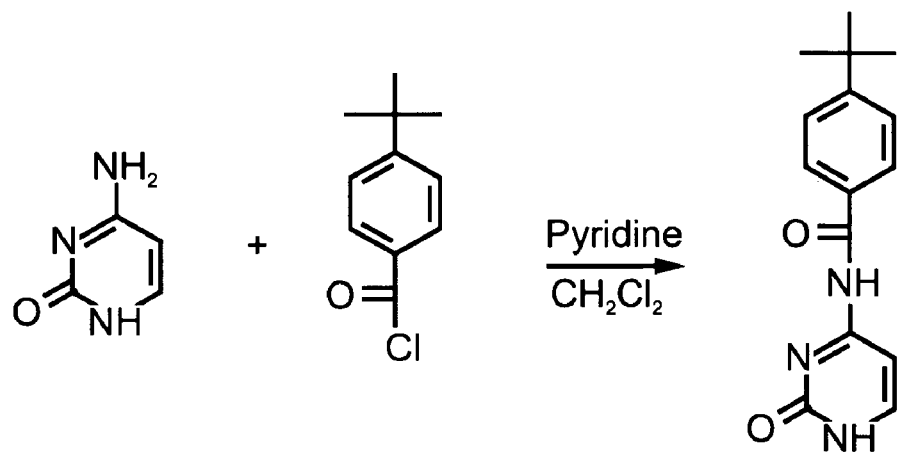
Figure 4B:
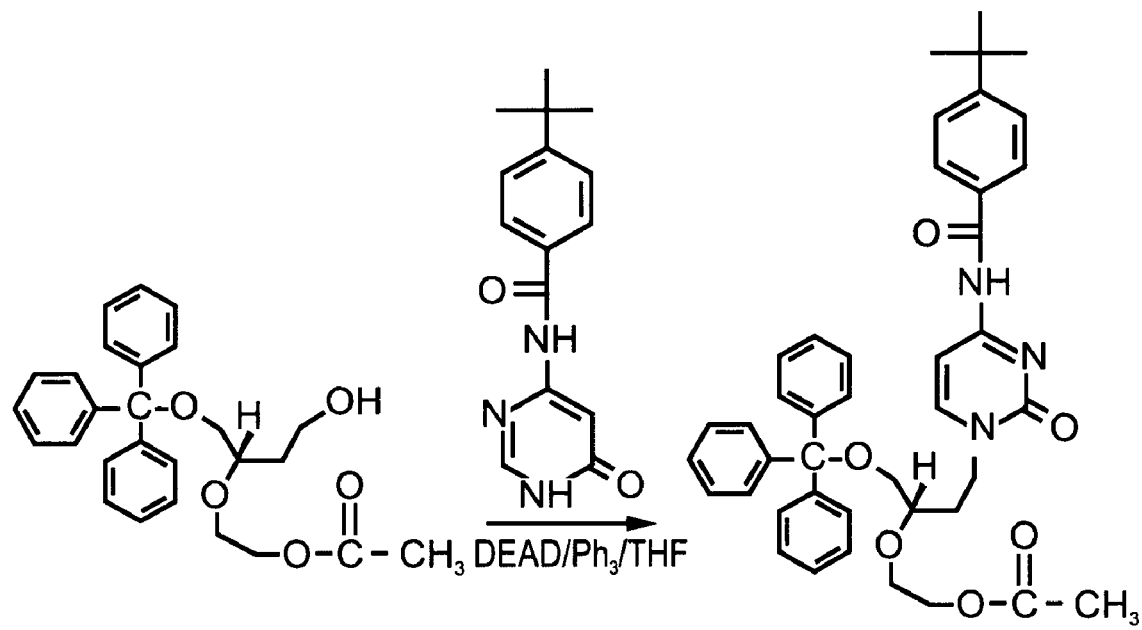

In another alternative, synthetic route B, the structure of the cytosine base remains intact. Synthetic route B of PEG-C is detailed hereinafter and is further schematically illustrated in FIGS. 4b(i)–(iv).

Preparation of 4-(1,1-Dimethylethyl)-N-[1,2-dihydro-2-oxo-4-pyrimidinyl]benzamide (Compound 25): To a suspension of cytosine (5.0 grams, 43 mmoles) in a mixture of 1:4 pyridine:dichloromethane (50 ml), tert-butylbenzoyl chloride (Aldrich) (10.6 ml, 56.6 mmoles) was added dropwise. The reaction mixture was stirred at room temperature for four hours and thereafter water (10 ml) and chloroform (40 ml) were added thereto with vigorous stirring. The resulting precipitates were thereafter collected and washed with water. The organic layer in the filtered solution was separated, washed with 1M HCl (30 ml×2) and brine (30 ml) and dried, immediately thereafter, over anhydrous sodium sulfate. The solution was then evaporated to remove about ⅔ of its volume. To the remaining solution (about 20 ml), hexanes (50 ml) were added and the combined precipitates were dried over P$_2$O$_5$, under high vacuum, for eight hours. 11.2 grams (92% yield) of Compound 25 were obtained.

m.p.: >260° C.

$^1$H-NMR (in DMSO-d6): δ=1.31 (9H, s), 7.22 (1H, br), 7.53 (2H, d, J=8.43 Hz), 7.87 (1H, d, J=7.08 Hz), 7.96 (2H, d, J=8.42 Hz) ppm.

Preparation of (S)-1-O-trityl-2-O-(acetoxy-ethanol)-4-(1, 1-dimethylethyl)-N-[1,2-dihydro-2-oxo-4-pyrimidinyl]benzamide-1,2,4-butanetriol (Compound 26): To a solution of Compound 9 (7.7 grams, 17.7 mmoles), prepared as described hereinabove, in dry THF (300 ml), Compound 25

(5.84 grams, 21.55 mmoles) and triphenylphosphine (Aldrich) (9.94 grams, 37.9 mmoles) were added, under argon atmosphere. The slurry mixture was vigorously stirred for 15 minutes at room temperature and thereafter diethyl azodicarboxylate (Aldrich) (5.96 ml, 37.9 mmoles) was added dropwise, during a period of 20 minutes. After the addition was completed, the slurry solution became clear and was stirred at room temperature for additional three hours. Thereafter, the solvent was evaporated to dryness and the residue was extracted with ethyl acetate (250 ml) and washed with water and brine. The organic layer was dried over sodium sulfate and the solvent was removed under reduced pressure. The resulting yellowish oily residue was purified by silica gel chromotography, using a mixture of 3:1 (v:v) ethyl acetate:hexane as eluent. 9.87 grams (81% yield) of Compound 26 were obtained as an oil.

TLC (3:1 ethyl acetate:hexane): Rf=0.44.

$^1$H-NMR (in $CDCl_3$): δ=1.34 (9H, s), 2.01 (2H, m), 2.05 (3H, s), 3.18 (2H, m), 3.38 (1H, m), 3.56 (2H, m), 3.96 (2H, m), 4.21 (2H m), 7.21–7.85 (21H, Ar—H) ppm.

Preparation of (S)-2-O-(acetoxy-ethanol)-4-(1,1-dimethylethyl)-N-[1,2-dihydro-2-oxo-4-pyrimidinyl]benzamide-1,2,4-butanetriol (Compound 27): A solution of Compound 26 (6.87 grams, 10 mmoles) in 50 ml dry pyridine and 50 ml acetic anhydride was heated to 100° C. for 30 minutes. After the reaction mixture was cooled, the solvents were evaporated to dryness and the residue, was extracted with ethyl acetate (250 ml) and washed with water and brine. The organic layer was thereafter dried over sodium sulfate and the solvent was removed under reduced pressure. The resulting oily residue was purified by silica gel chromatography, using a mixture of 9:1 (v:v) dichloromethane:methanol as eluent. 4.45 grams (100% yield) of Compound 27 were obtained as an oil.

TLC (9:1 ethyl acetate:methanol): Rf=0.50.

$^1$H-NMR (in $CDCl_3$): δ=1.40 (9H, s), 2.10 (2H, m), 2.15 (3H, s), 3.53–3.79 (2H, m), 3.85 (3H, m), 4.10 (2H, m), 4.30 (2H), 7.50–8.10 (6H, Ar—H), 9.01 (1H, br) ppm.

Preparation of (S)-1-Dimethoxytrityl-2-O-(acetoxy-ethanol)-4-(1,1-dimethylethyl)-N-[1,2-dihydro-2-oxo-4-pyrimidinyl]benzamide-1,2,4-butanetriol (Compound 28): Compound 27 (1.45 grams, 10 mmoles) was co-evaporated with dry pyridine (3×50 ml) and was thereafter dissolved in dry pyridine (100 ml). A solution of dimethoxytrityl chloride (4.05 grams, 11.9 mmoles) in dry pyridine (30 ml) was thereafter added dropwise, under argon atmosphere, at room temperature. After the addition was completed, the solvent was evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 0.5% pyridine in ethyl acetate as eluent. 7.20 grams (96% yield) of Compound 28 were obtained as an oil.

TLC (ethyl acetate): Rf=0.65.

$^1$H-NMR (in $CDCl_3$): δ=1.37 (9H, s), 1.97 (2H, m), 2.17 (2H, m), 2.12 (3H, s), 3.21 (2H, m), 3.45 (1H, m), 3.62 (1H, m), 3.83 (6H, s), 3.94 (1H, m), 4.06 (2H, m), 4.26 (2H, m), 6.85–7.89 (19H, Ar—H), 8.74 (1H, br) ppm.

Preparation of (S)-1-Dimethoxytrityl-2-O-(ethanol)-4-(,1,1-dimethylethyl)-N-[1,2-dihydro-2-oxo-4-pyrimidinyl]benzamide-1,2,4-butanetriol (Compound 29): To a cooled solution (0° C.) of Compound 28 (7.47 grams, 10 mmoles) in dry THF (100 ml), a solution of 1M of sodium methoxide in methanol (10 ml) was added dropwise. The reaction was monitored by TLC in ethyl acetate. After the reaction was completed, the solvent was evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 0.5% pyridine in ethyl acetate as eluent. 6.85 grams (97% yield) of Compound 29 were obtained as an oil.

TLC (ethyl acetate): Rf=0.25.

$^1$H-NMR (in $CDCl_3$): δ=1.38 (9H, s), 1.98 (2H, m), 3.28 (2H, m), 3.61 (2H, m), 3.79 (2H, m), 3.84 (6H, s), 4.07 (2H, m), 6.85–7.89 (19H, Ar—H), 8.74 (1H, br) ppm.

Preparation of (S)-1-Dimethoxytrityl-2-O-(ethoxy-methanesulfonyl)-4-(1,1-dimethylethyl)-N-[1,2-dihydro-2-oxo-4-pyrimidinyl]benzamide-1,2,4-butanetriol (Compound 30): Compound 29 (7.05 grams, 10 mmoles) was co-evaporated with dry pyridine and was thereafter dissolved in pyridine (150 ml). The solution was cooled to 0° C. (by means of an ice bath), methanesulfonylchloride (2.29 grams, 1.58 ml, 20 mmoles) was added thereto and the mixture was stirred for two hours at room temperature. The solvent was thereafter evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 0.5% pyridine in ethyl acetate as eluent. 5.78 grams (73% yield) of Compound 30 were obtained as an oil.

TLC (ethyl acetate): Rf=0.58.

A stock solution of Compound 30 (0.1 M) was prepared by dissolving the product prepared as described hereinabove in dry THF (73 ml), under argon atmosphere.

EXAMPLE 3

Preparation of a Thymine-PEG Monomer (PEG-T)

Figure 5A:
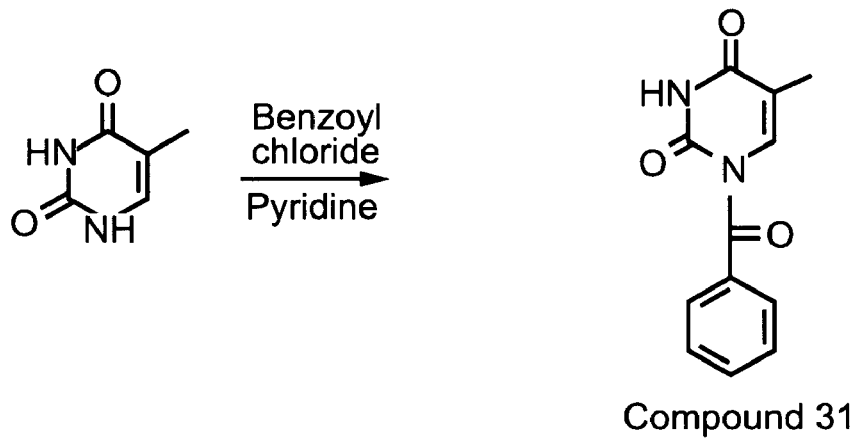
FIGS. 5(i)–(ii) illustrates the synthesis of a monomeric building block (PEG-T) of the present invention.
Figure 5A:
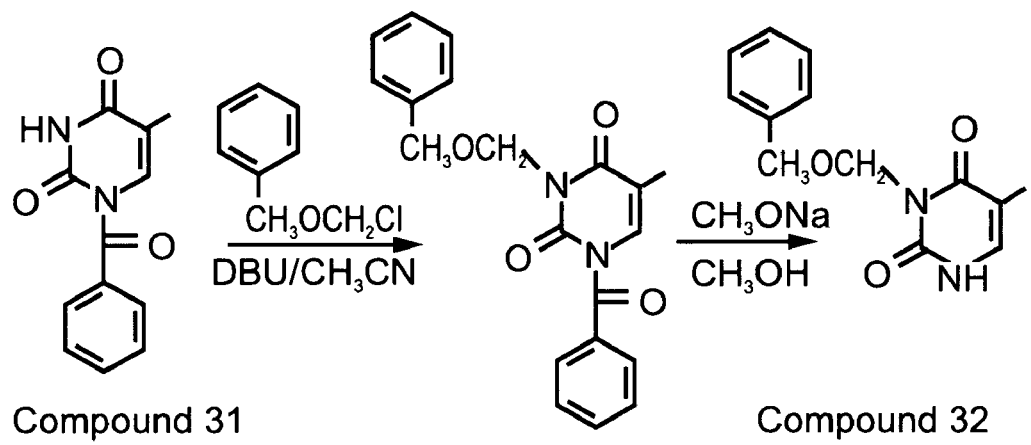
Figure 5A:
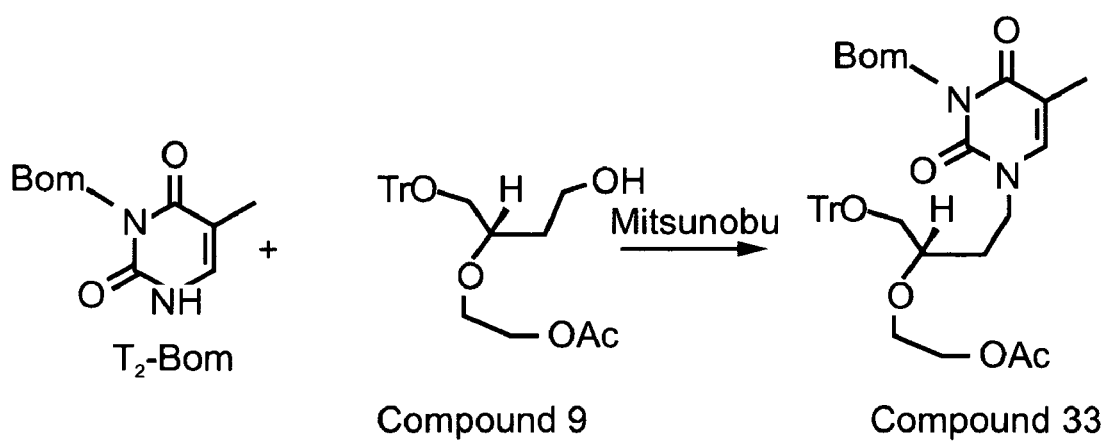

A thymine-PEG monomer (PEG-T) was prepared according to the processes described hereinafter. The preparation of PEG-T is further schematically illustrated in FIGS. 5(i)–(ii).

Preparation of 1-N-benzoylthymine (Compound 31): 1-N-benzoylthymine was prepared according to Cruikshank et al., Tetrahedron Letters (1984), 25, 681.

TLC (9:1 dichloromethane:methanol): Rf=0.55.

Preparation of 3-benzyloxymethythymine (Compound 32): To a solution of 1-benzoylthymine (Compound 31) (19.5 grams, 84.8 mmoles) in dry acetonitrile (200 ml, 1,8-diazabicyclo[5,4,0]undec-7-ene (DBU) (Aldrich) (15 m.) was added in one portion and 60% benzyloxymethyl chloride (Eom-chloride) (Aldrich) (23 ml) was added thereafter, under argon atmosphere. The reaction was stirred at room temperature for two hours. The solvent was then evaporated to dryness and the residue was extracted with ethyl acetate (250 ml) and washed with water and brine. The organic layer was dried over sodium sulfate, the solution was filtrated and concentrated to obtain a volume of 100 ml. Methanol (250 ml) was thereafter added to the solution and 27.8 grams (93.9% yield) of a white precipitate were formed [TLC (1:1 ethyl acetate:hexane): Rf=0.7].

To a suspension of the white precipitate prepared as described hereinabove (10 grams, 27 mmoles) in methanol (100 ml), a solution of 0.3M sodium methoxide (50 ml) was added and the reaction mixture was stirred at room temperature, while being monitored by TLC. The reaction was completed within 10 minutes and the Ph of the mixture was then adjusted to 7.0 by adding HCl 5N. The solvent was thereafter evaporated to dryness and the residue was triturated with ether (300 ml). The mixture was filtered and the filtrate was dried under reduced pressure. 6.2 grams (87.5% yield) of Compound 32 were obtained as a precipitate.

TLC (ethyl acetate): Rf=0.44.

$^1$H-NMR (in CDCl$_3$): δ=1.68 (3H, s), 4.59 (2H, s), 5.21 (2H, s), 6.41 (1H, s), 7.24–7.28 (Ar—H) ppm.

Preparation of (S)-1-trityl-2-O-acetoxy-ethanol)-4-(3'-benzyloxymethylthymidine)-1,2,4- butanetriol (Compound 33): To a stirred solution of Compound 32 (6.08 grams, 24.74 mmoles) in dry THF, Compound 9, prepared as described hereinabove, (9 grams, 20.73 mmoles) and triphenylphosphine (Aldrich) (11.40 grams, 43.5 mmoles) were added, under argon atmosphere. After 15 minutes, diethyl azodicarboxylate (Aldrich) (7.56 grams, 43.5 mmoles) was slowly added during a period of 30 minutes. The reaction mixture was thereafter covered with aluminum foil and was stirred at room temperature, under argon atmosphere, for 24 hours. The solvent was then evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 1:1 (v:v) ethyl acetate:hexane as eluent. 11.8 grams (86% yield) of Compound 33 were obtained as an oil.

TLC (1:1 ethyl acetate:hexane): Rf=0.53.

$^1$H-NMR (in CDCl$_3$): δ=1.87 (3H, s), 1.80–1.94 (2H, m), 2.03 (3H, s), 3.18 (2H, m), 3.3–3.5 (2H, m), 3.65–3.80 (3H, m), 4.21 (2H, m), 4.18 (2H, m), 4.67 (2H, s), 5.47 (2H, s), 6.93 (1H, s), 7.20–7.43 (Ar—H) ppm.

Preparation of (S)-1-Trityl-2-O-(ethanol)-4-(3'-benzyloxymethylthymidine)-1,2,4-butanetriol (Compound 34): To a solution of Compound 33 (6.62 grams, 10 mmoles) in methanol (100 ml), a solution of 1M sodium methoxide in methanol (15 ml, 15 mmoles) was added. The solution was stirred at room temperature for one hour The solvent was then evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 2:1 ethyl acetate:hexane as eluent. 6.11 grams (96.6% yield) of Compound 34 were obtained as an oil.

TLC (2:1 ethyl acetate:hexane): Rf=0.50.

$^1$H-NMR (in CDCl$_3$): δ=1.88 (3H, s), 1.80–1.90 (2H, m), 3.17 (2H, m), 3.45 (2H, m), 3.66–3.95 (5H, m), 4.68 (2H, s), 5.42 (2H, s), 7.02 (1H, s), 7.20–7.43 (Ar—H) ppm.

Preparation of (S)-1-trityl-2-O-(bromo-ethanol)-4(3'-benzyloxymethylthymidine)-1,2,4-butanetriol (Compound 35): To a solution of Compound 34 (2 grams, 3.2 mmoles) in dry DMF (50 ml), triphenylphosphine (1.68 grams, 6.4 mmoles) was added. CBr$_4$ (Aldrich) (2.12 grams, 6.4 mmoles) was added in portions thereto, during a period of 10 minutes. The solution was stirred at room temperature for 16 hours. The solvent was thereafter evaporated to dryness and the residue was extracted with ethyl acetate (250 ml) and washed with water and brine. The organic layer was dried over sodium sulfate and the solvent was removed under reduced pressure, The resulting oily residue was purified by silica gel chromatography, using a mixture of 1:1 (v:v) ethyl acetate: hexane as eluent. 2.01 grams (91% yield) of Compound 35 were obtained as an oil.

TLC (2:1 ethyl acetate:hexane): Rf=0.68.

$^1$H-NMR (in CDCl$_3$): δ=1.88 (3H, s), 1.80–1.90 (2H, m), 3.18 (2H, m), 3.47 (3H, m), 3.66 (1H, m), 3.79 (2H, m), 4.01 (1H, m), 4.62 (2H, s), 5.48 (2H, s), 7.04 (1H, s), 7.19–7.43 (Ar—H) ppm.

EXAMPLE 4

Preparation of an Acyclic Oligomer of PEG-T (OLIGO-PEG-T) in Solution

The preparation of an oligomer of PEG-T, which is also referred to herein as OLIGO-PEG-T, is described hereinafter and is further schematically illustrated in FIGS. 6(i)–(ii).

Preparation of (S)-1-trityl-2-O-(ethybenzylether)-4-(3'-benzyloxymethylthymidine)-1,2,4-butanetriol (Compound 36) and (S-2-O-(ethybenzyether)-4-(3'-benzyloxymethylthymidine)-1,2,4-butane triol (Compound 37): To a solution of Compound 34 (3.5 grams, 5.64 mmoles) in dry THF (20 ml), 60% NaH dispersed in oil (0.227 grams, 1.2 molequivalents of NaH) was added, under argon atmosphere. The slurry solution was stirred at room temperature for one hour and thereafter benzyl bromide (0.96 grams, 5.65 mmoles) was added. The reaction was stirred for 16 hours at room temperature. The solvent was then evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 1:1 (v:v) ethyl acetate:hexane as eluent. 3.88 grams (95.3% yield) of Compound 36 were obtained as an oil.

TLC (1:1 ethyl acetate:hexane): Rf=0.46.

To 3.88 grams (5.46 mmoles) of Compound 36, prepared as described hereinabove, a solution of 80% acetic acid in water was added and the mixture was stirred at 100° C. for one hour. The solvent was then evaporated to dryness and the residue was extracted with ethyl acetate (250 ml) and washed with water and brine. The organic layer was dried over sodium sulfate and the solvent was remover under reduced pressure. The resulting oily residue was purified by silica gel chromatography, using a mixture of (3:1) ethyl acetate:hexane as eluent. 2.85 grams (97.6% yield) of Compound 37 were obtained as an oil.

TLC (1:1 ethyl acetate:hexane): Rf=0.32.

$^1$H-NMR (in CDCl$_3$): δ=1.82 (3H, s), 1.87 (2H, m), 3.39 (1H, m), 3.49 (1H, m), 3.65 (2H, m), 3.67–3.86 (5H, m), 4.55 (2H, s), 4.69 (2H, s), 5.48 (2H, s), 7.05 (1H, s), 3.23–7.36 (10H, Ar—H) ppm.

Condensation of Compound 37 with Compound 35 to obtain the dimer-PEG-T: To a solution of Compound 37 (1 gram, 2.13 mmoles) in THF (50 ml), 60% NaH dispersed in mineral oil (0.102 grams, 1.2 molequivalents) was added in one portion, under argon atmosphere. The mixture was stirred for one hour and thereafter Compound 35 (2 grams, 2.92 mmoles) was added. The reaction mixture was refluxed for 16 hours. The solvent was then evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 1.5:1 ethyl acetate:hexane as eluent. 3.89 grams (85.1% yield)) of Compound 38 were obtained as an oil.

TLC (1.5:1 ethyl acetate-hexane). Rf=0.46.

$^1$H-NMR (in CDCl$_3$): δ=1.74 (3H, s), 1.68–2.04 (4H, m), 1.90 (3H, s), 3.17 (2H, m), 3.29 (1H, m), 3.43–3.63 (8H, m), 3.72–3.91 (6H, m), 4.53 (2H, s), 4.41 (4H, 2s), 5.48 (4H, m), 7.02 (1H, s), 7.05 (1H, s), 7.22–7.44 (30H, Ar—H) ppm.

Figure 6A:
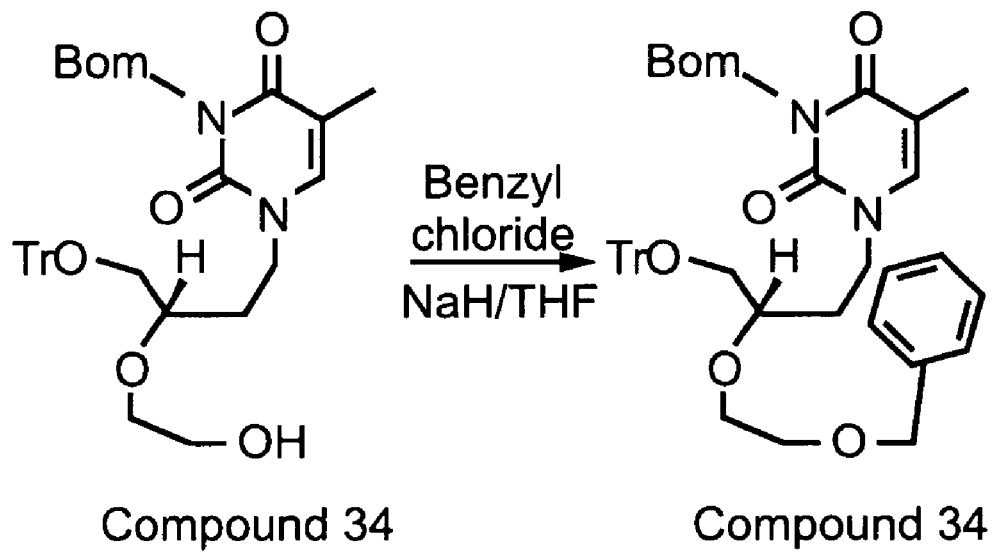
FIGS. 6(i)–(ii) illustrates the synthesis of a dimeric or oligomeric acyclic compound (dimer-PEG-T or oligo-PEG-T) of the present invention, in solution.
Figure 6A:
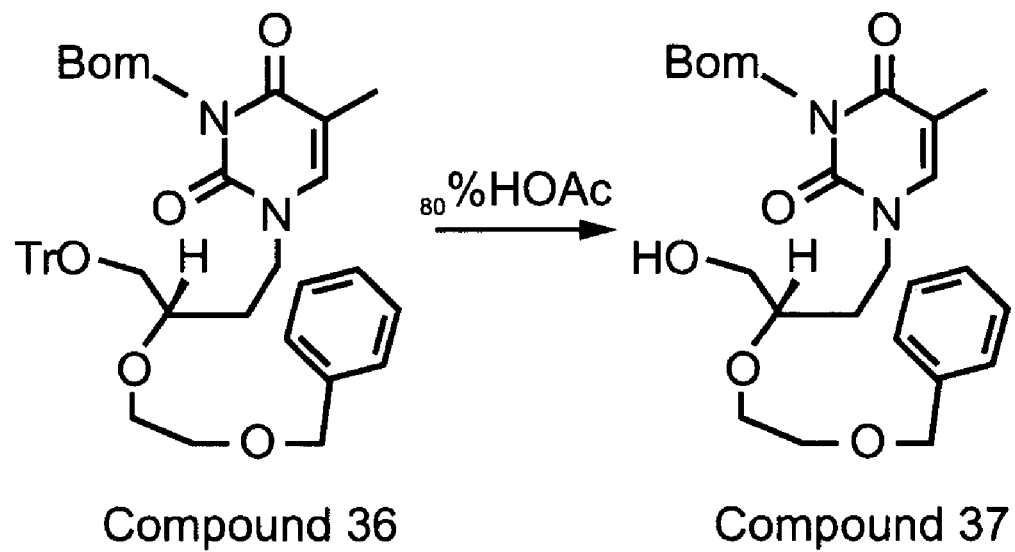

The removal of the protecting groups of Compound 38, so as to obtain a dimer of PEG-T, was performed by heating Compound 38 with 6N HCl at 95° C. for 6 hours, as is illustrated in FIG. 6 (I–II).

EXAMPLE 5

Preparation of an Oligomer of PEG-T (OLIGO-PEG-T) Using a Polymeric Support

The preparation of the oligomers of the present invention, using a polymeric support, is essential for sequential condensations. A preferred polymeric support in this respect, according to the present invention, is the Wang resin (Aldrich).

A representative example of preparing OLIGO-PEG-T attached to Wang resin is described hereinafter, and is further schematically illustrated in FIGS. 7a–e.

Figure 7A:
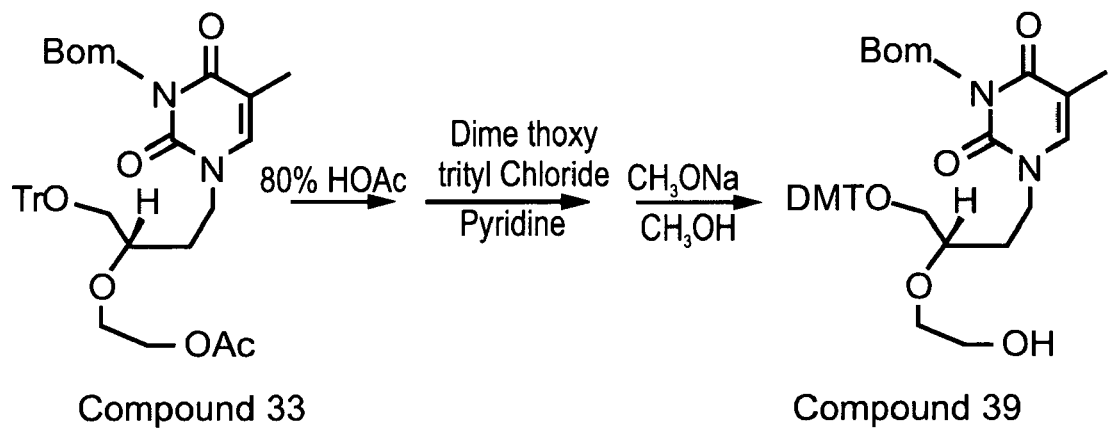
FIGS. 7a–7e illustrate a process of preparing an oligonucleotide (oligo-PEG-T) of the present invention, attached to a solid support.

Preparation of (S)-1-Dimethoxytrityl-2-O-(ethanol)-4-(3'-benzyloxymethylthymidine)-1,2,4-butanetriol (Compound 39): The preparation of Compound 39 is a modification of the process used in the preparation of Compound 34 (which is described in Example 4 and FIGS. 6(i)–(ii)). As is shown in FIG. 7a, the trityl protecting group in Compound 34 (6.62 grams, 10 mmoles) was replaced by a dimethoxytrityl protecting group and the resulting compound was reacted with sodium methoxide, according to the procedure described in Example 4. 5.91 grams (86.9% yield) of Compound 39 were obtained as a yellowish oil.

$^1$H-NMR (in CDCl$_3$): δ=1.88 (3H, s), 2.45 (1H, br), 3.15 (2H, m), 3.42 (2H, m), 3.76 (6H, s), 3.66–3.86 (5H, m), 4.68 (2H, s), 5.49 (2H, s), 6.82 (4H, d, J=8 Hz), 6.97 (1H, s), 7.19–7.4 (Ar—H) ppm.

Figure 7B:
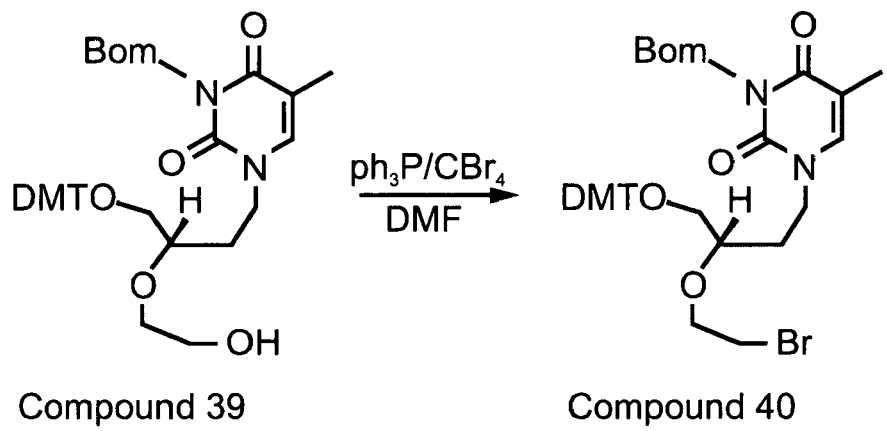

Preparation of (S)-1-dimethoxytrityl-2-O-(bromo-ethanol)-4-(3'-benzyloxymethylthymidine)-1,2,4-butanetriol (Compound 40): The preparation of Compound 40 is a modification of the process used in the preparation of Compound 35 (which is described in Example 4 and FIG. 6 (I–II). As is shown in FIG. 7b, the trityl protecting group in Compound 35 was replaced by a dimethoxytrityl protecting group and the resulting compound was reacted with triphenylphosphine and CBr$_4$ according to the procedure described in Example 4. 6.85 grams (92% yield) of Compound 39 were obtained.

$^1$H-NMR (in CDCl$_3$): δ=1.89 (3H, s), 1.83–1.97 (2H, m), 3.17 (2H, m), 3.47 (3H, m), 3.66 (1H, m), 3.77 (6H, s), 3.82 (2H, m), 4.01 (1H, m), 4.69 (2H, s), 5.48 (2H, s), 6.83 (4H, d, j=8 Hz), 7.03 (1H, s), 7.19–7.43 (14H, Ar—H) ppm.

Preparation of Compound 41 and Compound 42—Attachment of PEG-T (Compound 39) to Wang resin: To a solution of Compound 39 (0.5 grams, 0.735 mmoles) in THF (15 ml), 60% NaH dispersed in mineral oil (0.035 gram, 1.2 molequivalents) was added. The slurry mixture was agitated for one hour and thereafter Wang bromo resin (Aldrich), (0.319 gram, 0.379 mole milliequivalents of bromide) was added. The mixture was agitated for 16 hours at room temperature. The solid was then filtered and washed with methanol (20 ml) and dichloromethane (20 ml) and was thereafter treated with a solution of dry pyridine (5 ml) and acetic anhydride (5 ml). The mixture was agitated for 5 minutes and the solid was washed with methanol (10 ml) and dichloromethane (25 ml), to thereby obtain Compound 41, as is shown in FIG. 7c.

Figure 7C:
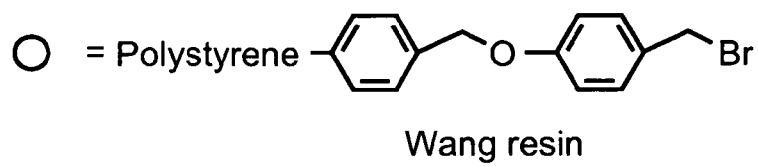
Figure 7C:
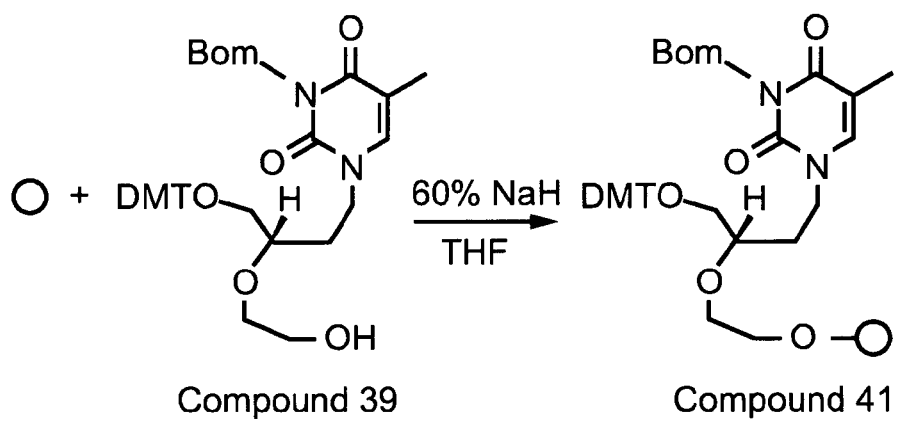
Figure 7C:
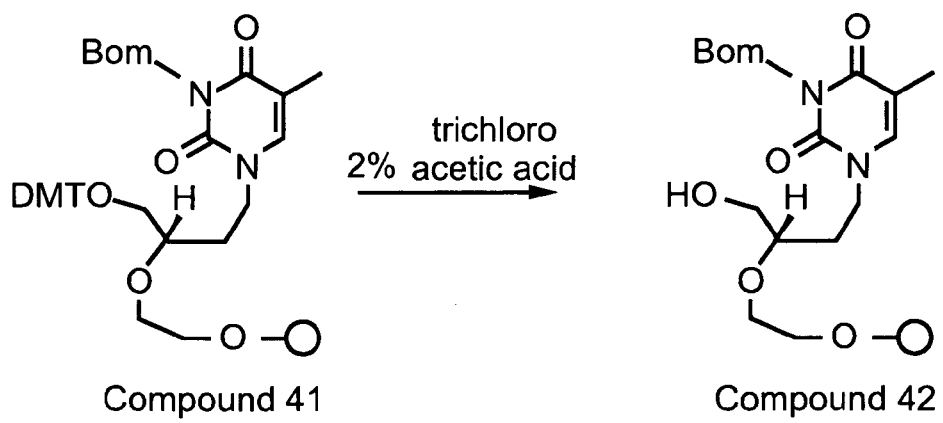

As is further shown in FIG. 7c, the removal of the dimethoxytrityl protecting group in Compound 41 was performed by treating the polymer with a solution of 2% of trichloroacetic acid in dichloromethane, to thereby obtain Compound 42. An intense pink color appeared. Calculations indicated that the yield of condensation was 92%.

Figure 7D:
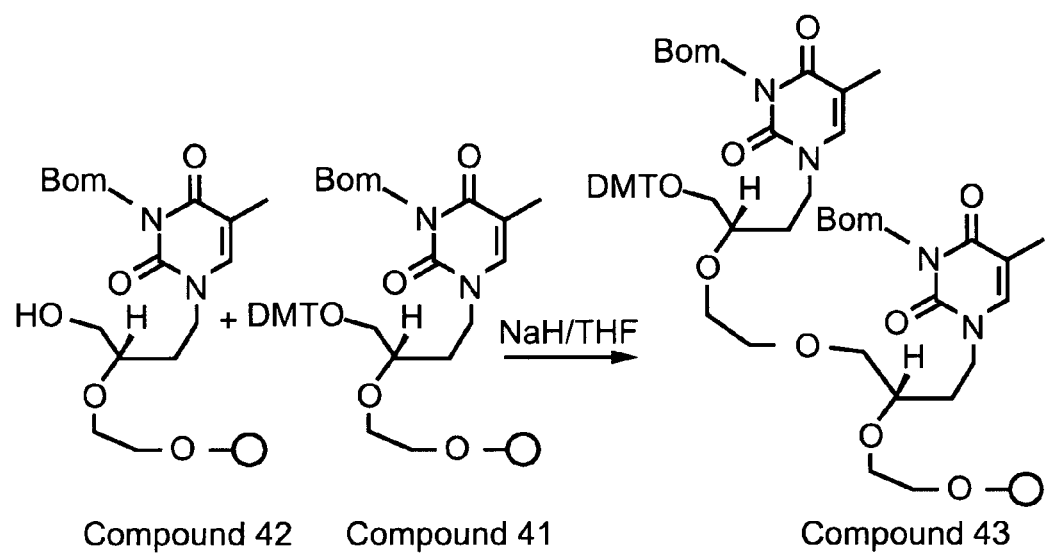
Figure 7D:
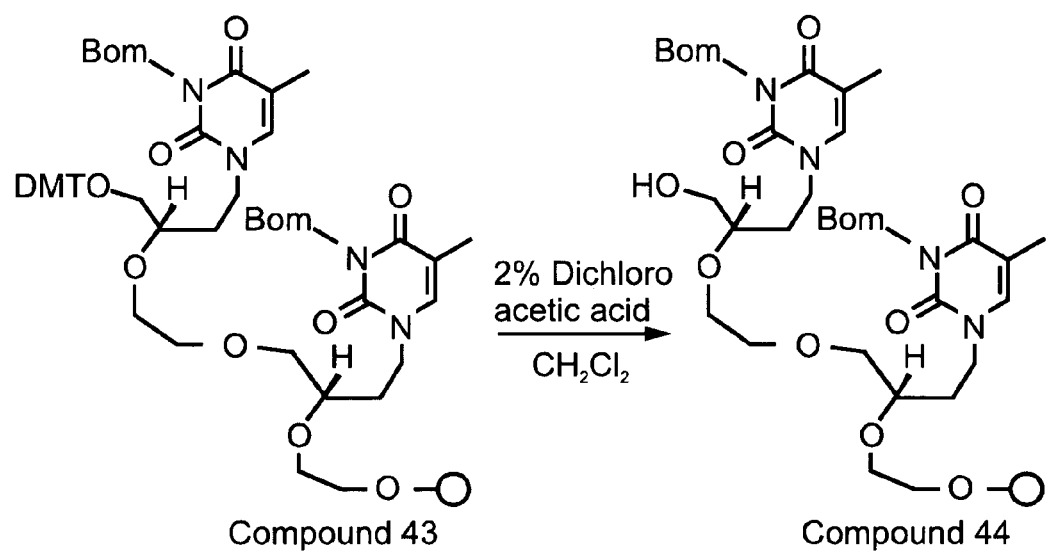
Figure 7E:
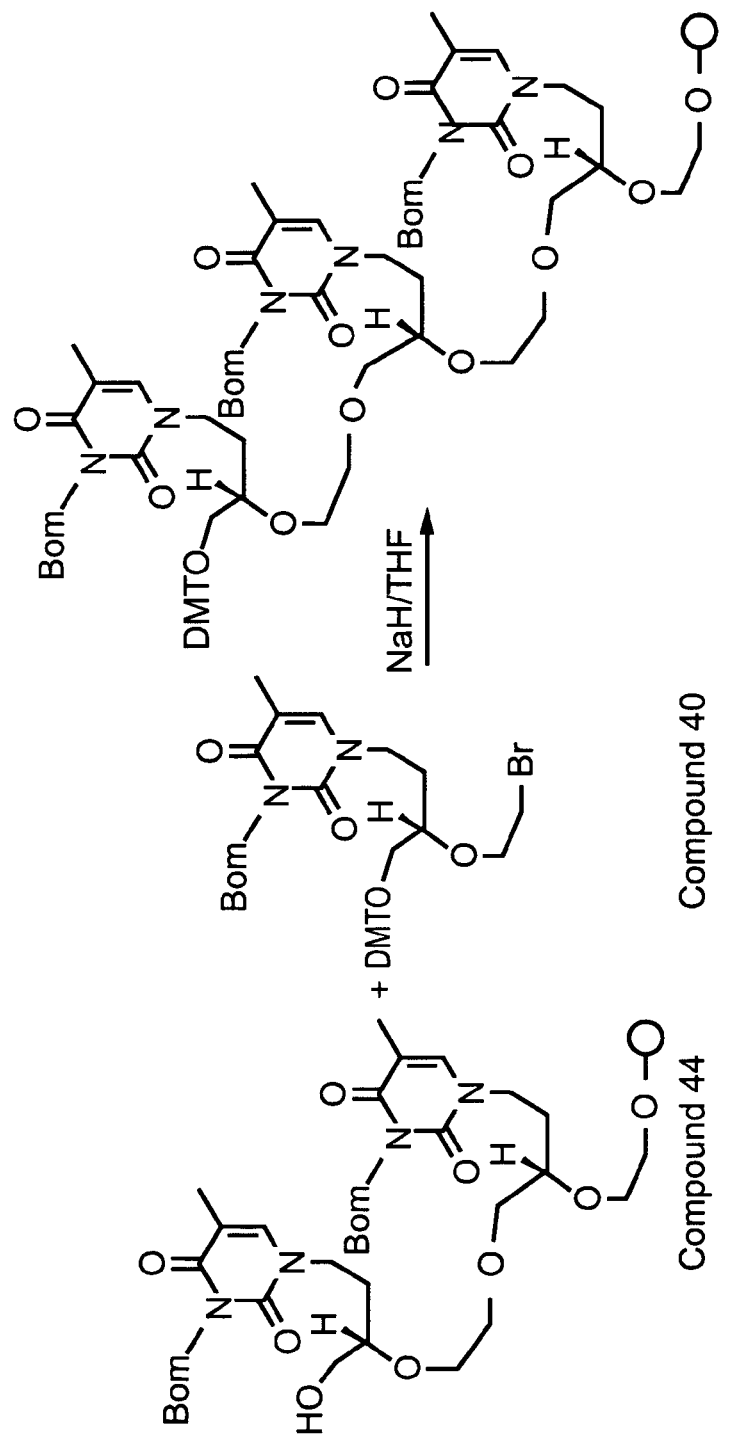

Preparation of Compounds 43, 44 and 45—an oligomer-PEG-T attached to Wang resin: As is shown in FIG. 7d, Compound 43 was prepared by reacting Compound 42 with Compound 40, according to the procedure described hereinabove for the preparation of Compound 41. The removal of the dimethoxytrityl protecting group was performed according to the procedure described hereinabove for the preparation of Compound 42, to thereby obtain Compound 44. Calculations indicated that the yield of condensation was 90%. Similarly, as is shown in FIG. 7e, Compound 44 was reacted with Compound 40, to thereby obtain Compound 45 in a condensation yield of 92%.

De-attachment of the OLIGO-(PEG-T) from the resin: The attached polymer was treated with 6N HCl (5 ml), at 95° C. for, 6 hours, the solution was thereafter filtrated and the filtrate was evaporated to dryness. The residue was dissolved in 1 ml double distilled water and the solution was loaded on a Sephadex G25 column (Pharmacia) (10 ml) and eluted with water. The fractions having a UV absorption at 254 nm were collected, quantitated and lyophilysed.

EXAMPLE 6

Cellular Uptake of Dimer-PEG-T

The cellular uptake of a dimeric acyclic compound of the present invention was demonstrated by first preparing a dimer-PEG-T labeled with a fluorescein and then testing the labeled compound for cellular uptake.

Figure 8A:
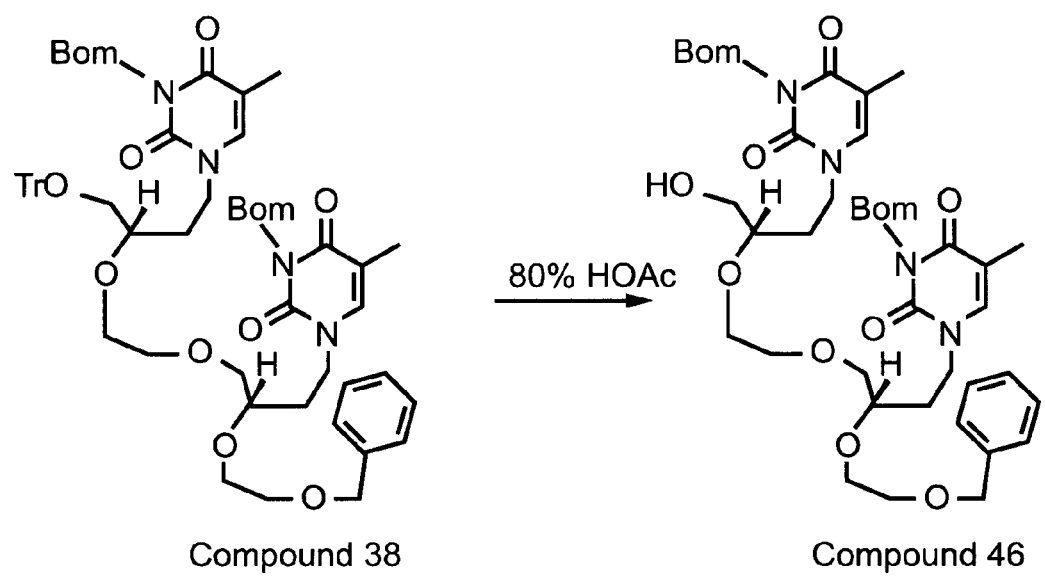
FIGS. 8a–b and 8c(i)–(iii) illustrate the synthesis of a labeled acyclic dimeric compound (fluorescein-dimer-PEG-T) of the present invention.
Figure 8A:
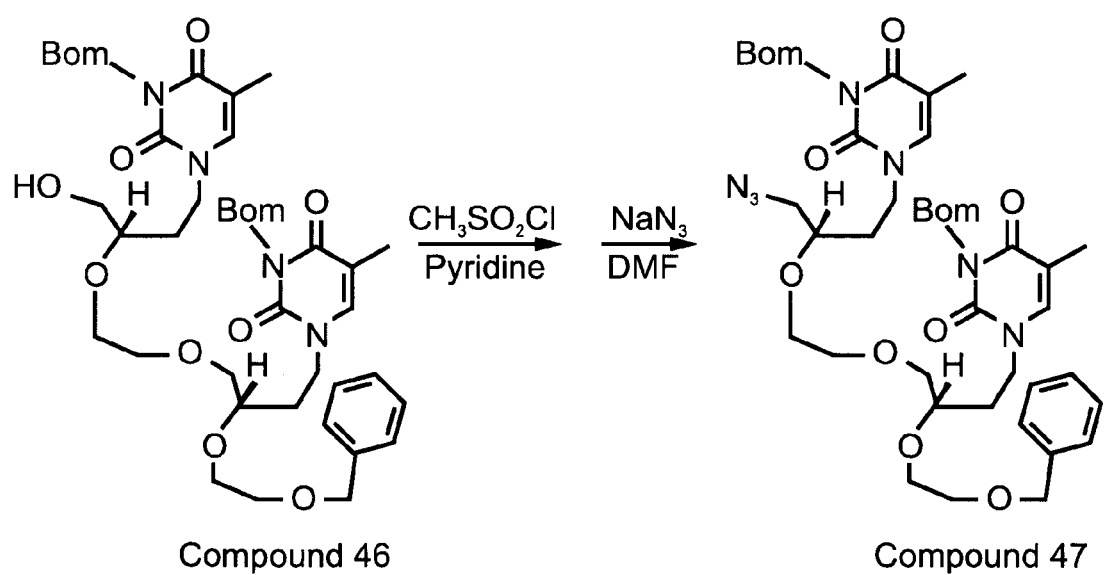

Labeling of dimer-PEG-T:

Preparation of Compound 47: Compound 38 (0.250 gram, 0.3 mmoles) was dissolved in 80% acetic acid and the solution was heated at 90° C. for 1 hour. The solvent was thereafter evaporated to dryness to thereby obtain Compound 46 (FIG. 8a), which was further used without purification. [TLC (ethyl acetate): Rf=0.312].

Compound 46 was dissolved in dry pyridine (4 ml), under argon atmosphere, mesyl chloride (28 μl, 1.2 molequivalents) was added and the mixture was stirred for one hour at room temperature. The solvent was thereafter evaporated to dryness and the residue was extracted with ethyl acetate (250 ml) and washed with water and brine. The organic layer was dried over sodium sulfate and the solvent was removed under reduced pressure. The resulting oily residue was further used without purification. [TLC (ethyl acetate): Rf=0.41].

The oily residue was dissolved in DMF (10 ml), sodium azide (2 molequivalents) was added thereafter and the reaction mixture was heated at 80° C. for four hours. The solvent was then evaporated to dryness and the residue was extracted with ethyl acetate (25 ml) and washed with water and brine. The organic layer was dried over sodium sulfate and the solvent was removed under reduced pressure, to thereby obtain Compound 47 (FIG. 8a) as an oily residue, which was further used without purification. [TLC (ethyl acetate): Rf=0.62].

Figure 8B:
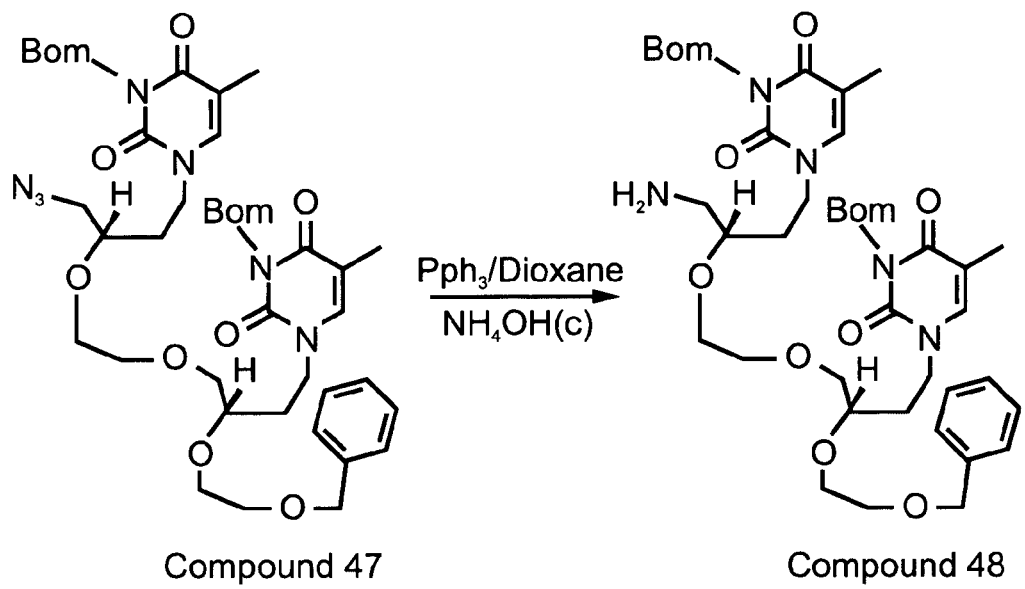
Figure 8B:
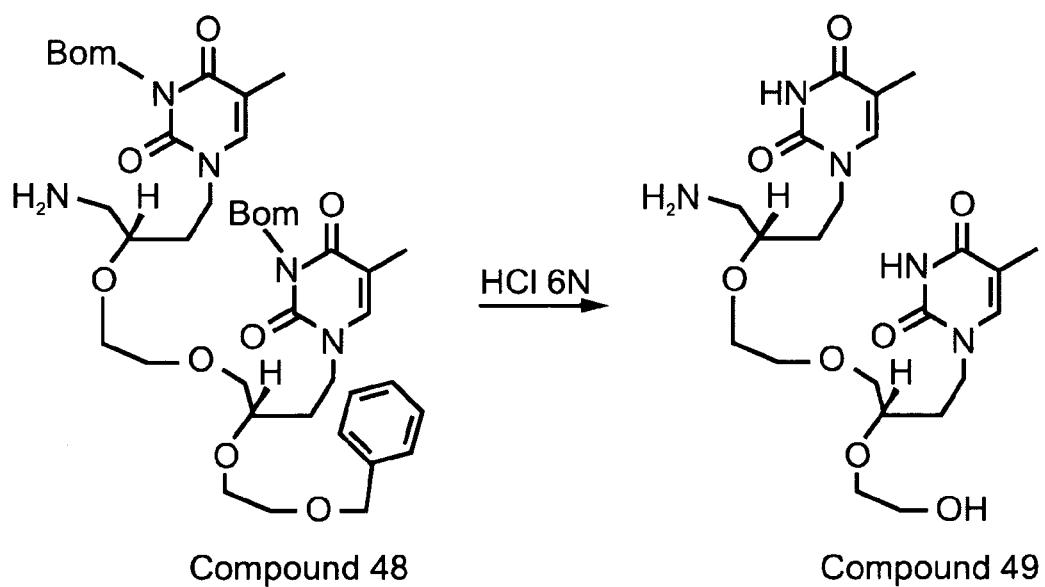

Preparation of Compound 49: Compound 47 was dissolved in dioxane (2 ml) and a mixture of triphenylphosphine (0.150 gram) and concentrated ammonium hydroxide (1.4 ml) was added thereto. The reaction mixture was stirred at room temperature for three hours and the product was thereafter purified by silica gel chromatography, using a mixture of 5% methanol in methylene chloride as eluent. 0.182 gram (72% yield) of Compound 48 (FIG. 8b) were obtained. [TLC (95:5 ethyl acetate,:methanol): Rf=0.14].

A solution of 6N HCl (20 ml) was thereafter added to 0.180 gram of Compound 48 and the reaction mixture was stirred at 90° C. for six hours. The solvent was then evaporated to dryness, the residue was re-dissolved in methanol and was purified by silica gel chromatography, using a mixture of 4:1 (v:v) dichloromethane:methanol as eluent. 0.100 gram of Compound 49 (FIG. 8b) were obtained as a white solid. [TLC (4:1 CH$_2$Cl$_2$:MeOH): Rf=0.1].

Figure 8C:
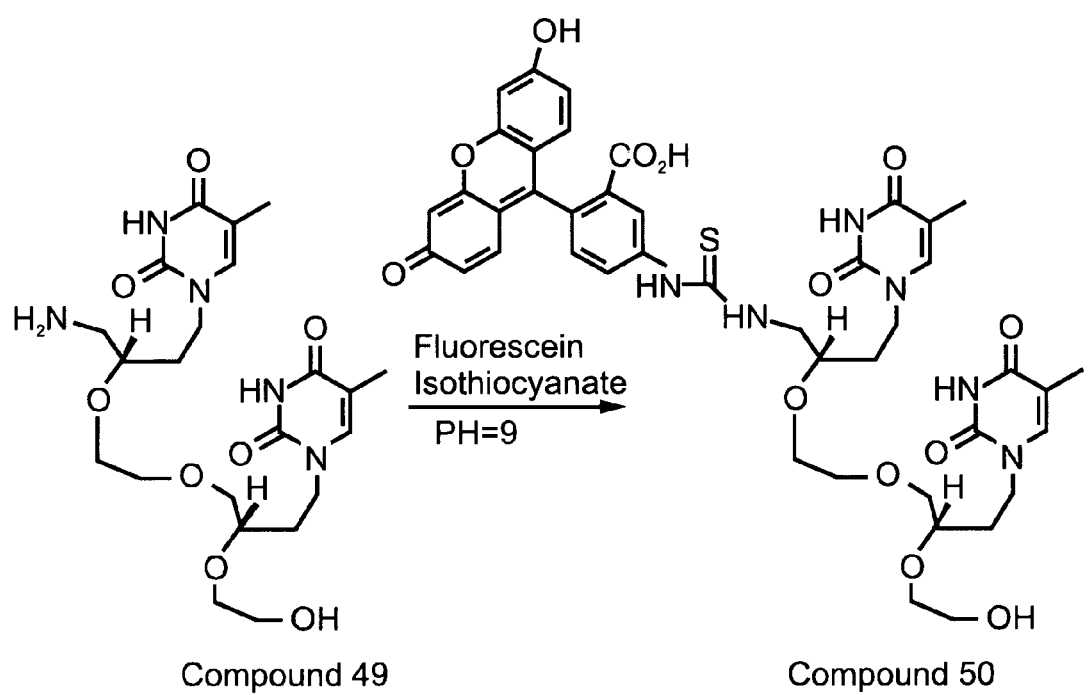

Preparation of Compound 50: Compound 49 (0.100 gram) was dissolved in sodium carbonate buffer having a pH=9 (0.5 ml) and a solution of fluorescein isothiocyanate (Aldrich) (0.100 gram) it DMF (0.5 ml) was added thereto. The reaction mixture was covered with aluminum foil and stirred for 16 hours at room temperature. The solvent was then evaporated to dryness and the residual oil (crude Compound 50, FIG. 8c) was further used in the protection and purification procedures that follows without purification.

To a solution of crude Compound 50 in dry pyridine (10 ml), an excess of pivaloyl chloride (Aldrich) (1 ml) was added and the reaction mixture was stirred for 16 hours at room temperature. The solvent was then evaporated to dryness and the residue was extracted with ethyl acetate (50 ml) and washed with water and brine. The organic layer was dried over sodium sulfate and the solvent was removed under reduced pressure. The resulting oily residue was purified by silica gel chromatography, using a mixture of 4:1 (v:v) dichloromethane:methanol as eluent, 0.042 gram of Compound 51 (FIG. 8c) were obtained as an oil.

TLC (4:1 dichloromethane:methanol): Rf=0.36.

$^1$H-NMR (in CDCl$_3$): δ=1.01 (9H, s), 1.19 (9H, s), 1.30 (18H, s), 1.34 (9H, s), 1.93 (6H, s), 3.4–4.2 (18H, m), 6.65–7.64 (11H, Ar—H) ppm.

The purified Compound 51 (0.030 gram) was dissolved in methanol (10 ml) and a solution 1M sodium methoxide in methanol (2 ml) was added thereto. The reaction mixture was covered with an aluminum foil and stirred for three hours. The solvent was then evaporated to dryness and the residue was re-dissolved in double distilled water, loaded on a Sephadex G25 column (Pharmacia) (10 ml) and eluted with double distilled water. Purified Compound 50 (the fluoresceinated dimer, FIG. 8c) was collected and lyophilized.

Uptake of dimeric PEG-T and monomeric PEG-T compounds by cells; Three plates, each of 12 wells, were seeded with 200×10$^3$ osteosarcoma cells per well on a rounded cover glass: were grown at 37° C. and were supplemented with 8% CO$_2$ for overnight.

Cells at their logarithmic phase were washed twice with serum-free medium containing L-glutamin and antibiotics and were thereafter treated with 1 ml of a PEG-antisense of the present invention, diluted in the same medium, for various incubation times. The cells were thereafter washed twice with 2 ml ice-cold phosphate buffer saline (PBS) (Sigma) and were fixed with 1 ml of fixation solution (2% formaldehyde in PBS) for 10 minutes. The cells were than washed with 2 ml of ice-cold PBS, mounted over glass slide with mounting solution (50% PBS and 50% glycerol) and were sealed with nail polish.

Figure 9:
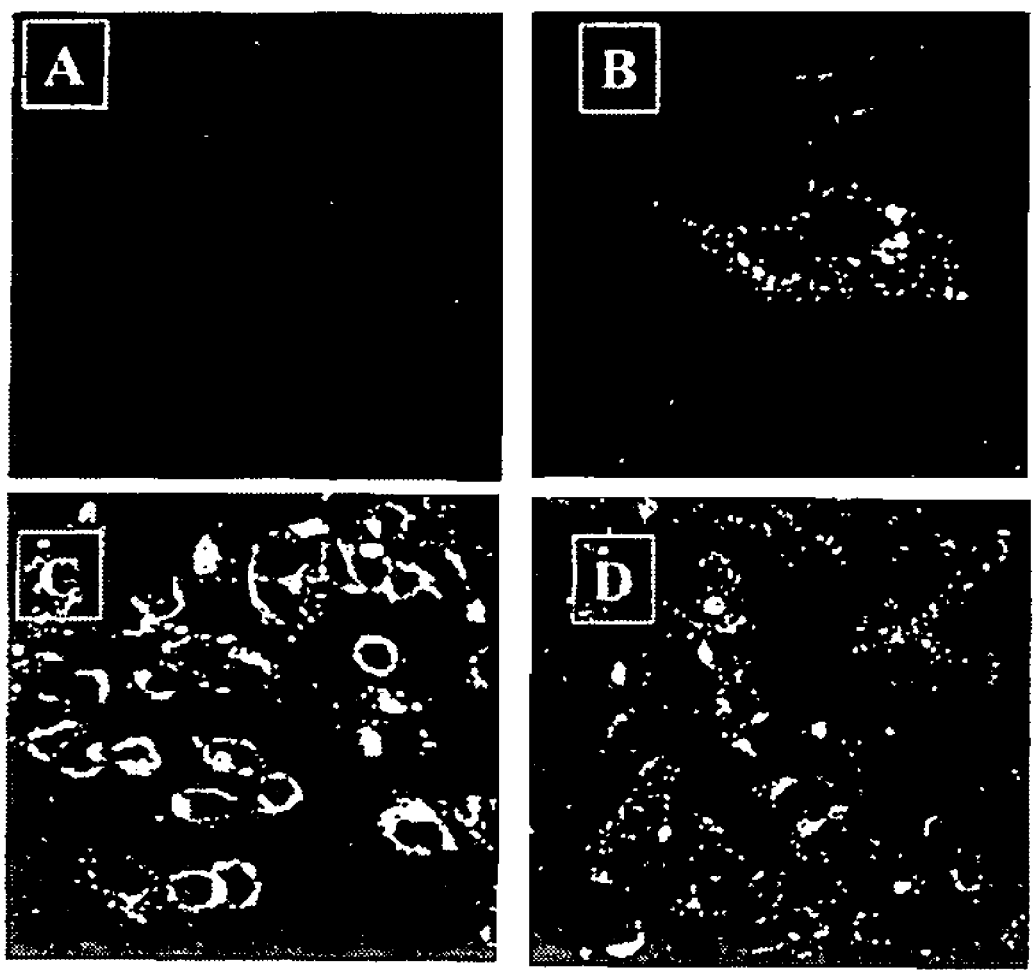
FIGS. 9a–d show images of osteosarcoma cells treated by (a) a 10 µM solution of a mixture of labeled monomeric and dimeric acyclic compounds (PEG-T) of the present invention, for a 30 minutes incubation time (FIG. 9a); (b) a 10 µM solution of a labeled acyclic monomeric compound (fluorescein-PEG-T) of the present invention, for a 30 minutes incubation time (FIG. 9b); (c) a 10 µM solution of a labeled acyclic dimeric compound (fluorescein-dimer-PEG-T) of the present invention, for a 30 minutes incubation time; and by (d) a 10 µM solution of an unlabeled dimeric acyclic compound (PEG-T) of the present invention, for a 15 minutes incubation time, followed by a 10 µM solution of a labeled acyclic dimeric compound (fluorescein-PEG-T) of the present invention, for a 30 minutes incubation time.

As is shown in FIGS. 9a–d, the image obtained for the cell penetration of a mixture of unlabeled monomeric and dimeric PEG-T, according to the present invention, after an incubation time of 30 minutes shows no detection of cell penetration by this mixture (FIG. 9a). The image obtained for the cell penetration of a labeled monomeric PEG-T after an incubation time of 30 minutes shows limited detection of cell penetration by this compound (FIG. 9b) and the image obtained for the cell penetration of a labeled dimeric PEG-T after an incubation time of 30 minutes shows enhanced detection of cell penetration by this compound (FIG. 9c). In a competitive experiment (FIG. 9d), the cells were incubated for 15 minutes with unlabeled dimeric PEG-T and for 30 minutes with labeled dimeric PEG-T. The image obtained in this experiment shows reduced detection of cell penetration by these compounds, as compared with the detection of cell penetration by the labeled dimeric compound.

EXAMPLE 7

Preparation of a Cyclic Dimeric Compound Described by the Formula VI

A representative example for the preparation of a compound described by the formula VI (Compound 65), according to the present invention, is described hereinafter and is further schematically illustrated in FIG. 10(i)–(iv).

Preparation of the Starting Materials:

Preparation of methyl pentenoate: To a solution of 4-pentenoic acid (Aldrich) (10 grams, 100 moles) in CCl$_4$ (30 ml) and methanol (20 ml), p-toluenesulfonic acid (0.5 gram) was added and the reaction mixture was refluxed for ten hours. After cooling, the reaction mixture was diluted with dichloromethane (300 ml) and washed with saturated sodium bicarbonate and brine. The organic phase layer was thereafter dried over anhydrous sodium sulfate, filtered and distilled through a short Vigreux column. 8.91 grams (78% yield) of the product as a colorless liquid were obtained.

b.p.=122–125° C.

$^1$H-NMR (in CDCl$_3$): δ=2.42 (4H, m), 3.71 (3H, s), 5.05 (2H, m), 5.85 (1H, m) ppm.

This process is briefly described by:

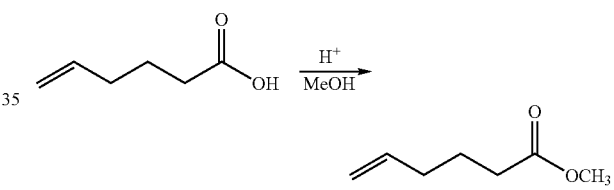

Preparation of 5-iododimethoxypyrimidine (Compound 52): The preparation of Compound 52 was performed according to Wada et al, Synthesis (1986), 555. Equimolar amounts of N-chlorosuccinimide (3.1 grams, 23 mmoles) and sodium iodide (3.4 grams, 23 mmoles) were dissolved separately in dry acetone (40 ml) and mixed together at room temperature. The obtained solution was stirred for 10 minutes and the produced sodium chloride precipitate was filtered. The solvent (acetone) was then removed completely under reduced pressure and the resulting residue was dissolved in acetic acid (30 ml) and was thereafter reacted with 2,4-dimethoxypyridine (3.22 grams, 23 mmoles), which was prepared according to Zorbach et al., in "Synthetic Procedures in Nucleic Acid Chemistry" vol. 1, Interscience Publishers, New York, (1968), 83.], at 80° C. The reaction mixture was stirred for two hours and then poured into ice-water (100 ml) and extracted with chloroform (3×30 ml). The combined extractions were successively washed with aqueous saturated sodium carbonate (80 ml), sodium thiosulfate (80 ml) and sodium chloride (80 ml) solution. The organic chloroform layer was dried over sodium sulfate and was concentrated under reduced pressure. The residue was purified by silica gel chromatography, using a mixture of 2:1 chloroform:hexane as element. 4.89 grams (80% yield) of Compound 52 were obtained.

$^1$H-NMR (in CDCl$_3$): δ=3.96 (3H, s), 4.01 (3H, s), 8.43 (1H, s) ppm.

This process is briefly described by:

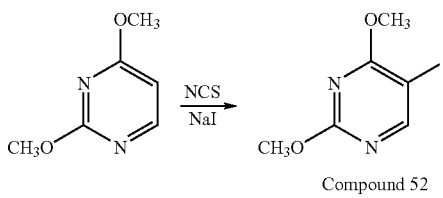

Compound 52

Preparation of 5-pentenoate-dimethoxypyrimidine (Compound 53): To a mixture of Compound 52 (16 grams, 60.1 mmoles), methyl pentenoate (27.58 grams, 242 mmoles) and triphenylphosphine (2.2 grams, 8.4 mmoles), potassium carbonate (20.5 grams, 148 mmoles), n-Bu4NHSO4 (20.5 grams, 60.4 mmoles) and palladium acetate (0.950 gram, 0.007 equivalents) were added with intensive stirring. The reaction mixture was further stirred, at room temperature, for 90 hours. The obtained residue was extracted with ethyl acetate (3×300 ml) an washed with water and brine. The organic layer was denied over sodium sulfate and then solvent was removed under reduced pressure. The resulting oily residue was purified by silica gel chromatography, using a mixture of 2:1 hexane:ethyl acetate as eluent. 8.23 grams of Compound 53 (54.5% yield) were obtained as an oil.

TLC (2:1 hexane:ethyl acetate): Rf=0.36.

$^1$H-NMR (in CDCl$_3$): δ=2.52 (4H, m), 3.70 (3H, s), 3.99 (3H, s), 4.007 (3H, s), 6.26 (1H, m), 6.39 (1H, m), 8.20 (1H, s) ppm.

Preparation of Compound 54: To a mixture of Compound 52 (16 grams, 60.1 mmoles), thifluoroacetamido-3-butenoate (38 grams, 242 mmoles), triphenylphosphine (2.2 grams, 8.4 mmoles), potassium carbonate (20.5 grams, 148 mmoles), n-Bu$_4$NHSO$_4$ (20.5 grams, 60.4 mmoles) and palladium acetate (0.950 gram, 0.007 equivalents) were added with intensive stirring. The reaction mixture was further stirred, at room temperature, for 90 hours. The obtained residue was extracted with ethyl acetate (3×300 ml) and washed with water and brine. The organic layer was dried over sodium sulfate and the solvent was removed under reduced pressure. The resulting oily residue was purified by silica gel chromatography, using a mixture of 2:1 hexane:ethyl acetate as eluent. 9.22 grams of Compound 54 (50.2% yield) were obtained as an oil.

TLC (2:1 hexane:ethyl acetate): Rf=0.30.

$^1$H-NMR (in CDCl$_3$): δ=2.32 (2H, m), 3.41 (2H, m), 3.99 (3H, s), 4.007 (3H, s), 6.26 (1H, m), 6.39 (1H, m), 8.20 (1H, s) ppm.

Preparation of 5-methylpentenoate-4-methoxypyrimidine (Compound 55). Compound 53 (5.96 grams, 23.69 mmoles) and acetyl chloride (50 grams, 637 mmoles) were stirred for 20 hours. The solvent was then evaporated to dryness and the residue was purified by silica gel chromatography, using a mixture of 1:19 methanol:chloroform as eluent. 4.48 grams of Compound 55 (80% yield) were obtained as an oil.

TLC (2:1 methanol:chloroform): Rf=0.30.

$^1$H-NMR (in CDCl$_3$): δ=2.45 (4H, m), 3.39 (3H, s), 3.68 (3H, s), 6.15 (1H, m), 6.48 (1H, m), 7.15 (1H, s) ppm.

Preparation of (S)-1-trityl-2-O-(acetoxy-ethanol)-4-(4-methoxy-5-methylpentenoatepyrimidine)-1,2,4-butanetriol (Compound 56): To a solution of Compound 9 (7.7 grams, 17.7 mmoles) in dry THF (300 ml), Compound 55 (5.12 grams, 21.55 mmoles) and triphenylphosphine, (Aldrich) (9.94 grams, 37.9 mmoles) were added, under argon atmosphere. The slurry mixture was vigorously stirred for 15 minutes at room temperature and thereafter diethyl azodicarboxylate (Aldrich) (5.96 ml, 37.9 mmoles) was added dropwise during a period of 20 minutes. After the addition was completed, the slurry solution became clear and was stirred at room temperature for additional three hours. The solvent was then evaporated to dryness and the residue was extracted with ethyl acetate (250 ml) and washed with water and brine. The organic layer was dried over sodium sulfate and the solvent was removed under reduced pressure, The resulting yellowish oily residue was purified by silica gel chromatography, using a mixture of 3:1 ethyl acetate:hexane as eluent. 9.39 grams (81% yield) of Compound 56 were obtained as an oil.

Preparation of (S)-1-Trityl-2-O-(mesyl-ethanol)-4-(4-methoxy-5-methylpentenoatepyrimidine)-1,2,4-butanetriol (Compound 57): To a solution of Compound 56 (6.54 grams, 10 mmoles) in dry methanol (50 ml), 0.1 M of sodium methoxide in methanol (15 ml, 1.5 mmoles) was added. The reaction mixture was stirred for one hour at room temperature and was being monitored by TLC using a mixture of 2:1 ethyl acetate:hexane (Rf=0.5). After the reaction was completed, the solvent was evaporated to dryness and the residue was extracted with ethyl acetate (250 ml) and washed with water and brine. The organic layer was dried over sodium sulfate and the solvent was removed under reduced pressure. The resulting yellowish oily residue was further used without purification. The dried residue was dissolved in dry pyridine (50 ml) and methanesulfonyl chloride (1.36 grams, 0.92 ml, 1.2 equivalents) was injected thereto at once, under argon atmosphere. The reaction mixture was stirred for three hours, while being monitored by TLC. After all the starting materials were consumed, the solvent was evaporated to dryness and the residue was extracted with ethyl acetate (250 nml) and washed with water and brine. The organic layer was dried over sodium sulfate and the solvent was removed under reduced pressure The resulting oily residue was further without purification.

Preparation of (S)-1-Trityl-2-O-(pivaloyl-ethanol)-4-(4-methoxybenzyl)-1,2,4-butanetriol (Compound 58): To a solution of dry pyridine (50 ml) and pivaloyl chloride (50 ml), Compound 7 (5.12 grams, 10 mmoles) was added and the reaction mixture was stirred at room temperature for two hours. The solvents were thereafter evaporated under reduced pressure and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 1:1 ethyl acetate:hexane as eluent. 5.5 grains (92% yield) of Compound 58 were obtained as an oil.

TLC(1:2 ethyl acetate:hexane): Rf=0.50.

$^1$H-NMR (in CDCl$_3$): δ=1.23 (9H, s), 1.27–1.47 (2H, m), 2.95 (2H, m), 3.24–3.49 (5H, m), 3.60 (3H, s), 4.00 (2H, m), 4.18 (2H, s), 6.65–7.28 (19H, Ar—H) ppm.

Preparation of (S)-2-O-(pivaloyl-ethanol)-4-(4-methoxybenzyl)-1,2,4-butanetriol (Compound 59): A solution of Compound 58 (6 grams, 10 mmoles) in a mixture of 80% acetic acid in water was heated at 100° C. for 30 minutes. The solvent was thereafter evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 3:1 ethyl acetate:hexane as eluent. 3.42 grams (96.6% yield) of Compound 59 were obtained as an oil.

$^1$H-NMR (in CDCl$_3$): δ=1.23 (9H, s), 1.27–1.47 (2H, m), 3.32 (1H, m), 3.39 (2H, m), 3.66–3.79 (2, H, m), 3.80 (3H, s), 4.06 (2H, s), 4.43 (2H, s), 6.38–7.25 (4H, Ar—H) ppm.

Preparation of Compound 60: To a solution of Compound 59 (3.5 grams, 10 mmoles) in dry THF (20 ml), 60% NaH dispersed in oil (0.402 gram, 1.2 equivalents of NaH) was added, under argon atmosphere. The slurry solution was stirred at room temperature for one hour and thereafter benzyl bromide (10.35 grams, 15 mmoles) was added thereto. The reaction mixture was stirred for 16 hours at room temperature. The solvent was then evaporated to dryness and the residue was extracted with ethyl acetate (250 ml) and washed with water and brine. The organic layer was dried over sodium sulfate and the solvent was removed under reduced pressure. The resulting oily residue was purified by silica gel chromatography, using a mixture of 1:1 ethyl acetate:hexane as eluent. 8.54 grams (90% yield) of Compound 60 were obtained as an oil.

$^1$H-NMR (in CDCl$_3$): δ=1.23 (9H, s), 1.27–1.47 (2H, m), 1.58–1.78 (2H, m), 1.91 (2H, m), 2.37 (2H, m), 2.84 (1H, m), 3.13–3.33 (4H, m), 3.22 (3H, m), 3.49 (2H, m), 3.56 (3H, s), 3.80 (3H, s), 4.06 (2H, m), 4.43 (2H, s), 6.46 (1H, m), 7.35 (1H, m), 7.22–7.33 (19H, Ar—H), 9.24 (1H, s) ppm.

Preparation of Compound 61: To a cooled (5° C.) solution of Compound 60 (9.49 grams, 10 mmoles) in a mixture of dichloromethane (200 ml) and water (10 ml), 2,3-dichloro-5,6-dicyano-1,4-benzoquinone (DDQ) (Aldrich) (2.9 grams, 12.7 mmoles) was added and the cooled reaction mixture was stirred for 30 minutes. The mixture was then extracted with 2×50 ml of 5% solution of sodium bicarbonate, followed by 2×200 ml of brine and was dried over anhydrous sodium sulfate. The solvent was removed under reduced pressure and the resulting oily residue was purified by silica gel chromatography, using a mixture of 1:1 ethyl acetate:hexane as eluent. 7.46 grams (90% yield) of Compound 61 were obtained as an oil.

$^1$H-NMR (in CDCl$_3$): δ=1.23 (9H, s), 1.27–1.47 (2H, m), 1.58–1.78 (2H, m), 1.91 (2H, m), 2.37 (2H, m), 2.99 (1H, s), 3.13–3.33 (4H, m), 3.23 (3H, m), 3.49 (2H, m), 3.56 (3H, s), 4.06 (2H, m), 6.46 (1H, m), 7.37 (1H, m), 7.22–7.33 (15H, Ar—H), 9.24 (1H, s) ppm.

Preparation of Compound 62: To a solution of Compound 61 (14.6 grams, 17.7 mmoles) in dry THF (300 ml), Compound 54 (5.12 grams, 21.55 mmoles) and triphenylphosphine (11 grams, 37.9 mmoles) were added, under argon atmosphere. The slurry mixture was vigorously stirred for 15 minutes at room temperature and thereafter diethyl azodicarboxylate (Aldrich) (5.96 ml, 37.9 mmoles) was add dropwise thereto during a period of 20 minutes. After the addition was completed, the slurry solution became clear and was stirred at room temperature for additional three hours. The solvent was then evaporated to dryness and the residue was extracted with ethyl acetate (300 ml) and washed with water and brine. The organic layer was dried over sodium sulfate. And the solvent was removed under reduced pressure. The resulting yellowish oily residue was purified by silica gel chromatography, using a mixture if 3:1 ethyl acetate:hexane as eluent. 15.7 grams (81% yield) of Compound 62 were obtained as an oil.

$^1$H-NMR (in CDCl$_3$): δ=1.23 (9H, s), 1.27–1.47 (2H, m), 1.58–1.78 (2H, m), 1.91 (2H, m), 2.37 (2H, m), 2.99 (1H, s), 3.13–3.33 (4H, m), 3.23 (3H, m), 3.49 (2H, m), 3.56 (3H, s), 4.0 (2H, m), 4.06 (2H, m), 6.46 (1H, m), 7.37 (1H, m), 7.22–7.33 (15H, Ar—H), 9.24 (1H, s), 9.26 (1H, s) ppm.

Preparation of Compound 64: Compound 62 (1.10 grams, 1 mmoles) was mixed with concentrated ammonium hydroxide (Aldrich) and the reaction mixture was stirred at room temperature for six hours. The solvent was then evaporated to dryness and the obtained white residue (Compound 63) was re-dissolved in dichloromethane (150 ml). Dicyclocarbodiimide (DCC) (0.247 gram, 1.2 mmoles) was added to the solution at once and the reaction mixture was stirred at room temperature for 16 hours. The obtained mixture was filtered, to remove the produced dicyclohexylurea precipitate, and the solvent was evaporated to dryness. The residue was purified by silica gel chromatography, using a mixture of 4:1 ethyl acetate:hexane as eluent. 0.470 gram (52.9% yield) of Compound 64 was obtained as a white solid.

Preparation of Compound 65: Compound 64 (0.887 gram, 1 mmole) was co-evaporated with dry pyridine and then dissolved in pyridine (150 ml). The solution was cooled to 0° C. by means of an ice bath, methanesulfonylchloride (2.29 grams, 0.158 ml, 2 mmoles) was then added and the mixture was stirred for two hours at room temperature. The solvent was thereafter evaporated to dryness and the residue was extracted with ethyl acetate (250 ml) and washed with water and brine. The organic layer was dried over sodium sulfate and the solvent was removed under educed pressure. 0.89 grams (92% yield) of Compound 65 were obtained as an oily residue.

TLC (ethyl acetate): Rf=0.21.

A 0.1 M stock solution of Compound 65 was prepared by dissolving Compound 65 in dry tetrahydrofuran, under argon atmosphere.

Preparation of oligomers of PEG-nucleobases and Compound 65: The preparation of the products obtained by the condensation of compound 65 with compounds 29 and 30, as representative examples, were performed using the same procedures described under Examples 4 and 5. Antisense oligonucleotide analogs including both an acyclic nucleobases and cyclic dimeric nucleobases linked therebetween by a linker chain were thus obtained.

Although the invention has been described in conjunction with specific embodiments thereof; it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A compound having the formula:

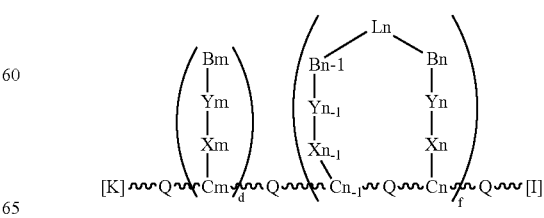

49 wherein:
m and n are each independently an integer;
m≠n;
m≠n-1;
d is an integer which equals to or greater than 0;
f is an integer greater than 0;
L is a linker chain;
each of Bm, Bn-1 and Bn is a chemical functionality group independently selected from the group consisting of a naturally occurring nucleobase and a nucleobase binding group;
each of Ym, Yn-1 and Yn is a first linker group;
each of Xm, Xn-1 and Xn is a second linker group;
Cm, Cn-1 and Cn are chiral carbon atoms;
Q is a backbone bearing said Cm, Cn-1 and Cn chiral carbon atoms; and
[K] and [I] are optional first and second exoconjugates.

2. The compound of claim 1, wherein each of said Ym-Xm, Yn-1-Xn-1 and Yn-Xn linker groups is a single bond.

3. The compound of claim 1, wherein each of said Yin, Yn-1 and Yn first linker groups is independently selected from the group consisting of an alkyl group, a phosphate group, a (C2–C4) alkylene chain, a (C2–C4) substituted alkylene chain and a single bond.

4. The compound of claim 1, wherein each of said Yin, Yn-1 and Yn first linker groups is independently selected from the group consisting of a methylene group and a C-alkanoyl group.

5. The compound of claim 1, wherein each of said Xm, Xn-1 and Xn second linker groups is independently selected from the group consisting of a methylene group, an alkyl group, an amino group, an amido group, a sulfur atom, an oxygen atom, a selenium atom, a C-alkanoyl group, a phosphate derivative group, a carbonyl group and a single bond.

6. The compound of claim 1, wherein m percents of said chiral carbons are in an S configuration, wherein m is selected from the group consisting of 90–95%, 96–98%, about 99% and greater than 99%.

7. The compound of claim 1, wherein [K] and [I] are each independently a polyethylene glycol moiety.

8. The compound of claim 1, wherein said Q backbone comprises a polyether and/or a polyether derivative, said polyether derivative being selected from the group consisting of poly(ether-thioether), poly(ether-sulfone) and poly(ether-sulfoxide).

9. The compound of claim 8, wherein said polyether comprises poly(ethylene glycol).

10. The compound of claim 1, wherein said backbone is selected from the group consisting of a thiophosphonate DNA backbone, a phosphoramidate backbone, a morpholino phosphoramidate backbone and a methyl phosphonate backbone.

11. The compound of claim 1, wherein said Cm, Cn-1 and Cn chiral carbon atoms are separated from one another in said Q backbone by from four to six intervening atoms.

12. The compound of claim 1, wherein said L linker chain comprises between four and fourteen atoms.

13. The compound of claim 12, wherein said L linker chain has a formula:

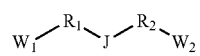

50 wherein:
R1 and R2 are each independently selected from the group consisting of a methylene group, a substituted or unsubstituted saturated alkylene chain and a substituted or unsubstituted unsaturated alkylene chain;
W1 and W2 are each independently selected from the group consisting of a single bond, a double bond and a triple bond; and
J is selected from the group consisting of alkyl, aryl, amide, amine, ether, ester, carbonyl, thiocarbonyl, phosphate, carbamate, thioether, disulfide, sulfone and sulfoxide.

14. The compound of claim 1, further comprising at least one reporter molecule linked to said backbone.

15. A compound having a formula:

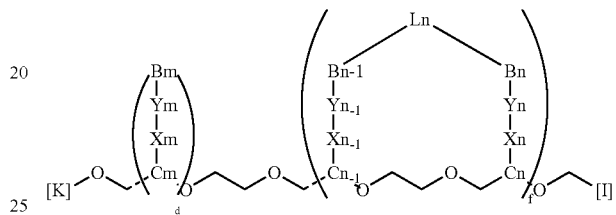

wherein:
m and n are each independently an integer;
m≠n;
m≠n-1;
d is an integer which equals to or greater than 0;
f is an integer greater than 0;
L is a linker chain;
each of Bm, Bn-1 and Bn is a chemical functionality group independently selected from the group consisting of a naturally occurring nucleobase and a nucleobase binding group;
each of Ym, Yn-1 and Yn is a first linker group; each of Xm, Xn-1 and Xn is a second linker group;
Cm, Cn-1 and Cn are chiral carbon atoms; and
[K] and [I] are optional first and a second exoconjugates.

16. The compound of claim 15, wherein each of said Ym-Xm, Yn-1-Xn-1 and Yn-Xn linker groups is a single bond.

17. The compound of claim 15, wherein each of said Ym, Yn-1 and Yn first linker groups is independently selected from the group consisting of an alkyl group, a phosphate group, a (C2–C4) alkylene chain, a (C2–C4) substituted alkylene chain and a single bond.

18. The compound of claim 15, wherein each of said Ym, Yn-1 and Yn first linker groups is independently selected from the group consisting of a methylene group and a C-alkanoyl group.

19. The compound of claim 15, wherein each of said Xm, Xn-1 and Xn second linker groups is independently selected from the group consisting of a methylene group, an alkyl group, an amino group, an amido group, a sulfur atom, an oxygen atom, a selenium atom, a C-alkanoyl group, a phosphate derivative group, a carbonyl group and a single bond.

20. The compound of claim 15, wherein m percents of said chiral carbons are in an S configuration, wherein m is selected from the group consisting of 90–95%, 96–98%, about 99% and greater than 99%.

21. The compound of claim 15, wherein [K] and [I] are each a polyethylene glycol moiety.

22. The compound of claim 15, wherein each of said L linker chain comprises between four and fourteen atoms.

23. The compound of claim 22, wherein each of said L linker chain has a formula:

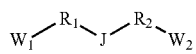

wherein:

R1 and R2 are each independently selected from the group consisting of a methylene group, a substituted or unsubstituted saturated alkylene chain and a substituted or unsubstituted unsaturated alkylene chain;

W1 and W2 are each independently selected from the group consisting of a single bond, a double bond and a triple bond; and J is selected from the group consisting of alkyl, aryl, amide, amine, ether, ester, carbonyl, thiocarbonyl, phosphate, carbamate, thioether, disulfide, sulfone and sulfoxide.

24. The compound of claim 15, further comprising at least one reporter molecule linked thereto.

25. The compound of claim 15, having the formula:

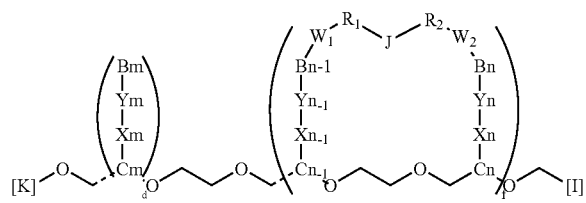

wherein:

R1 and R2 are each independently selected from the group consisting of a methylene group, a substituted or unsubstituted saturated alkylene chain and a substituted or unsubstituted unsaturated alkylene chain;

W1 and W2 are each independently selected from the group consisting of a single bond, a double bond and a triple bond; and J is selected from the group consisting of alkyl, aryl, amide, amine, ether, ester, carbonyl, thiocarbonyl, phosphate, carbamate, thioether, disulfide, sulfone and sulfoxide.

26. The compound of claim 25, having the formula:

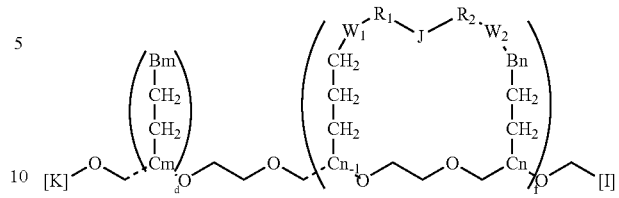

27. The compound of claim 15, having the formula:

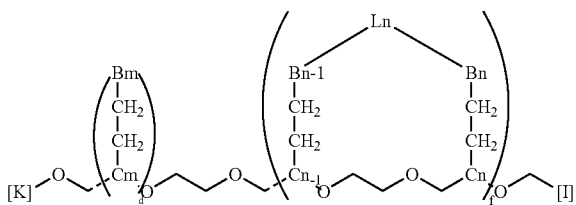

28. The compound of claim 27, wherein said L linker chain comprises between four and fourteen atoms.

29. The compound of claim 28, wherein said L linker chains has a formula:

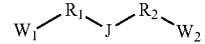

wherein:

R1 and R2 are each independently selected from the group consisting of a methylene group, a substituted or unsubstituted saturated alkylene chain and a substituted or unsubstituted unsaturated alkylene chain;

W1 and W2 are each independently selected from the group consisting of a single bond, a double bond and a triple bond; and J is selected from the group consisting of alkyl, aryl, amide, amine, ether, ester, carbonyl, thiocarbonyl, phosphate, carbamate, thioether, disulfide, sulfone and sulfoxide.

30. A pharmaceutical composition comprising, as an active ingredient, the compound of claim 1, and a pharmaceutically acceptable carrier.

31. A pharmaceutical composition comprising, as an active ingredient, the compound of claim 15, and a pharmaceutically acceptable carrier.

32. A pharmaceutical composition comprising, as an active ingredient, the compound of claim 25, and a pharmaceutically acceptable carrier.

33. A pharmaceutical composition comprising, as an active ingredient, the compound of claim 27, and a pharmaceutically acceptable carrier.

* * * * *